US008178688B2

(12) United States Patent
Lee et al.

(10) Patent No.: US 8,178,688 B2
(45) Date of Patent: May 15, 2012

(54) BENZAMIDINE DERIVATIVES, PROCESS FOR THE PREPARATION THEREOF AND PHARMACEUTICAL COMPOSITION COMPRISING THE SAME

(75) Inventors: Jin Soo Lee, Yongin-si (KR); Seok Hoon Ahn, Seoul (KR); Young Goo Jin, Seoul (KR); Sang Mi Jin, Suwon-si (KR); Whui-Jung Park, Suwon-si (KR); Sae Kwang Ku, Suwon-si (KR); Yun Ha Hwang, Ansan-si (KR); Pan Soo Kim, Anyang-si (KR); Sun Shin Yi, Anyang-si (KR); Jei Man Ryu, Anyang-si (KR)

(73) Assignee: Dong Wha Pharmaceutical Co., Ltd., Seoul (KR)

( * ) Notice: Subject to any disclaimer, the term of this patent is extended or adjusted under 35 U.S.C. 154(b) by 969 days.

(21) Appl. No.: 11/659,556

(22) PCT Filed: Aug. 4, 2005

(86) PCT No.: PCT/KR2005/002545
§ 371 (c)(1),
(2), (4) Date: Oct. 11, 2007

(87) PCT Pub. No.: WO2006/014087
PCT Pub. Date: Feb. 9, 2006

(65) Prior Publication Data
US 2010/0240890 A1 Sep. 23, 2010

(30) Foreign Application Priority Data
Aug. 4, 2004 (KR) .................. 10-2004-0061481

(51) Int. Cl.
C07D 277/20 (2006.01)
C07D 277/30 (2006.01)
C07D 417/02 (2006.01)
C07D 417/04 (2006.01)
C07D 417/06 (2006.01)
C07D 417/08 (2006.01)

(52) U.S. Cl. ........ 548/190; 548/184; 548/204; 548/202; 546/209; 546/270.4; 546/270.7; 546/269.7

(58) Field of Classification Search .................. None
See application file for complete search history.

(56) References Cited

U.S. PATENT DOCUMENTS

| 6,197,824 | B1 | 3/2001 | Schromm et al. | |
|---|---|---|---|---|
| 7,662,840 | B2* | 2/2010 | Suh et al. | 514/365 |
| 7,943,646 | B2* | 5/2011 | Ryu et al. | 514/365 |
| 8,008,329 | B2* | 8/2011 | Ryu et al. | 514/365 |
| 2007/0254930 | A1* | 11/2007 | Ryu et al. | 514/365 |
| 2008/0125596 | A1* | 5/2008 | Lee et al. | 548/202 |
| 2008/0200526 | A1* | 8/2008 | Lee et al. | 514/365 |
| 2008/0255212 | A1* | 10/2008 | Keil et al. | 514/364 |
| 2008/0287509 | A1* | 11/2008 | Ryu et al. | 514/365 |
| 2009/0054642 | A1* | 2/2009 | Ryu et al. | 544/60 |
| 2009/0176846 | A1* | 7/2009 | Ryu et al. | 514/365 |
| 2010/0029595 | A1* | 2/2010 | Ryu et al. | 514/108 |
| 2010/0029596 | A1* | 2/2010 | Ryu et al. | 514/108 |
| 2010/0113538 | A1* | 5/2010 | Lee et al. | 514/365 |
| 2010/0160394 | A1* | 6/2010 | Suh et al. | 514/365 |
| 2010/0249402 | A1* | 9/2010 | Ryu et al. | 544/60 |
| 2011/0306580 | A1* | 12/2011 | Ochiai et al. | 514/167 |

FOREIGN PATENT DOCUMENTS

| JP | 6-263710 A | 9/1994 |
|---|---|---|
| KR | 102003000865 | 1/2003 |
| KR | 100513302 B1 | 8/2005 |
| WO | WO-94/21616 A1 | 9/1994 |
| WO | WO-95/32201 A1 | 11/1995 |
| WO | WO 03/007947 A1 | 1/2003 |
| WO | WO-2006/004369 A1 | 1/2006 |
| WO | WO-2006/004370 A1 | 1/2006 |

OTHER PUBLICATIONS

Seong-Eun Lee "Design, syntheses, and evaluation of the functional molecules for the treatment of the LTB4 related disease and electroluminescent device" In: Doctoral Dissertation, Department of Chemistry, Graduate School of Arts and Science, Busan Univ, South Korea (Aug. 1999) (221 Pages).
Robertson et al, "Late asthmatic responses induced by ragweed ragweed pollen allergen," J. Allergy Clin. Immun, Oct. 1974, vol. 54, pp. 244-254.
Wang, Elizabeth A. et al, "Recombinant human bone morphogenetic protein induces bone formation," Proc. Nati. Acad. Sci. USA Mar. 1990 vol. 87, pp. 2220-2224.
Kawamura, Morio M.D. "Induction of Callus Formation by Implants of Bone Morphogenetic Protein and Associated Bone Matrix Noncollagenous Proteins" Clinical Orthopaedics & Related Research .Nov. 1988. STET (Abstract Only) (1 pg.).
T. Kinoshita et al, "Phosphodiesterase inhibitors, pentoxifylline and rolipram, increase bone mass mainly by promoting bone formation in normal mice" Bone vol. 27, Issue 6, Dec. 2000, pp. 811-817 (Abstract Only) (2 pgs.).
Beasley et al, "Cellular Events in the Bronchi in Mild Asthma and after Bronchial Provocation" Am Rev Respir Dis. 1989, p. 306-317.
English Translation of Abstract; Korean Publication No. KR 100513302 (B1); Applicant: Dong Wha Pharma Ind. Co., LTD; Published Aug. 31, 2005 (Abstract Only) (1 pg.).

* cited by examiner

Primary Examiner — Kamal Saeed
Assistant Examiner — Nyeemah A Grazier
(74) Attorney, Agent, or Firm — Arent Fox LLP

(57) ABSTRACT

The present invention relates to novel benzamidine derivatives, process for the preparation thereof and pharmaceutical composition comprising the same. The novel benzamidine derivatives of the present invention are useful for the prevention and treatment of osteoporosis, bone fractures and allergic inflammatory diseases.

24 Claims, No Drawings

BENZAMIDINE DERIVATIVES, PROCESS FOR THE PREPARATION THEREOF AND PHARMACEUTICAL COMPOSITION COMPRISING THE SAME

TECHNICAL FIELD

The present invention relates to novel benzamidine derivatives, process for the preparation thereof and pharmaceutical composition comprising the same.

BACKGROUND ART

Bone is the body's framework. Bone contains calcium ($Ca^{2+}$) and plays an important role in maintaining the calcium level in blood. To this end, the growth of bone is a metabolic balance between the activity of osteoblasts and osteoclasts in the bone remodeling cycle.

When the balance between bone absorption and bone formation is disrupted, the amount of bone tissue replaced by osteoblasts fails to match that absorbed by osteoclasts, thus leading to osteoporosis, a common condition which result in the loss of bone density or bone mass. This disease frequently occurs in middle-aged or elderly women.

Osteoporosis is a metabolic bone disease, which results from a disturbance in the normal bone remodeling, tilting the balance between bone resorption and formation, thus resulting in bone loss and fractures after mineral flux. Bone is the dynamic structures, in which the osteoblast bone formation and osteoclast bone resorption are continuously occurred.

Previous studies focused on the metabolisms of bone inorganic materials like calcium and inorganic phosphorus. Such studies did not provide sufficient findings regarding the mechanisms of osteoporosis.

Although bisphosphonates (alendronate, etidronate etc.), hormones (raloxifen), Vitamin D, Calcitonin, calcium agents, etc. have been used as anti-osteoporetic agents, they have some adverse side effect or defects. Bisphosphontes show low pharmacokinetic profiles, are difficult to dose and may induce esophagitis. Hormone agents must be administered continuously. Also, in case of long term therapy, severe side effects such as breast cancer, gallstones and embolism may be induced. Vitamin D agents are expensive and show little efficacy in treating estrogen-deficient osteoporetic patients. Calcitonin is also very expensive and difficult to administrate. Calcium has few adverse side effects, but its effects is restricted to the prevention of osteoporosis not the treatment of it.

Osteoporosis requires long term therapy, thus it is necessary for the development of new drugs to not include the above-mentioned adverse effects.

A bone fracture is a break or crack in a bone, with complete or incomplete disruption of the continuity of a bone, epiphyseal plate or articular surface. A bone fracture is caused mostly by some type of trauma to a bone. This trauma might occur as a result of a motor vehicle accident, workplace accident, physical abuse, repetitive stress such as exercise, heavy lifting, etc. According to fracture line (line along epiphyseal ends generated upon fracture), bone fractures are classified into fissured fractures, greenstick fractures, transverse fractures, oblique fractures, spiral fractures, segmental fractures, comminuted fractures, avulsion fractures, compression fractures, depressed fractures, etc.

It is common for bone fractures to injure blood, thus resulting in partial hemorrhage and blood clots. In addition, the bone matrix around a fracture region breaks down or ruptures, with the death of osteocytes. During a fracture healing process, hence, the blood clots and the injured osteocytes and bone matrix are removed by macrophages while osteoprogenitor cells of the perilsteum and endosteum around the fracture region actively proliferate to form cellular tissue around the fracture region and are then integrated with the fracture region. In the connective tissue of the fracture region, either a bone tissue arises by endochondral ossification from a small cartilage fragment or an immature bone is formed by intramembranous ossification. Accordingly, intramembranous ossification from mesenchymal tissue and endochondral ossification are observed concurrently in the connective tissue of a fracture region. The trabecula of the immature bone irregularly formed in this way temporarily connects ends of the fractured bone fragments, resulting in the formation of a bony callus. The woven bone of the bony callus formed in the fracture region is gradually resorbed as the healing process progresses, and undergoes rearrangement resulting in the development of lamellar bone.

The healing process for fracture is largely divided into three phases: inflammatory phase, bone reparative phase, and remodeling phase.

In the inflammatory phase, inflammatory responses occur since tissues around a fracture region are injured and hematoma fills the fracture gap.

In the bone reparative phase, the hematoma is removed from the fracture gap and substituted with granulation tissue while soft callus is formed. According to the osteogenesis mechanism, two processes proceed concurrently: endochondral ossification, in which the soft callus is remodeled into hard callus, and fibrous/intramembranous ossification, in which a new bone is formed by osteogenic cells.

In the remodeling phase, newly formed bone tissue is extended over a long period of time by the orchestrated action of osteoclastic bone resorption and osteoblastic bone formation, with the correction of bone distortions and the reinforcement of bone defects.

During the remodeling phase, patients with a bone fracture conduct their lives without great difficulty because the newly formed bone has become hard to some extent, but the nascent bone tissue in the reparative phase is not hard enough for patients to live their daily lives without difficulty. In addition, the reparative phase is long. Thus, it is clinically important for a fracture curative to have the function of shortening the reparative phase as well as regenerating a fractured bone into a complete bone by promoting the complex fracture healing process.

There are various promoters for fracture healing. Peptides having physiologically active functions, such as bone morphogenic proteins (BMPs) and transforming growth factors (TGFs), are found to be involved in the fracture healing process (Proc. Natl. Acad. Sci., USA, vol. 87, pp. 2220-2224 (1989)). Also, it has been studied that an increase in intracellular cyclic AMP level by use of a phosphodiesterase (PDE) inhibitor can lead to an increase in bone mass. For example, it is reported that mice, into which the general PDE inhibitor pentoxipylline or the selective PDE4 inhibitor rolipram had been subcutaneously injected every day, were observed to have the vertebrate and femur increased in bone mineral density, and showed hyperplasia of cortical bones (Bone, vol. 27, 6th edition, pp. 811-817 (2000)).

As mentioned above, attention has long been paid to osteogenesis and fracture healing, and extensive studies on fracture healing processes have been conducted from various points of view, including genetic factors, adolescent influence, hematopoietic effect, fixture effect, bone grafts, other healing promoting factors, etc. (Kawamura, M and Urist M R., Clin. Orthop., 236, 240-248, 1988).

Fracture healing requires a significant period of time and elderly patients with osteoporosis tend to suffer more from bone fractures. Falling short of the expectation of usefulness in fracture healing, currently available therapeutic agents for the treatment of osteoporosis, such as calcium, estrogen, calcitonin, active vitamin D, biphosphonate, etc., are found only to lower the risk of fracture by obstructing the decrease of bone density, and have no function of joining fractured bones or generating bone tissues. The pathogenic mechanism of osteoporosis can be explained by a subtle bone matrix resulting from long maintenance of negative bone homeostasis due to genetic or constitutional predispositions, stagnant osteogenesis with normal bone resorption, and increased bone resorption with normal osteogenesis. Osteoporosis agents are, therefore, ineffective for the treatment of bone fractures because the healing mechanism is quite different between fractures and osteoporosis.

Therefore, there is an urgent need for a bone fracture curative agent that has great therapeutic effect on bone fractures, regardless of association with osteoporosis As diverse pathologies associated with environmental pollution, stress, living environments, etc., an allergic inflammatory disease has increased. Allergic inflammatory disease is attributed to abnormality in the immune system where the nasal or bronchial mucosa or skin is hypersensitive to external allergens. Basic causes of allergy include nutrition imbalance, stress, extravasated blood, etc., with the major cause being nutrition imbalance.

Depending on the site where immune responses occur against exogenous allergens, allergic inflammatory disease is represented as various symptoms including allergic rhinitis, asthma, atopic dermatitis, etc. In addition, allergic conjunctivitis, allergic dermatitis, contact dermatitis, urticaria, etc. are within the scope of allergic inflammatory diseases. Since these symptoms, although very diverse, are common in the pathology based on the hypersensitivity to externally introduced matter, a suppressant of excessive immune responses can be prescribed for all of them.

Asthma, representative of allergies, is a chronic inflammatory disease occurring in the respiratory organ, especially, the lungs and the bronchi. When patients with asthma take drugs or excessive exercise or inhale contaminated and/or cold air, their respiratory organs, especially, upper respiratory organs increase in responsiveness. This hyper-responsiveness is associated with the airflow obstruction in the airway, that is, airway obstruction or tracheal stenosis, but is readily alleviated using a bronchodilator. Included in the consensus characteristics of asthma, hyper-responsiveness to indoor and/or outdoor allergens and airway contraction are known to be mediated by mast cells and eosinophil IgE (Beasley et al., Am. Rev. Respir. Dis., 129, 806-817, 1989).

Asthma is accompanied by the allergic hyper-responsiveness mainly in the bronchia and the lungs. Particularly, the air passage becomes clogged by the proliferation of mucous cells and the inflammation of epithelial connective tissues in the bronchia. Alsom the lungs are known to show similar histological behaviors. The pathology of asthma, although not yet clearly revealed thus far, is reported to be featured by airway stenosis, edema, mucus secretion, inflammatory cell infiltration, etc. In the mechanism of a typical exogenous asthma, when an antigen is introduced into the airway, B cells produce antigen specific antibodies IgE and IgG in cooperation with macrophages and helper T-cells. These antigen specific antibodies bind to receptors on the surfaces of mast cells and basophils, which are then activated upon re-exposure to the same antigen so as to release various cytokines and mediators of allergy/inflammation, including histamine, prostaglandin $D_2$, slow reacting substances (leukotriene $C_4$, $D_4$), etc. out of the cells. Due to these cytokines and mediators, when exposed to aeroallergen, patients with asthma exhibit an early asthma response characterized by a rapid airway constriction over a period of seconds to minutes and apparent recovery within 30 to 60 min from the constriction. Then, the mediators secreted from mast cells and the cytokines secreted from macrophages, mast cells and helper T-cells proliferate and activate inflammatory cells, including eosinophils, to exhibit a late asthmatic response in which bronchoconstriction, mucus secretion and inflammatory cell infiltration begin 3 to 4 hours and peak 4 to 18 hours after exposure to aeroallergens (Robertson et al., J. Allergy Clin. Immunol., 54, 244-257, 1974).

Currently available therapeutic agents for the treatment of asthma include beta 2-adreno receptor agonists, which dilate airway smooth muscles and effectively, inhibit the secretion of hyperresponsiveness mediators from mast cells, adrenal cortical hormones, which exhibit an immunosuppressive effect, and disodium cromoglycate and nedocromil sodium, both known to inhibit both the early and the late asthma response. However, beta 2-adreno receptor antagonists show the treatment effect only for a short period of time and allow the ready recurrence of the disease. Adrenal cortical hormones have fragmentary treatment effects, with the concomitance of serious side effects upon long-term dosage.

Leading to the present invention, intensive and thorough study on osteoporosis, bone fractures and allergic inflammatory diseases conducted by the present inventors, resulted in the finding that novel benzamidine derivatives have effects on suppressing the osteoclastic bone resorption and inhibiting the decrease of bone mass in animal models, indication the compounds are useful in the prevention and treatment of osteoporosis; healing bone fractures; and treating and preventing allergic inflammatory disease.

DISCLOSURE OF THE INVENTION

An object of the present invention is to provide novel benzamidine derivatives. Another objective of the present invention is to provide their preparation method. Further another object of the present invention is to provide pharmaceutical compositions for the prevention and treatment of osteoporosis, allergic inflammatory diseases and bone fractures comprising novel benzamidine derivatives.

BEST MODE FOR CARRYING OUT THE INVENTION

The invention relates to novel benzamdine derivatives of the formula 1 or pharmaceutically acceptable salts thereof:

Formula 1

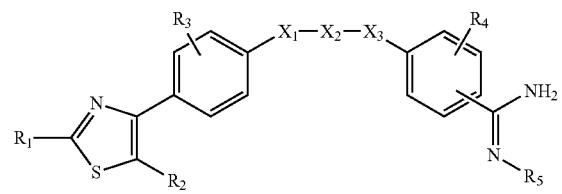

wherein
$R_1$ is $C_1$~$C_6$ alkyl; $C_3$~$C_6$ cycloalkyl; phenyl; benzyl; pyridinyl; guanidino; $NR_6R_7$; $CH_2NR_6R_7$;

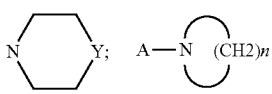

wherein A is $C_1$~$C_6$ alkyl and n is an integer of 2 to 6; $C_1$~$C_6$ alkyl which is substituted by pyridine or

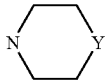

wherein

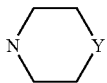

is unsubstituted or substituted by hydroxy; pyridinyl or

which is substituted by $C_1$~$C_6$ alkyl;

$R_2$ is hydrogen; $C_1$~$C_6$ alkyl; $C_3$~$C_6$ cycloalkyl; phenyl; benzyl; $C_1$~$C_6$ alkyl which is substituted by hydroxy, $C_1$~$C_6$ alkoxy, halogen or $C_3$~$C_6$ cycloalkyl; $C_2$~$C_6$ alkenyl;

$R_3$ and $R_4$, each independently, are hydrogen; halogen; hydroxy; $C_1$~$C_6$ alkyl which is unsubstituted or substituted halogen; $C_3$~$C_6$ cycloalkylamino; $C_1$~$C_6$ alkoxy; $C_1$~$C_6$ alkanoyloxy; $C_2$~$C_6$ alkenyloxy; phenyl-$C_1$~$C_6$ alkoxy; phenoxy; $C_2$~$C_6$ alkenoyloxy or phenyl-$C_1$~$C_6$ alkanoyloxy; $C_3$~$C_6$ cycloalkyloxy which is substituted by carboxy, esterified carboxy or amidated carboxy; aminooxy;

$R_5$ is hydrogen or hydroxy;

$R_6$ and $R_7$, each independently, are hydrogen; $C_1$~$C_6$ alkyl; phenyl; benzyl; pyridinyl; $C_1$~$C_6$ alkyl which is substituted by pyridine or

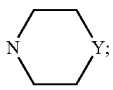

carbonyl which is substituted by $C_1$~$C_6$ alkyl, phenyl, benzyl, pyridine or

$C_1$~$C_6$ alkanesulfonyl; $C_1$~$C_6$ alkyl which is substituted by hydroxy or $C_1$~$C_6$ alkoxy; acetyl which is substituted by hydroxy or $C_1$~$C_6$ alkoxy;

Y is oxygen; sulfur; $NR_6$; or $CH_2$;

$X_1$ and $X_3$, each independently, are oxygen; sulfur; NH; N—$C_1$~$C_6$ alkyl; N—$C_3$~$C_6$cycloalkyl; N-benzyl; N-phenyl;

$X_2$ is $C_3$-$C_7$ alkylene; $C_1$-$C_3$ alkylene-alkenylene-$C_1$-$C_3$-alkylene; $C_1$-$C_3$ alkylene-O—$C_1$-$C_3$ alkylene; $C_1$-$C_3$ alkylene-S—$C_1$-$C_3$ alkylene; $C_1$-$C_3$ alkylene-NH—$C_1$-$C_3$ alkylene; $C_1$-$C_3$ alkylene-phenylene-$C_1$-$C_3$ alkylene; $C_1$-$C_3$ alkylene-pyridylene-$C_1$-$C_3$ alkylene; $C_1$-$C_3$ alkylene-naphtylene-$C_1$-$C_3$ alkylene; $C_3$-$C_7$ alkylene which is substituted by $C_1$-$C_3$ alkyl and hydroxy; $C_3$-$C_7$ alkylenecarbonyl; $C_3$-$C_7$ alkylene which is interrupted by piperazine.

The invention especially relates to compounds of the formula 1 in which:

$R_1$ is $C_1$~$C_6$ alkyl; $C_3$~$C_6$ cycloalkyl; phenyl; pyridinyl; guanidino; $NR_6R_7$; $CH_2NR_6R_7$;

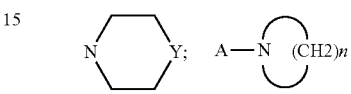

wherein A is $C_1$~$C_6$ alkyl and n is an integer of 2 to 6; $C_1$~$C_6$ alkyl which is substituted by

wherein

is unsubstituted or substituted by hydroxy;

which is substituted $C_1$~$C_6$ alkyl;

$R_2$ is hydrogen; $C_1$~$C_6$ alkyl; $C_3$~$C_6$ cycloalkyl; benzyl; $C_1$~$C_6$ alkyl which is substituted by hydroxyl, methoxy, halogen or $C_3$~$C_6$ cycloalkyl; $C_2$~$C_6$ alkenyl;

$R_3$ and $R_4$ each independently, are hydrogen; halogen; hydroxy; $C_3$~$C_6$ cycloalkylamino; $C_1$~$C_6$ alkoxy; $C_1$~$C_6$ alkanoyloxy; $C_3$~$C_6$ cycloalkyloxy which is substituted by carboxy, esterified carboxy or amidated carboxy; aminooxy;

$R_5$ is hydrogen or hydroxy;

$R_6$ and $R_7$ each independently, are hydrogen; $C_1$~$C_6$ alkyl; benzyl; pyridinyl; $C_1$~$C_6$ alkyl which is substituted by pyridine or

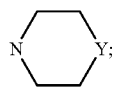

carbonyl which is substituted by pyridine or $C_1$~$C_6$ alkyl; $C_1$~$C_6$ alkanesulfonyl; $C_1$~$C_6$ alkyl which is substituted by hydroxy or $C_1$~$C_6$ alkoxy; acetyl which is substituted by hydroxy or $C_1$~$C_6$ alkoxy;

Y is oxygen; sulfur; $NR_6$; $CH_2$;

$X_1$ and $X_3$, each independently, are oxygen; sulfur; NH; N—$C_1$~$C_6$ alkyl;

$X_2$ is $C_3$-$C_7$ alkylene; $C_1$-$C_3$ alkylene-alkenylene-$C_1$-$C_3$-alkylene; $C_1$-$C_3$ alkylene-O—$C_1$-$C_3$ alkylene; $C_1$-$C_3$ alkylene-NH—$C_1$-$C_3$ alkylene; $C_1$-$C_3$ alkylene-phenylene-$C_1$-$C_3$ alkylene; $C_1$-$C_3$ alkylene-pyridylene-$C_1$-$C_3$ alkylene; $C_1$-$C_3$ alkylene-naphtylene-$C_1$-$C_3$ alkylene; $C_3$-$C_7$ alkylene which is substituted by $C_1$-$C_3$ alkyl or hydroxy; $C_3$-$C_7$ alkylenecarbonyl; $C_3$-$C_7$ alkylene which is interrupted by piperazine.

The invention further especially relates to compounds of the formula 1 in which:

$R_1$ is methyl; ethyl; propyl; isopropyl; butyl; t-butyl; pentyl; cyclopentyl; hexyl; cyclohexyl; phenyl; aminomethyl; aminoethyl; amino; isobutylamide; guanidino; 1-propyl-piperidino; 2-morpholinomethyl; $NR_6R_7$; $CH_2NR_5R_7$;

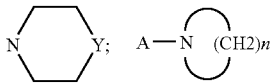

wherein A is $C_1$~$C_6$ alkyl and n is an integer of 2 to 6; pyridinyl; 4-hydroxypiperidinomethyl; cyclohexylaminomethyl;

$R_2$ is hydrogen; methyl; ethyl; isopropyl; propyl; butyl; isobutyl; methoxymethyl; hydroxymethyl; 2-methylpropyl; pentyl; chloromethyl; chloroethyl; cyclopentyl; cyclopentylmethyl; cyclohexyl; benzyl; vinyl;

$R_3$ and $R_4$, each independently, are hydrogen; halogen; hydroxy; cyclohexylamino; methoxy; $C_1$-$C_4$ alkanoyloxy; $C_1$-$C_7$ aliphatic alkoxy which is substituted by carboxy, esterified carboxy or amidated carboxy;

$R_5$ is hydrogen or hydroxy;

$R_6$ and $R_7$, each independently, are hydrogen; methyl; ethyl; propyl; benzyl; pyridin-3-yl; pyridin-4-yl; 2-morpholinoethyl; 4-pyridinylcarbonyl; 3-pyridinylcarbonyl; isobutylcarbonyl; ethanesulfonyl; methoxyethyl; hydroxyethyl; hydroxyacetyl; methoxyacetyl;

Y is oxygen; sulfur; $NR_6$; $CH_2$;

$X_1$ and $X_3$, each independently, are oxygen; sulfur; amine; methylamine;

$X_2$ is propylene; butylene; pentylene; hexylene; heptylene; ethylene-O-ethylene; 3-hydroxy-3-methyl-pentylene; methylethylene-NH-ethylene; ethylene-NH-ethylene; propylene which is interrupted by piperazine; butylene carbonyl; 2-butenyl; methylene-phenylene-methylene; methylene-pyridylene-methylene; 1,2-ethylene-1,4-phenylene-1,2-ethylene; 1,3-propylene-1,4-phenylene-1,3-propylene; 1,2-ethylene-naphthalene-1,2-ethylene.

The invention furthermore especially relates to compounds of the formula 1 in which, $R_1$ is methyl; ethyl; isopropyl; cyclohexyl; phenyl; aminomethyl; aminoethyl; amino; pyridinyl; $NR_6R_7$; $CH_2NR_6R_7$;

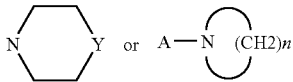

wherein A is $C_1$~$C_2$ alkyl and n is an integer of 4 to 5;

$R_2$ is hydrogen; methyl; ethyl; isopropyl; isobutyl; methoxymethyl; hydroxymethyl; chloromethyl; chloroethyl; cyclopentyl; cyclopentylmethyl; vinyl;

$R_3$ and $R_4$, each independently, are hydrogen; halogen; hydroxy; methoxy;

$R_5$ is hydrogen or hydroxy;

$R_6$ and $R_7$, each independently, are hydrogen; methyl; ethyl; benzyl; pyridin-3-yl; pyridin-4-yl; 2-morpholinoethyl; 4-pyridinylcarbonyl; 3-pyridinylcarbonyl; isobutylcarbonyl; ethanesulfonyl; hydroxyethyl; methoxyethyl;

Y is oxygen; sulfur; methylamine;

$X_1$ and $X_3$, each independently, are oxygen; sulfur; amino; methylamine;

$X_2$ is propylene; butylene; pentylene; hexylene; ethylene-O-ethylene; ethylene-NH-ethylene; butylenecarbonyl; 2-butenyl; methylene-1,2-phenylene-methylene; methylene-1,3-phenylene-methylene; methylene-1,4-phenylene-methylene; methylene-pyridinyl-methylene.

In the compounds of the formula 1 of the present invention, the —C($NH_2$)=N—$R_5$ group is in the meta or para position, and $R_3$ and $R_4$ are in the ortho or meta position relative to —$X_1$— or —$X_3$—.

The preferred compounds of the present invention is described in following:

1) N-hydroxy-4-(5-[4-(2-isopropyl-5-methyl-1,3-thiazol-4-yl)phenoxy]pentoxy)-benzamidine,
2) 4-(5-[4-(2-isopropyl-5-methyl-1,3-thiazol-4-yl)phenoxy]pentoxy)-benzamidine,
3) N-hydroxy-4-(5-[4-(2-methyl-1,3-thiazol-4-yl)phenoxy]pentoxy)-benzamidine,
4) N-hydroxy-4-(5-[4-(2-ethyl-1,3-thiazol-4-yl)phenoxy]pentoxy)-benzamidine,
5) N-hydroxy-4-(5-[4-(2-isopropyl-1,3-thiazol-4-yl)phenoxy]pentoxy)-benzamidine,
6) N-hydroxy-4-(5-[4-(2-phenyl-1,3-thiazol-4-yl)phenoxy]pentoxy)-benzamidine,
7) N-hydroxy-4-(5-[4-(2-pyridin-3-yl-1,3-thiazol-4-yl)phenoxy]pentoxy)-benzamidine,
8) N-hydroxy-4-(5-[4-(2-cyclohexyl-1,3-thiazol-4-yl)phenoxy]pentoxy)-benzamidine,
9) N-hydroxy-4-(5-[4-(2-pentyl-1,3-thiazol-4-yl)phenoxy]pentoxy)-benzamidine,
10) N-hydroxy-4-(5-[4-(2,5-dimethyl-1,3-thiazol-4-yl)phenoxy]pentoxy)-benzamidine,
11) N-hydroxy-4-(5-[4-(2-ethyl-5-methyl-1,3-thiazol-4-yl)phenoxy]pentoxy)-benzamidine,
12) N-hydroxy-4-(5-[4-(5-methyl-2-phenyl-1,3-thiazol-4-yl)phenoxy]pentoxy)-benzamidine,
13) N-hydroxy-4-(5-[4-(5-methyl-2-pyridin-3-yl-1,3-thiazol-4-yl)phenoxy]pentoxy)-benzamidine,
14) N-hydroxy-4-(5-[4-(2-cyclohexyl-5-methyl-1,3-thiazol-4-yl)phenoxy]pentoxy)-benzamidine,
15) N-hydroxy-4-(5-[4-(5-methyl-2-pentyl-1,3-thiazol-4-yl)phenoxy]pentoxy)-benzamidine,
16) N-hydroxy-4-(5-[4-(2-t-butyl-5-methyl-1,3-thiazol-4-yl)phenoxy]pentoxy)-benzamidine,
17) N-hydroxy-4-(5-[4-(5-ethyl-2-methyl-1,3-thiazol-4-yl)phenoxy]pentoxy)-benzamidine,
18) N-hydroxy-4-(5-[4-(2,5-diethyl-1,3-thiazol-4-yl)phenoxy]pentoxy)-benzamidine,
19) N-hydroxy-4-(5-[4-(5-ethyl-2-isopropyl-1,3-thiazol-4-yl)phenoxy]pentoxy)-benzamidine,
20) N-hydroxy-4-(5-[4-(5-ethyl-2-phenyl-1,3-thiazol-4-yl)phenoxy]pentoxy)-benzamidine,
21) N-hydroxy-4-(5-[4-(5-ethyl-2-pyridin-3-yl-1,3-thiazol-4-yl)phenoxy]pentoxy)-benzamidine,
22) N-hydroxy-4-(5-[4-(2-cyclohexyl-5-ethyl-1,3-thiazol-4-yl)phenoxy]pentoxy)-benzamidine,
23) N-hydroxy-4-(5-[4-(5-ethyl-2-pentyl-1,3-thiazol-4-yl)phenoxy]pentoxy)-benzamidine, 24) N-hydroxy-4-(5-[4-(2-ethyl-5-isopropyl-1,3-thiazol-4-yl)phenoxy]pentoxy)-benzamidine,
25) N-hydroxy-4-(5-[4-(2,5-diisopropyl-1,3-thiazol-4-yl)phenoxy]pentoxy)-benzamidine,
26) N-hydroxy-4-(5-[4-(5-isopropyl-2-phenyl-1,3-thiazol-4-yl)phenoxy]pentoxy)-benzamidine,
27) N-hydroxy-4-(5-[4-(5-isopropyl-2-pyridin-3-yl-1,3-thiazol-4-yl)phenoxy]pentoxy)-benzamidine,
28) N-hydroxy-4-(5-[4-(5-isopropyl-2-pentyl-1,3-thiazol-4-yl)phenoxy]pentoxy)-benzamidine,
29) N-hydroxy-4-(5-[4-(2-methyl-5-propyl-1,3-thiazol-4-yl)phenoxy]pentoxy)-benzamidine,
30) N-hydroxy-4-(5-[4-(5-butyl-2-methyl-1,3-thiazol-4-yl)phenoxy]pentoxy)-benzamidine,
31) N-hydroxy-4-(5-[4-(5-butyl-2-ethyl-1,3-thiazol-4-yl)phenoxy]pentoxy)-benzamidine,
32) N-hydroxy-4-(5-[4-(5-butyl-2-isopropyl-1,3-thiazol-4-yl)phenoxy]pentoxy)-benzamidine,
33) N-hydroxy-4-(5-[4-(5-butyl-2-phenyl-1,3-thiazol-4-yl)phenoxy]pentoxy)-benzamidine,
34) N-hydroxy-4-(5-[4-(5-butyl-2-pyridin-3-yl-1,3-thiazol-4-yl)phenoxy]pentoxy)-benzamidine,
35) N-hydroxy-4-(5-[4-(5-butyl-2-cyclohexyl-1,3-thiazol-4-yl)phenoxy]pentoxy)-benzamidine,
36) N-hydroxy-4-(5-[4-(5-butyl-2-pentyl-1,3-thiazol-4-yl)phenoxy]pentoxy)-benzamidine,
37) N-hydroxy-4-(5-[4-(5-butyl-2-t-butyl-1,3-thiazol-4-yl)phenoxy]pentoxy)-benzamidine,
38) N-hydroxy-4-(5-[4-(5-benzyl-2-methyl-1,3-thiazol-4-yl)phenoxy]pentoxy)-benzamidine,
39) N-hydroxy-4-(5-[4-(5-benzyl-2-isopropyl-1,3-thiazol-4-yl)phenoxy]pentoxy)-benzamidine,
40) N-hydroxy-4-(5-[4-(5-benzyl-2-phenyl-1,3-thiazol-4-yl)phenoxy]pentoxy)-benzamidine,
41) N-hydroxy-4-(5-[4-(5-benzyl-2-pyridin-3-yl-1,3-thiazol-4-yl)phenoxy]pentoxy)-benzamidine,
42) N-hydroxy-4-(5-[4-(5-(2-chloro-ethyl)-2-methyl-1,3-thiazol-4-yl)phenoxy]pentoxy)-benzamidine,
43) N-hydroxy-4-(5-[4-(5-cyclopentyl-2-methyl-1,3-thiazol-4-yl)phenoxy]pentoxy)-benzamidine,
44) N-hydroxy-4-(5-[4-(5-isobutyl-2-methyl-1,3-thiazol-4-yl)phenoxy]pentoxy)-benzamidine,
45) N-hydroxy-4-(5-[4-(5-cyclopentylmethyl-2-methyl-1,3-thiazol-4-yl)phenoxy]pentoxy)-benzamidine,
46) N-hydroxy-4-(5-[4-(5-cyclopentylmethyl-2-ethyl-1,3-thiazol-4-yl)phenoxy]pentoxy)-benzamidine,
47) N-hydroxy-4-(5-[4-(5-cyclopentylnnethyl-2-isopropyl-1,3-thiazol-4-yl)phenoxy]pentoxy)-benzamidine,
48) N-hydroxy-4-(5-[4-(5-cyclopentylmethyl-2-phenyl-1,3-thiazol-4-yl)phenoxy]pentoxy)-benzamidine,
49) N-hydroxy-4-(5-[4-(5-cyclopentylmethyl-2-pyridin-3-yl-1,3-thiazol-4-yl)phenoxy]pentoxy)-benzamidine,
50) N-hydroxy-4-(5-[4-(5-cyclopentylmethyl-2-cyclohexyl-1,3-thiazol-4-yl)phenoxy]pentoxy)-benzamidine,
51) N-hydroxy-4-(5-[4-(5-cyclopentylmethyl-2-pentyl-1,3-thiazol-4-yl)phenoxy]pentoxy)-benzamidine,
52) 4-(5-[4-(2-methyl-1,3-thiazol-4-yl)phenoxy]pentoxy)-benzamidine,
53) 4-(5-[4-(2-isopropyl-1,3-thiazol-4-yl)phenoxy]pentoxy)-benzamidine,
54) 4-(5-[4-(2,5-dimethyl-1,3-thiazol-4-yl)phenoxy]pentoxy)-benzamidine,
55) 4-(5-[4-(5-ethyl-2-isopropyl-1,3-thiazol-4-yl)phenoxy]pentoxy)-benzamidine,
56) 4-(5-[4-(5-ethyl-2-phenyl-1,3-thiazol-4-yl)phenoxy]pentoxy)-benzamidine,
57) N-hydroxy-4-(5-[4-(2-amino-1,3-thiazol-4-yl)phenoxy]pentoxy)-benzamidine,
58) N-hydroxy-4-(5-[4-(2-amino-5-methyl-1,3-thiazol-4-yl)phenoxy]pentoxy)-benzamidine,
59) N-hydroxy-4-[5-(4-(2-guanidino-5-methyl-1,3-thiazol-4-yl)phenoxy)pentoxy)-benzamidine,
60) N-hydroxy-4-(5-[4-(2-amino-5-ethyl-1,3-thiazol-4-yl)phenoxy]pentoxy)-benzamidine,
61) N-hydroxy-4-(5-[4-(2-amino-5-isopropyl-1,3-thiazol-4-yl)phenoxy]pentoxy)-benzamidine,
62) N-hydroxy-4-(5-[4-(2-guanidino-5-isopropyl-1,3-thiazol-4-yl)phenoxy]pentoxy)-benzamidine,
63) N-hydroxy-4-(5-[4-(2-amino-5-butyl-1,3-thiazol-4-yl)phenoxy]pentoxy)-benzamidine,
64) N-hydroxy-4-(5-[4-(5-butyl-2-guanidino-1,3-thiazol-4-yl)phenoxy]pentoxy)-benzamidine,
65) N-hydroxy-4-(5-[4-(2-amino-5-benzyl-1,3-thiazol-4-yl)phenoxy]pentoxy)-benzamidine,
66) N-hydroxy-4-(5-[4-(5-benzyl-2-guanidino-1,3-thiazol-4-yl)phenoxy]pentoxy)-benzamidine,
67) N-hydroxy-4-(5-[4-(2-amino-5-cyclopentylmethyl-1,3-thiazol-4-yl)phenoxy]pentoxy)-benzamidine,
68) N-hydroxy-4-(5-[4-(5-cyclopentylmethyl-2-(1-propyl-piperidin-4-yl)-1,3-thiazol-4-yl)phenoxy]pentoxy)-benzamidine,
69) N-hydroxy-4-(5-[4-(2-(isobutyryl)amino-5-methyl-1,3-thiazol-4-yl)phenoxy]pentoxy)-benzamidine,
70) N-hydroxy-4-(5-[4-(5-isopropyl-2-morpholinomethyl-1,3-thiazol-4-yl)phenoxy]pentoxy)-benzamidine,
71) N-hydroxy-4-(5-[4-(2-aminomethyl-5-benzyl-1,3-thiazol-4-yl)phenoxy]pentoxy)-benzamidine,
72) N-hydroxy-4-(5-[4-(5-methyl-2-(1-propyl-piperidin-4-yl)-1,3-thiazol-4-yl)phenoxy]pentoxy)-benzamidine,
73) N-hydroxy-4-(5-[4-(5-isopropyl-2-aminomethyl-1,3-thiazol-4-yl)phenoxy]pentoxy)-benzamidine,
74) N-hydroxy-4-(5-[4-(5-vinyl-2-methyl-1,3-thiazol-4-yl)phenoxy]pentoxy)-benzamidine,
75) N-hydroxy-4-(5-[4-(5-hydroxymethyl-2-methyl-1,3-thiazol-4-yl)phenoxy]pentoxy)-benzamidine,
76) N-hydroxy-4-(5-[4-(5-methoxymethyl-2-methyl-1,3-thiazol-4-yl)phenoxy]pentoxy)-benzamidine,
77) N-hydroxy-4-(5-[4-(5-(2-chloroethyl)-2-amino-1,3-thiazol-4-yl)phenoxy]pentoxy)-benzamidine,
78) N-hydroxy-4-(5-[4-(5-vinyl-2-amino-1,3-thiazol-4-yl)phenoxy]pentoxy)-benzamidine,
79) N-hydroxy-4-(5-[4-(5-vinyl-2-(pyridin-3-yl)-1,3-thiazol-4-yl)phenoxy]pentoxy)-benzamidine,
80) N-hydroxy-4-(5-[4-(5-(2-chloroethyl)-2-(pyridin-3-yl)-1,3-thiazol-4-yl)phenoxy]pentoxy)-benzamidine,
81) N-hydroxy-4-(5-[4-(2-amino-5-cyclopentyl-1,3-thiazol-4-yl)phenoxy]pentoxy)-benzamidine,
82) N-hydroxy-4-(5-[4-(5-ethyl-2-aminomethyl-1,3-thiazol-4-yl)phenoxy]pentoxy)-benzamidine,
83) N-hydroxy-4-(5-[4-(5-isopropyl-2-(piperidin-3-yl)-1,3-thiazol-4-yl)phenoxy]pentoxy)-benzamidine,
84) N-hydroxy-4-(5-[4-(2-ethylamino-1,3-thiazol-4-yl)phenoxy]pentoxy)-benzamidine,
85) N-hydroxy-4-(5-[4-(2-ethanesulfonylamino-1,3-thiazol-4-yl)phenoxy]pentoxy)-benzamidine,
86) N-hydroxy-4-(5-[4-(5-methyl-2-methylamino-1,3-thiazol-4-yl)phenoxy]pentoxy)-benzamidine,
87) N-hydroxy-4-(5-[4-(2-ethylamino-5-methyl-1,3-thiazol-4-yl)phenoxy]pentoxy)-benzamidine,
88) N-hydroxy-4-(4-[4-(5-methyl-2-propylamino-1,3-thiazol-4-yl)phenoxy]pentoxy)-benzamidine, 89) N-hydroxy-4-(5-[4-(5-cyclopentylmethyl-2-(3-pyridylcarbonyl)amino-1,3-thiazol-4-yl)phenoxy]pentoxy)-benzamidine,
90) N-hydroxy-4-(5-[4-(2-hydroxyacetylamino-5-methyl-1,3-thiazol-4-yl)phenoxy]pentoxy)-benzamidine,
91) N-hydroxy-4-(5-[4-(5-methyl-2-(4-pyridylcarbonyl)amino-1,3-thiazol-4-yl)phenoxy]pentoxy)-benzamidine,
92) N-hydroxy-4-(5-[4-(5-methyl-2-(3-pyridylcarbonyl)amino-1,3-thiazol-4-yl)phenoxy]pentoxy)-benzamidine,
93) N-hydroxy-4-(5-[4-(2-ethanesulfonylamino-5-methyl-1,3-thiazol-4-yl)phenoxy]pentoxy)-benzamidine,
94) N-hydroxy-4-(5-(4-(2-(2-methoxyethyl)amino-5-methyl-1,3-thiazol-4-yl)phenoxy]pentoxy)-benzamidine,
95) N-hydroxy-4-(5-[4-(2-ethanesulfonylamino-5-ethyl-1,3-thiazol-4-yl)phenoxy]pentoxy)-benzamidine,
96) N-hydroxy-4-(5-[4-(5-ethyl-2-methylamino-1,3-thiazol-4-yl)phenoxy]pentoxy)-benzamidine,
97) N-hydroxy-4-(5-[4-(5-ethyl-2-ethylamino-1,3-thiazol-4-yl)phenoxy]pentoxy)-benzamidine,
98) N-hydroxy-4-(5-[4-(5-ethyl-2-propylamino-1,3-thiazol-4-yl)phenoxy]pentoxy)-benzamidine,
99) N-hydroxy-4-(5-[4-(5-ethyl-2-methoxyacetylamino-1,3-thiazol-4-yl)phenoxy]pentoxy)-benzamidine,
100) N-hydroxy-4-(5-[4-(5-ethyl-2-(4-pyridylcarbonyl)amino-1,3-thiazol-4-yl)phenoxy]pentoxy)-benzamidine,
101) N-hydroxy-4-(5-[4-(5-ethyl-2-(3-pyridylcarbonyl)amino-1,3-thiazol-4-yl)phenoxy]pentoxy)-benzamidine,
102) N-hydroxy-4-(5-[4-(5-ethyl-2-(2-methoxyethyl)amino-1,3-thiazol-4-yl)phenoxy]pentoxy)-benzamidine,
103) N-hydroxy-4-(5-[4-(5-isopropyl-2-methylamino-1,3-thiazol-4-yl)phenoxy]pentoxy)-benzamidine,
104) N-hydroxy-4-(5-[4-(2-ethylamino-5-isopropyl-1,3-thiazol-4-yl)phenoxy]pentoxy)-benzamidine,
105) N-hydroxy-4-(5-[4-(5-butyl-2-methylamino-1,3-thiazol-4-yl)phenoxy]pentoxy)-benzamidine,
106) N-hydroxy-4-(5-[4-(5-butyl-2-ethylamino-1,3-thiazol-4-yl)phenoxy]pentoxy)-benzamidine,
107) N-hydroxy-4-(5-[4-(5-benzyl-2-methylamino-1,3-thiazol-4-yl)phenoxy]pentoxy)-benzamidine,
108) N-hydroxy-4-(5-[4-(5-benzyl-2-ethylamino-1,3-thiazol-4-yl)phenoxy]pentoxy)-benzamidine,
109) N-hydroxy-4-(5-[4-(5-cyclopentylmethyl-2-methylamino-1,3-thiazol-4-yl)phenoxy]pentoxy)-benzamidine,
110) N-hydroxy-4-(5-[4-(5-cyclopentylmethyl-2-ethylamino-1,3-thiazol-4-yl)phenoxy]pentoxy)-benzamidine,
111) N-hydroxy-4-(5-[4-(5-cyclopentylmethyl-2-propylamino-1,3-thiazol-4-yl)phenoxy]pentoxy)-benzamidine,
112) N-hydroxy-4-(5-[4-(5-cyclopentylmethyl-2-(4-pyridylcarbonyl)amino-1,3-thiazol-4-yl)phenoxy]pentoxy)-benzamidine,
113) N-hydroxy-4-(5-[4-(5-cyclopentyl-2-propylamino-1,3-thiazol-4-yl)phenoxy]pentoxy)-benzamidine,
114) N-hydroxy-4-(5-[4-(5-isopropyl-2-[(pyridin-3-yl-methyl)amino]-1,3-thiazol-4-yl)phenoxy]pentoxy)-benzamidine,
115) N-hydroxy-4-(5-[4-(5-(2-chloroethyl)-2-methylamino-1,3-thiazol-4-yl)phenoxy]pentoxy)-benzamidine,
116) N-hydroxy-4-(5-[4-(2-methylamino-1,3-thiazol-4-yl)phenoxy]pentoxy)-benzamidine,
117) N-hydroxy-4-(5-[4-(5-ethyl-2-[(pyridin-3-yl-methyl)amino-1,3-thiazol-4-yl)phenoxy]pentoxy)-benzamidine,
118) N-hydroxy-4-(5-[4-(2-(ethanesulfonyl-methyl-amino)-1,3-thiazol-4-yl)phenoxy]pentoxy)-benzamidine,
119) N-hydroxy-4-(5-[4-(2-methyl-(2-morpholinoethyl)amino-1,3-thiazol-4-yl)phenoxy]pentoxy)-benzamidine,
120) N-hydroxy-4-(5-[4-(2-(2-hydroxyethyl)-methylamino-5-methyl-1,3-thiazol-4-yl)phenoxy]pentoxy)-benzamidine,
121) N-hydroxy-4-(5-[4-(2-(ethyl-(2-hydroxyethyl)-amino)-5-methyl-1,3-thiazol-4-yl)phenoxy]pentoxy)-benzamidine,
122) N-hydroxy-4-(5-[4-(2-(bis-(2-methoxyethyl)-amino)-5-methyl-1,3-thiazol-4-yl)phenoxy]pentoxy)-benzamidine,
123) N-hydroxy-4-(5-[4-(5-methyl-2-(methyl-(2-morpholinoethyl)-amino)-1,3-thiazol-4-yl)phenoxy]pentoxy)-benzamidine,
124) N-hydroxy-4-(5-[4-(2-(ethyl-1-(2-morpholinoethyl)-amino)-5-methyl-1,3-thiazol-4-yl)phenoxy]pentoxy)-benzamidine,
125) N-hydroxy-4-(5-[4-(2-(benzyl-methyl-amino)-5-methyl-1,3-thiazol-4-yl)phenoxy]pentoxy)-benzamidine,
126) N-hydroxy-4-(5-[4-(5-methyl-2-(methyl-pyridin-3-yl-methyl-amino)-1,3-thiazol-4-yl)phenoxy]pentoxy)-benzamidine,
127) N-hydroxy-4-(5-[4-(2-(benzyl-ethyl-amino)-5-methyl-1,3-thiazol-4-yl)phenoxy]pentoxy)-benzamidine,
128) N-hydroxy-4-(5-[4-(2-(bis-(2-hydroxyethyl)-amino)-5-methyl-1,3-thiazol-4-yl)phenoxy]pentoxy)-benzamidine,
129) N-hydroxy-4-(5-[4-(5-ethyl-2-((2-hydroxyethyl)-methyl-amino)-1,3-thiazol-4-yl)phenoxy]pentoxy)-benzamidine,
130) N-hydroxy-4-(5-[4-(5-ethyl-2-(ethyl-(2-hydroxyethyl)-amino)-1,3-thiazol-4-yl)phenoxy]pentoxy)-benzamidine,
131) N-hydroxy-4-(5-[4-(5-ethyl-2-(methyl-(2-morpholinoethyl)-amino)-1,3-thiazol-4-yl)phenoxy]pentoxy)-benzamidine,
132) N-hydroxy-4-(5-[4-(5-ethyl-2-(ethyl-(2-morpholinoethyl)-amino)-1,3-thiazol-4-yl)phenoxy]pentoxy)-benzamidine,
133) N-hydroxy-4-(5-[4-(2-(benzyl-methyl-amino)-5-ethyl-1,3-thiazol-4-yl)phenoxy]pentoxy)-benzamidine,
134) N-hydroxy-4-(5-[4-(5-ethyl-2-(methyl-(pyridin-3-yl-methyl)amino)-1,3-thiazol-4-yl)phenoxy]pentoxy)-benzamidine,
135) N-hydroxy-4-(5-[4-(2-(benzyl-ethyl-amino)-5-ethyl-1,3-thiazol-4-yl)phenoxy]pentoxy)-benzamidine,
136) N-hydroxy-4-(5-[4-(5-ethyl-2-(ethyl-(pyridin-3-yl-methyl)amino)-1,3-thiazol-4-yl)phenoxy]pentoxy)-benzamidine,
137) N-hydroxy-4-(5-[(4-(2-(bis-(pyridin-3-yl-methyl)amino)-5-ethyl-1,3-thiazol-4-yl)phenoxy]pentoxy-benzamidine,
138) N-hydroxy-4-(5-[4-(2-dipropylamino-5-ethyl-1,3-thiazol-4-yl)phenoxy]pentoxy)-benzamidine,
139) N-hydroxy-4-(5-[4-(2-(bis-(2-hydroxyethyl)amino)-5-ethyl-1,3-thiazol-4-yl)phenoxy]pentoxy)-benzamidine,
140) N-hydroxy-4-(5-[4-(2-((2-hydroxyethyl)-methylamino)-5-isopropyl-1,3-thiazol-4-yl)phenoxy]pentoxy)-benzamidine,
141) N-hydroxy-4-(5-[4-(5-isopropyl-2-(methyl-(pyridin-3-yl-methyl)amino)-1,3-thiazol-4-yl)phenoxy]pentoxy)-benzamidine,
142) N-hydroxy-4-(5-[4-(2-(ethanesulfonyl-methyl-amino)-5-isopropyl-1,3-thiazol-4-yl)phenoxy]pentoxy)-benzamidine,
143) N-hydroxy-4-(5-[4-(5-butyl-2-((2-hydroxyethyl)-methyl-amino)-1,3-thiazol-4-yl)phenoxy]pentoxy)-benzamidine, 144) N-hydroxy-4-(5-[4-(5-butyl-2-(methyl-(2-morpholino-ethyl)amino)-1,3-thiazol-4-yl)phenoxy]pentoxy)-benzamidine,
145) N-hydroxy-4-(5-[4-(5-butyl-2-(methyl-(pyridin-3-yl-methyl)amino)-1,3-thiazol-4-yl)phenoxy]pentoxy)-benzamidine,
146) N-hydroxy-4-(5-[4-(5-butyl-2-dipropylamino-1,3-thiazol-4-yl)phenoxy]pentoxy)-benzamidine,
147) N-hydroxy-4-(5-[4-(5-cyclopentylmethyl-2-(methyl-(pyridin-3-yl-methyl)amino)-1,3-thiazol-4-yl)phenoxy]pentoxy)-benzamidine,
148) N-hydroxy-4-(5-[4-(5-cyclopentylmethyl-2-(methyl-(2-morpholinoethyl)amino)-1,3-thiazol-4-yl)phenoxy]pentoxy)-benzamidine,
149) N-hydroxy-4-(5-[4-(5-cyclopentylmethyl-2-dipropylamino-1,3-thiazol-4-yl)phenoxy]pentoxy)-benzamidine,
150) N-hydroxy-4-(5-[4-(5-butyl-2-diethylamino-1,3-thiazol-4-yl)phenoxy]pentoxy)-benzamidine,
151) N-hydroxy-4-(5-[4-(5-butyl-2-ethylmethylamino-1,3-thiazol-4-yl)phenoxy]pentoxy)-benzamidine,
152) N-hydroxy-4-(5-[4-(5-butyl-2-dimethylamino-1,3-thiazol-4-yl)phenoxy]pentoxy)-benzamidine,
153) N-hydroxy-4-(5-[4-(5-cyclopentyl-2-[methyl-(2-morpholinoethyl)amino]-1,3-thiazol-4-yl)phenoxy]pentoxy)-benzamidine,
154) N-hydroxy-4-(5-[4-(5-isobutyl-2-[methyl-(2-morpholinoethyl)amino]-1,3-thiazol-4-yl)phenoxy]pentoxy)-benzamidine,
155) N-hydroxy-4-(5-[4-(5-(2-chloroethyl)-2-dimethylamino-1,3-thiazol-4-yl)phenoxy]pentoxy)-benzamidine,
156) N-hydroxy-4-(5-[4-(5-cyclopentyl-2-diethylamino-1,3-thiazol-4-yl)phenoxy]pentoxy)-benzamidine,
157) N-hydroxy-4-(5-[4-(5-isopropyl-2-dipropylamino-1,3-thiazol-4-yl)phenoxy]pentoxy)-benzamidine,
158) N-hydroxy-4-(5-[4-(5-ethyl-2-diethylamino-1,3-thiazol-4-yl)phenoxy]pentoxy)-benzamidine,
159) N-hydroxy-4-(5-[4-(5-isopropyl-2-[methyl-(2-morpholinoethyl)amino]-1,3-thiazol-4-yl)phenoxy]pentoxy)-benzamidine,
160) N-hydroxy-4-(5-[4-(5-cyclopentylmethyl-2-diethylamino-1,3-thiazol-4-yl)phenoxy]pentoxy)-benzamidine,
161) N-hydroxy-4-(5-[4-(5-isopropyl-2-dimethylamino-1,3-thiazol-4-yl)phenoxy]pentoxy)-benzamidine,
162) N-hydroxy-4-(5-[4-(5-isopropyl-2-diethylamino-1,3-thiazol-4-yl)phenoxy]pentoxy)-benzamidine,
163) N-hydroxy-4-(5-[4-(5-cyclopentylmethyl-2-dimethylamino-1,3-thiazol-4-yl)phenoxy]pentoxy)-benzamidine,
164) N-hydroxy-4-(5-[4-(5-methyl-2-piperdino-1,3-thiazol-4-yl)phenoxy]pentoxy)-benzamidine,
165) N-hydroxy-4-(5-[4-(5-methyl-2-morpholino-1,3-thiazol-4-yl)phenoxy]pentoxy)-benzamidine,
166) N-hydroxy-4-(5-[4-(5-ethyl-2-piperdino-1,3-thiazol-4-yl)phenoxy]pentoxy)-benzamidine,
167) N-hydroxy-4-(5-[4-(5-cyclopentylmethyl-2-piperdino-1,3-thiazol-4-yl)phenoxy]pentoxy)-benzamidine,
168) N-hydroxy-4-(5-[4-(5-cyclopentylmethyl-2-morpholino-1,3-thiazol-4-yl)phenoxy]pentoxy)-benzamidine,
169) N-hydroxy-4-(5-[4-(5-isopropyl-2-morpholino-1,3-thiazol-4-yl)phenoxy]pentoxy)-benzamidine,
170) N-hydroxy-4-(5-(4-[5-cyclopentylmethyl-2-(4-methylpiperazino)-1,3-thiazol-4-yl]phenoxy)-pentoxy)-benzamidine,
171) N-hydroxy-4-(5-[4-(5-vinyl-2-morpholin-4-yl-1,3-thiazol-4-yl)phenoxy]pentoxy)-benzamidine,
172) N-hydroxy-4-(5-[4-(5-cyclopentyl-2-morpholin-4-yl-1,3-thiazol-4-yl)phenoxy]pentoxy)-benzamidine,
173) N-hydroxy-4-[5-[4-(5-isobutyl-2-morpholin-4-yl-1,3-thiazol-4-yl)phenoxy]pentoxy)-benzamidine,
174) N-hydroxy-4-(5-[4-(5-ethyl-2-(4-methylpiperazino)-1,3-thiazol-4-yl]phenoxy)-pentoxy)-benzamidine,
175) N-hydroxy-4-(5-[4-(2-morpholin-4-yl-1,3-thiazol-4-yl)phenoxy]pentoxy)-benzamidine,
176) N-hydroxy-4-(5-(4-[5-isopropyl-2-(4-methylpiperazino)-1,3-thiazol-4-yl]phenoxy)-pentoxy)-benzamidine,
177) N-hydroxy-4-(5-[4-(5-isopropyl-2-methyl-1,3-thiazol-4-yl)phenoxy]-pentylamino)-benzamidine,
178) N-hydroxy-4-(2-[2-(4-(5-isopropyl-2-methyl-1,3-thiazol-4-yl)phenoxy)-ethoxy]-ethoxy)-benzamidine,
179) N-hydroxy-4-(3-hydroxy-5-[4-(5-isopropyl-2-methyl-1,3-thiazol-4-yl)-phenoxy]-3-methyl-pentoxy)-benzamidine,
180) N-hydroxy-4-(2-[2-(4-(5-isopropyl-2-methyl-1,3-thiazol-4-yl)-phenoxy)-1-methyl-ethylamino]-ethoxy)-benzamidine,
181) N-hydroxy-4-(3-[4-(3-(4-(5-isopropyl-2-methyl-1,3-thiazol-4-yl)-phenoxy)-propyl)-piperazin-1-yl]-propoxy)-benzamidine,
182) N-hydroxy-4-(5-[4-(5-isopropyl-2-methyl-1,3-thiazol-4-yl)-phenoxy]-pentanoyl-amino)-benzamidine,
183) N-hydroxy-4-(5-[4-(5-isopropyl-2-methyl-1,3-thiazol-4-yl)-phenoxy]-pentyl-methyl-amino)-benzamidine,
184) N-hydroxy-4-(4-[4-(5-isopropyl-2-methyl-1,3-thiazol-4-yl)-phenoxy]-2-butenyloxy)-benzamidine,
185) N-hydroxy-4-(4-[4-(5-isopropyl-2-methyl-1,3-thiazol-4-yl)-phenoxymethyl]-benzyloxy)-benzamidine,
186) N-hydroxy-4-(2-[2-(4-(5-isopropyl-2-methyl-1,3-thiazol-4-yl)phenoxy)-ethylamino]-ethoxy)-benzamidine,
187) N-hydroxy-2-fluoro-4-(5-[4-(5-isopropyl-2-methyl-1,3-thiazol-4-yl)-phenoxy]-pentoxy)-benzamidine,
188) 2,N-dihydroxy-4-(5-[4-(5-isopropyl-2-methyl-1,3-thiazol-4-yl)-phenoxy]-pentoxy)-benzamidine,
189) N-hydroxy-4-(5-[4-(5-isopropyl-2-methyl-1,3-thiazol-4-yl)-phenoxy]-pentoxy-3-methoxy)-benzamidine,
190) N-hydroxy-2-cyclohexylamino-4-(5-[4-(5-isopropyl-2-methyl-1,3-thiazol-4-yl)-phenoxy]-pentoxy)-benzamidine,
191) N-hydroxy-4-(5-[3-fluoro-4-(5-isopropyl-2-methyl-1,3-thiazol-4-yl)-phenoxy]-pentoxy)-benzamidine,
192) N-hydroxy-2-fluoro-4-(5-[3-fluoro-4-(5-isopropyl-2-methyl-1,3-thiazol-4-yl)-phenoxy]-pentoxy)-benzamidine,
193) N-hydroxy-4-(3-[4-(5-isopropyl-2-methyl-1,3-thiazol-4-yl)phenoxy]propoxy)-benzamidine,
194) N-hydroxy-4-(4-[4-(5-isopropyl-2-methyl-1,3-thiazol-4-yl)phenoxy]butoxy)-benzamidine,
195) N-hydroxy-3-(5-[4-(5-isopropyl-2-methyl-thiazol-4-yl)-phenoxy]-pentylamino)-benzamidine,
196) N-hydroxy-4-(4-[4-(2-cyclohexyl-5-ethyl-thiazol-4-yl)-phenoxy]-butoxy)-benzamidine,
197) N-hydroxy-4-(3-[4-(5-ethyl-2-[(2-hydroxyethyl)-methyl-amino]-thiazol-4-yl)phenoxy]propoxy)-benzamidine,
198) N-hydroxy-4-(4-[4-(5-ethyl-2-[(2-hydroxyethyl)-methyl-amino]-thiazol-4-yl)phenoxy]butoxy)-benzamidine,
199) N-hydroxy-4-(3-[4-(5-ethyl-2-[methyl-(pyridin-3-yl-methyl)amino]-thiazol-4-yl)phenoxy]propoxy)-benzamidine,
200) N-hydroxy-4-(4-[4-(5-ethyl-2-[methyl-(pyridin-3-yl-methyl)amino]-thiazol-4-yl)phenoxy]butoxy)-benzamidine
201) N-hydroxy-4-(4-[4-(5-cyclopentylmethyl-2-isopropyl-thiazol-4-yl)-phenoxymethyl]-benzyloxy)-benzamidine, 202) N-hydroxy-4-(4-[4-(5-butyl-2-isopropyl-thiazol-4-yl)-phenoxymethyl]-benzyloxy)-benzamidine,
203) N-hydroxy-4-(4-[4-(5-cyclopentylnnethyl-2-amino-thiazol-4-yl)-phenoxymethyl]-benzyloxy)-benzamidine,
204) N-hydroxy-4-(4-[4-(5-cyclopentylmethyl-2-amino-thiazol-4-yl)-phenoxymethyl]-benzyloxy-2-fluoro)-benzamidine,
205) N-hydroxy-4-(4-[4-(2-methylamino-thiazol-4-yl)-phenoxymethyl]-benzyloxy)-benzamidine,
206) N-hydroxy-4-(6-[4-(5-isopropyl-2-methyl-thiazol-4-yl)-phenoxymethyl]-pyridin-2-yl-methoxy)-benzamidine,
207) N-hydroxy-2-fluoro-4-(5-[4-(5-isopropyl-2-methyl-thiazol-4-yl)-phenoxy]-butoxy)-benzamidine,
208) N-hydroxy-4-(2-[4-(5-isopropyl-2-methyl-thiazol-4-yl)-phenoxymethyl]-benzyloxy)-benzamidine,
209) N-hydroxy-4-(3-[4-(5-isopropyl-2-methyl-thiazol-4-yl)-phenoxymethyl]-benzyloxy)-benzamidine,
210) N-hydroxy-4-(4-[4-(5-cyclopentylmethyl-2-cyclohexyl-thiazol-4-yl)-phenoxymethyl]-benzyloxy)-benzamidine,
211) N-hydroxy-4-(6-[4-(5-isopropyl-2-methyl-thiazol-4-yl)phenoxy]-hexyloxy)-benzamidine,
212) N-hydroxy-4-(5-[2-ethyl-5-hydroxy-4-(2-methyl-thiazol-4-yl)phenoxy]-pentyloxy)-benzamidine,
213) N-hydroxy-4-(5-[2-ethyl-4-(2-methyl-thiazol-4-yl)-5-propoxy-phenoxy]-pentyloxy)-benzamidine.

The benzamidine derivatives of the formula 1 may be used in the form of pharmaceutically acceptable salts known in the art. Preferable are acid addition salts prepared with pharmaceutically acceptable free acids. Free acids suitable for use in the present invention may be inorganic acids or organic acids. Examples of the inorganic acids include hydrochloric acid, bromic acid, sulfuric acid, phosphoric acid, etc, and the organic acids may be exemplified by citric acid, acetic acid, lactic acid, tartaric acid, fumaric acid, formic acid, propionic acid, oxalic acid, trifluoroacetic acid, methane sulfonic acid, benzene sulfonic acid, maleic acid, maleinic acid, benzoic acid, gluconic acid, glycolic acid, succinic acid, 4-morpholine ethane sulfonic acid, camphorsulfonic acid, 4-nitrobenzene sulfonic acid, hydroxy-O-sulfonic acid, 4-toluene sulfonic acid, galacturonic acid, embonic acid, glutamic acid, aspartic acid, etc. Preferably, hydrochloric acid as inorganic acid and methane sulfonic acid as organic acid can be used.

General definitions of substituted groups of the formula 1 have the following meanings:

Halogen means halogen group atoms including chlorine, fluorine, bromine, iodine, etc.

Alkyl radical means saturated carbohydrogens which have 1 to 6 carbon atoms and are straight or branched, for example, methyl, ethyl, n-propyl, iso-propyl, n-butyl, sec-butyl, tert-butyl, etc.

Alkoxy radical means said alkyl radical linked to oxygen, for example, methoxy, ethoxy, propoxy, iso-propoxy, butoxy, sec-butoxy, tert-butoxy, etc.

Cycloalkyl radical means nonaromatic carbohydrogen ring(s) which have 3 to 6 carbon atoms on the each ring, for example, cyclopropyl, cyclobutyl, cyclopentyl, cyclohexyl, etc.

Alkenyl radical means unsaturated carbohydrogens which have 2 to 6 carbon atoms with one or more double bonds.

Alkanoyloxy radical means oxygen-containing radical in which a terminal carbon atom of alkyl radical is substituted by carbonyl radical.

Alkenoyloxy radical means oxygen-containing radical in which a terminal carbon atom of alkenyl radical is substituted by carbonyl radical.

Alkenyloxy radical means oxygen-containing alkenyl groups.

Alkylene radical means carbohydrogen radicals which have 1 to 7 carbon atoms and 2 or more junction centers for covalent bond, including methylene, ethylene, methylethylene, isopropylidene, etc.

Alkenylene radical means carbohydrogen radicals which have 2 to 7 carbon atoms, 2 or more conjunction centers for covalent bond and 1 or more double bonds, including 1,1-vinylidene ($CH_2$=C), 1,2-vinylidene (—CH=CH—), 1,4-butadienyl (—CH=CH—CH=CH, etc.

Carbonyl radical means carbon radicals in which 2 of 4 covalent bonds are linked to oxygen atom.

In another aspect, the present invention provides a method of preparing benzamidine derivatives of the formula 1 below:

If $R_1$ is $C_1$~$C_6$ alkyl; pyridine-substituted $C_1$~$C_6$ alkyl; $C_3$~$C_6$ cycloalkyl; benzyl; phenyl; amino; guanidino; pyridinyl; pyridinyl which is substituted by $C_1$~$C_6$ alkyl; or

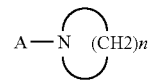

(A is $C_1$~$C_6$ alkyl and n is integer of 2 to 6), benzamidine derivatives of the formula 1 can be prepared with Reaction Scheme 1 below comprising the steps of:

1) reacting a compound of the formula 2 with a compound of the formula 3 in the presence of inorganic base to prepare a compound of the formula 4, 2) reacting a compound of the formula 5 with acid chloride of the formula 6 in the presence of inorganic acid to prepare phenone of the formula 7, and reacting the phenone of the formula 7 with acid to prepare a compound of the formula 8, 3) reacting the compound of the formula 4 prepared in step 1) with the compound of the formula 8 prepared in step 2) in the presence of inorganic base to prepare benzonitrile derivatives of the formula 9, 4) reacting the compound of the formula 9 prepared in step 3) with brominating agent to prepare α-brominated compound of the formula 10, 5) reacting α-brominated compound of the formula 10 prepared in step 4) with thioamide compound of the formula 11 to prepare benzonitrile derivatives with thiazole ring of the formula 12, and 6) reacting the compound of the formula 12 prepared in step 5) with amine compound to prepare benzamidine derivatives of the formula 1a.

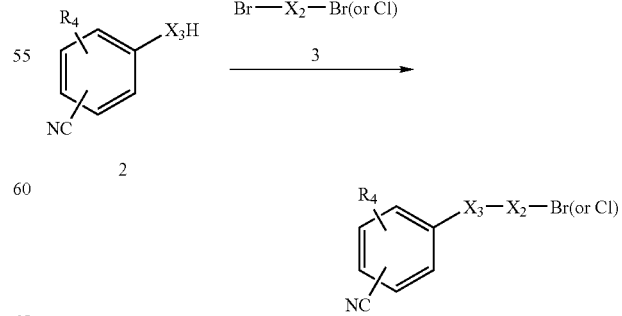

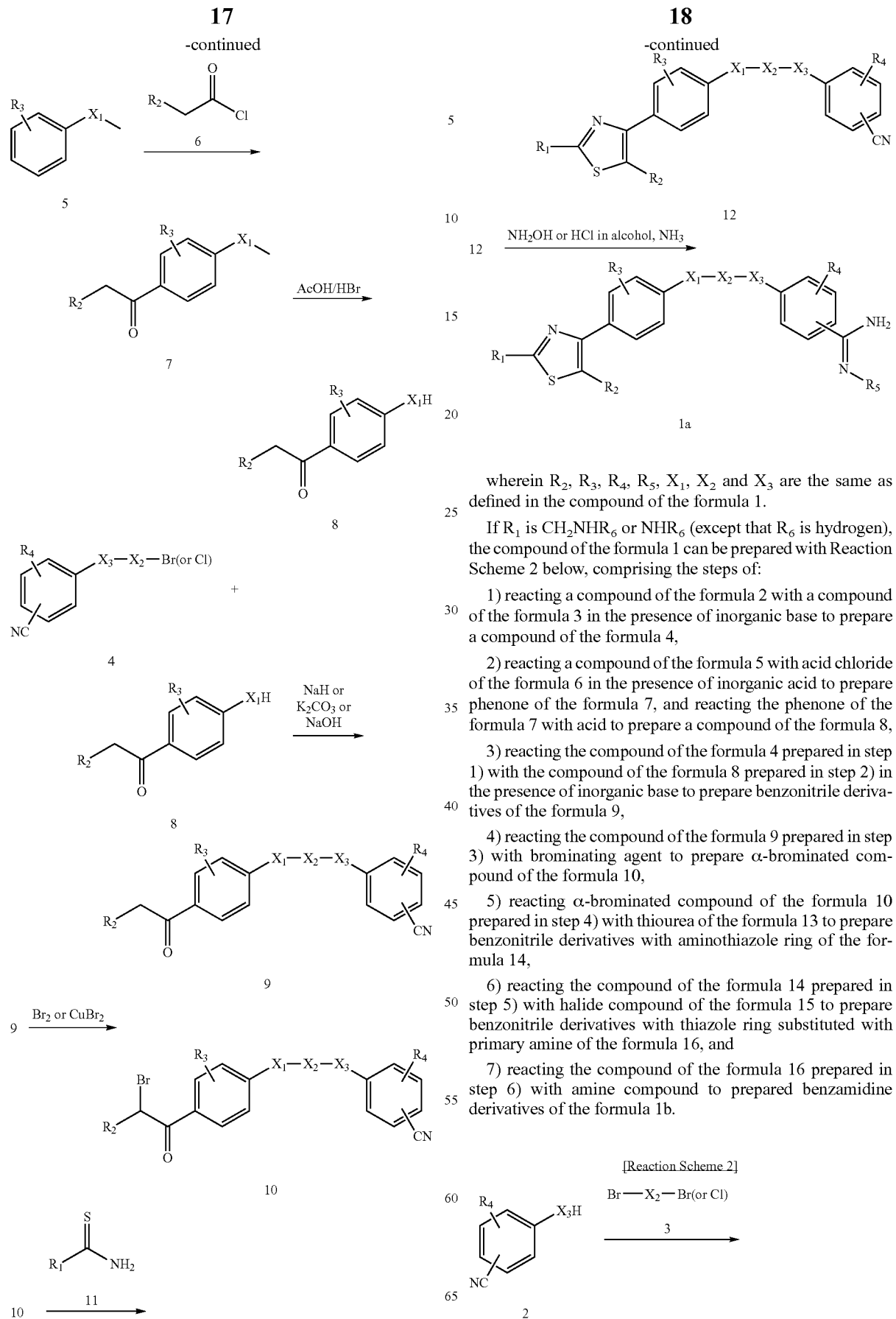

wherein $R_2$, $R_3$, $R_4$, $R_5$, $X_1$, $X_2$ and $X_3$ are the same as defined in the compound of the formula 1.

If $R_1$ is $CH_2NHR_6$ or $NHR_6$ (except that $R_6$ is hydrogen), the compound of the formula 1 can be prepared with Reaction Scheme 2 below, comprising the steps of:

1) reacting a compound of the formula 2 with a compound of the formula 3 in the presence of inorganic base to prepare a compound of the formula 4, 2) reacting a compound of the formula 5 with acid chloride of the formula 6 in the presence of inorganic acid to prepare phenone of the formula 7, and reacting the phenone of the formula 7 with acid to prepare a compound of the formula 8, 3) reacting the compound of the formula 4 prepared in step 1) with the compound of the formula 8 prepared in step 2) in the presence of inorganic base to prepare benzonitrile derivatives of the formula 9, 4) reacting the compound of the formula 9 prepared in step 3) with brominating agent to prepare α-brominated compound of the formula 10, 5) reacting α-brominated compound of the formula 10 prepared in step 4) with thiourea of the formula 13 to prepare benzonitrile derivatives with aminothiazole ring of the formula 14, 6) reacting the compound of the formula 14 prepared in step 5) with halide compound of the formula 15 to prepare benzonitrile derivatives with thiazole ring substituted with primary amine of the formula 16, and 7) reacting the compound of the formula 16 prepared in step 6) with amine compound to prepared benzamidine derivatives of the formula 1b.

[Reaction Scheme 2]

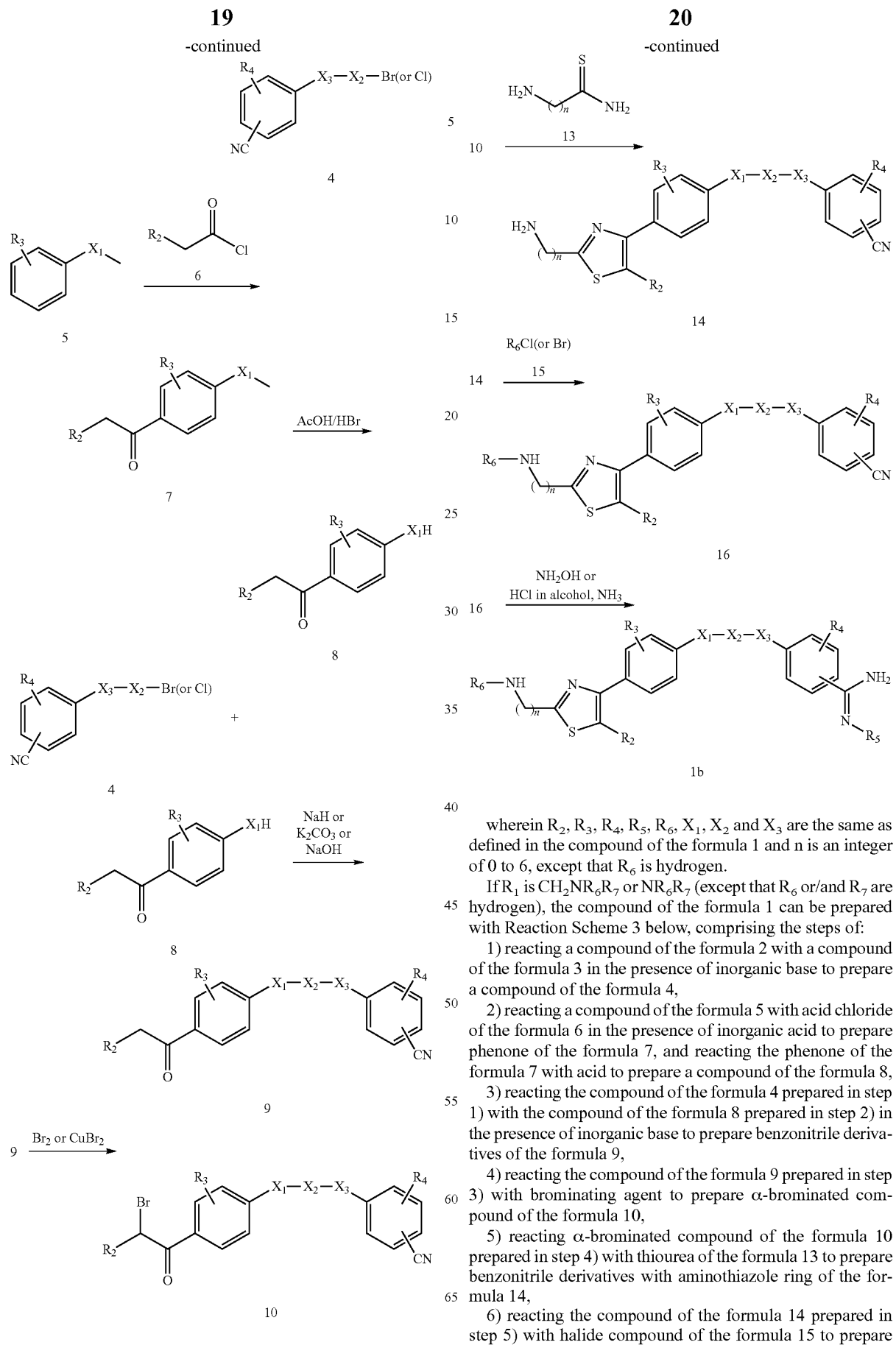

wherein $R_2$, $R_3$, $R_4$, $R_5$, $R_6$, $X_1$, $X_2$ and $X_3$ are the same as defined in the compound of the formula 1 and n is an integer of 0 to 6, except that $R_6$ is hydrogen.

If $R_1$ is $CH_2NR_6R_7$ or $NR_6R_7$ (except that $R_6$ or/and $R_7$ are hydrogen), the compound of the formula 1 can be prepared with Reaction Scheme 3 below, comprising the steps of:

1) reacting a compound of the formula 2 with a compound of the formula 3 in the presence of inorganic base to prepare a compound of the formula 4, 2) reacting a compound of the formula 5 with acid chloride of the formula 6 in the presence of inorganic acid to prepare phenone of the formula 7, and reacting the phenone of the formula 7 with acid to prepare a compound of the formula 8, 3) reacting the compound of the formula 4 prepared in step 1) with the compound of the formula 8 prepared in step 2) in the presence of inorganic base to prepare benzonitrile derivatives of the formula 9, 4) reacting the compound of the formula 9 prepared in step 3) with brominating agent to prepare α-brominated compound of the formula 10, 5) reacting α-brominated compound of the formula 10 prepared in step 4) with thiourea of the formula 13 to prepare benzonitrile derivatives with aminothiazole ring of the formula 14, 6) reacting the compound of the formula 14 prepared in step 5) with halide compound of the formula 15 to prepare benzonitrile derivatives with thiazole ring substituted with primary amine of the formula 16, 7) reacting the compound of the formula 16 prepared in step 6) above with a compound of the formula 17 to prepare benzonitrile derivatives with thiazole ring substituted with secondary amine of the formula 18, and 8) reacting the compound of the formula 18 prepared in step 7) with amine compound to prepare benzamidine derivatives of the formula 1c.

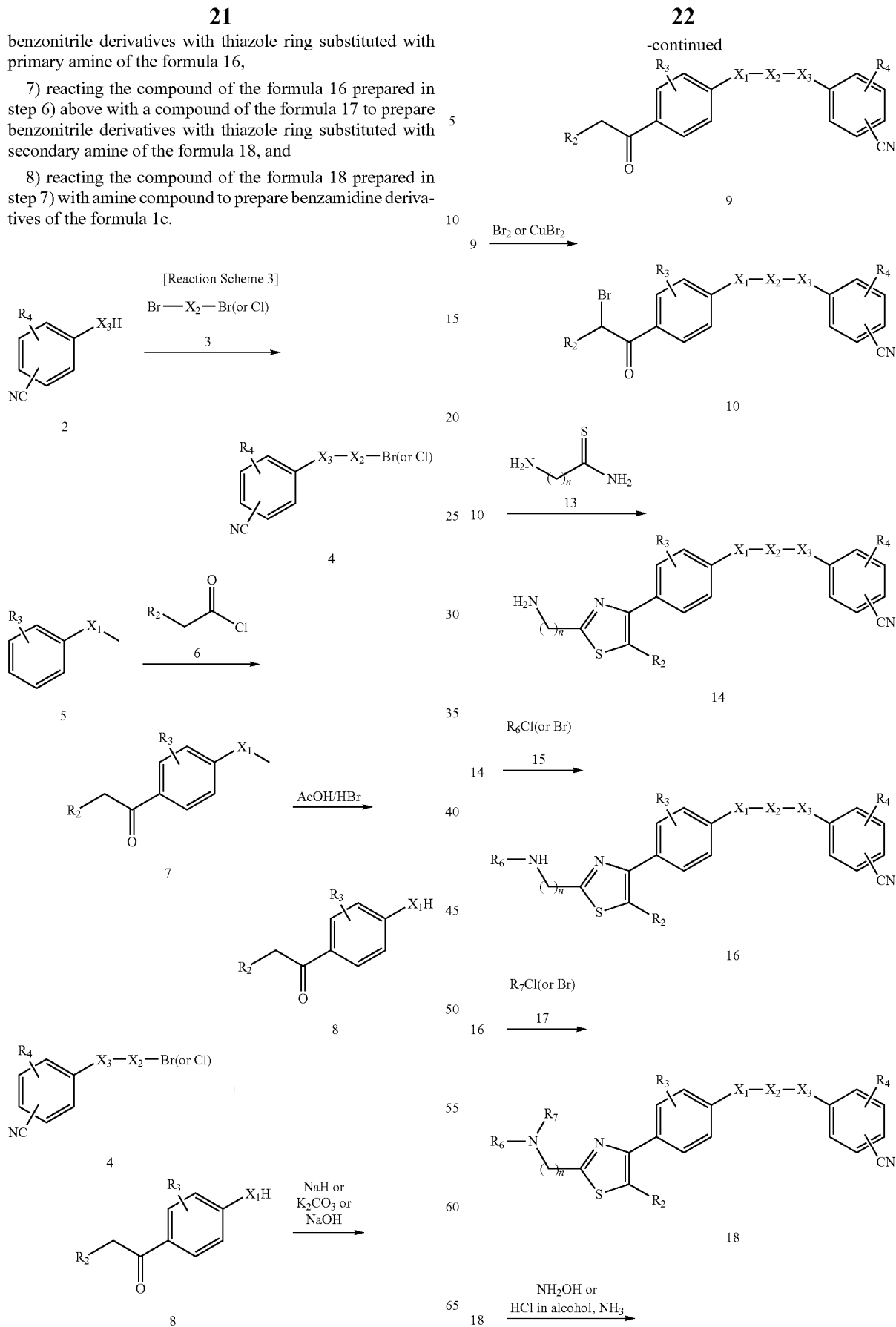

-continued

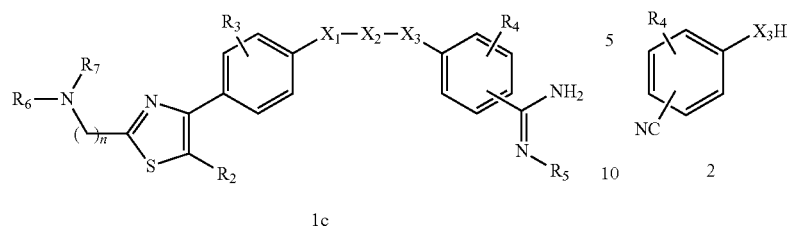

1c wherein $R_2$, $R_3$, $R_4$, $R_5$, $R_6$, $R_7$, $X_1$, $X_2$ and $X_3$ are the same as defined in the compound of the formula 1 and n is an integer of 0 to 6, except that $R_6/R_7$ are hydrogen.

If $R_1$ is

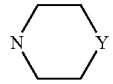

or $C_1 \sim C_6$ alkyl radical substituted by

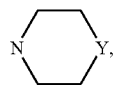

the compound of the Formula 1 can be prepared with Reaction Scheme 4 below, comprising the steps of:

1) reacting a compound of the formula 2 with a compound of the formula 3 in the presence of inorganic base to prepare a compound of the formula 4, 2) reacting a compound of the formula 5 with acid chloride of the formula 6 in the presence of inorganic acid to prepare phenone of the formula 7, and reacting the phenone of the formula 7 with acid to prepare a compound of the formula 8, 3) reacting the compound of the formula 4 prepared in step 1) with the compound of the formula 8 prepared in step 2) in the presence of inorganic base to prepare benzonitrile derivatives of the formula 9, 4) reacting the compound of the formula 9 prepared in step 3) with brominating agent to prepare α-brominated compound of the formula 10, 5) reacting α-brominated compound of the formula 10 prepared in step 4) with thiourea of the formula 13 to prepare benzonitrile derivatives with aminothiazole ring of the formula 14, 6) reacting the compound of the formula 14 prepared in step 5) with the compound of which both terminals are halogenated of the formula 19 to prepare benzonitrile derivatives with thiazole ring substituted with hetero atom ring of the formula 20, and 7) reacting the compound of the formula 20 prepared in step 6) with amine compound to prepare benzamidine derivatives of the formula 1d.

[Reaction Scheme 4]

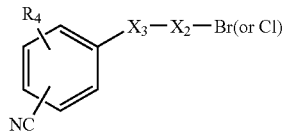

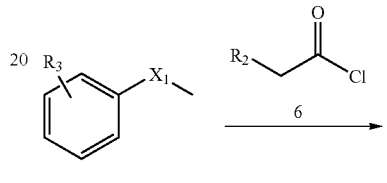

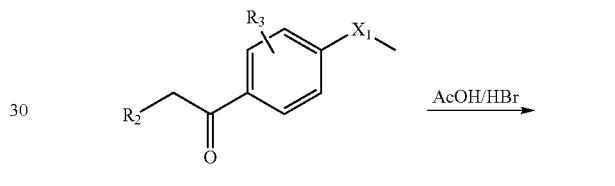

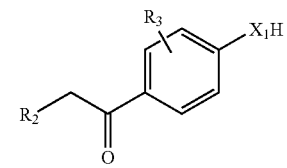

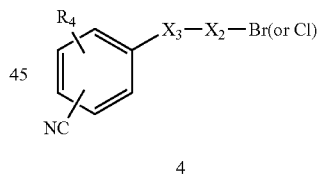

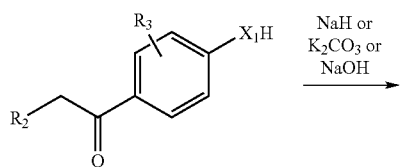

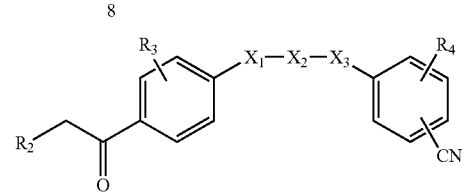

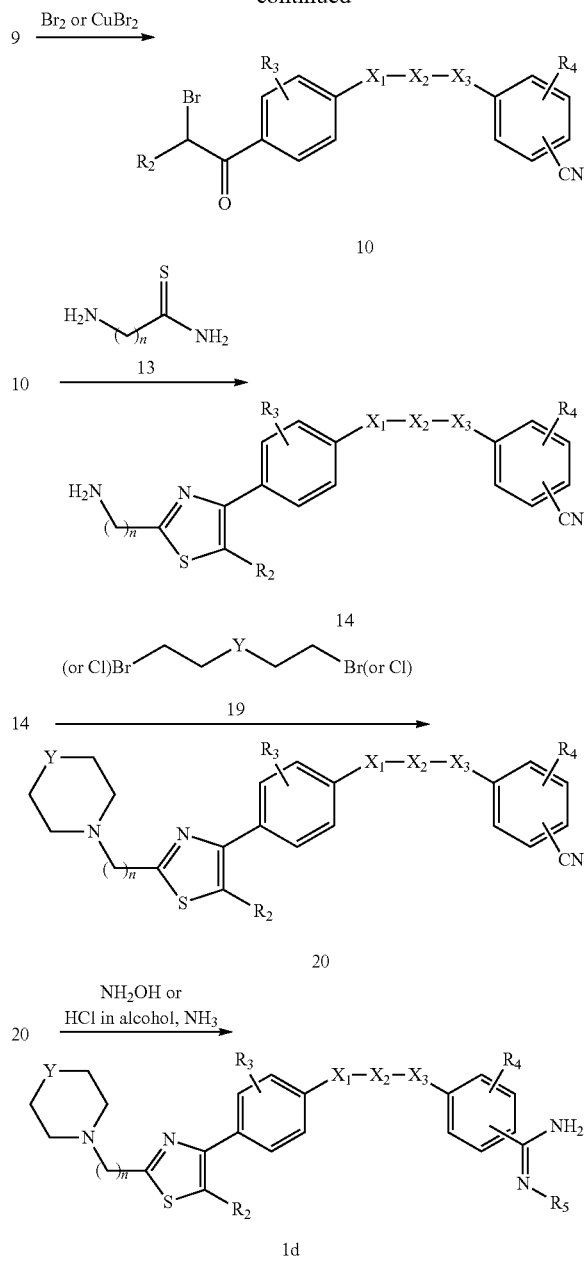

(4). The reaction temperature is preferably maintained in the range of 10 to 90° C., for 1 to 9 hours and the reaction solvent is acetonitrile, dimethylformamide, etc. To ensure that the above reaction occurs under a basic condition, an inorganic basic compound such as potassium carbonate, sodium hydroxide, sodium hydride, etc, may be used.

In step 1-2, anisole (5; $R_3$=H, $X_1$=O) is reacted with propionyl chloride (6; $R_2$=$CH_3$) in the presence of inorganic acid to afford phenone compound (7) and phenone compound (7) is consequently reacted in acidic condition to afford phenol compound (8). Acid chloride (6) used for preparing compound (7) is a material to introduce substituent $R_2$ into the compound of the formula 1 and can be selected from acid chlorides with proper alkyl radical according to the type of substituents. These acid chloride (6) includes acetyl chloride, propionyl chloride, butyryl chloride, valeryl chloride, isovaleryl chloride, 4-methylvaleryl chloride, 3-methylvaleryl chloride, hexanoyl chloride, cyclopentyryl chloride, chlorobutyl chloride, 3-bromopropionyl chloride, 2,3-dichloropropionyl chloride, 4-chlorobutyryl chloride, 3-cyclopentylpropionyl chloride, hydrocinnamoyl chloride, cyclopentylacetyl chloride, isocaproic chloride, which are available commercially or prepared simply with public methods. Inorganic acid can be aluminum chloride and the reaction can be carried out in the range of −20 to 30° C. for 2 to 24 hours. The reaction solvent can be selected from dichloromethane, chloroform, etc. Acids used for preparing compound (8) are organic acid such as acetic acid and inorganic acid such as bromic acid and aluminum chloride. The reaction is preferably carried out in the range of 60 to 100° C. for 10 to 30 hours. To increase efficiency of the reaction, excess amount of acid can be used as solvent.

In step 1-3, 4-(5-chloropentoxyl)benzonitrile (4) prepared in step 1-1 is reacted with phenol compound (8) prepared in step 1-2 in the presence of base, thus preparing 4-(5-phenoxypentoxyl)benzonitrile compound (9). Inorganic bases can be used in this reaction, and selected form the group of potassium carbonate, sodium hydroxide and sodium hydride. The reaction can be carried out in the range of 10 to 90° C. for 1 to 9 hours and acetonitrile or dimethyl formamide are preferably used as as solvent.

In step 1-4, compound (9) prepared in step 1-3 is reacted with brominating agent, thus preparing α-brominated compound (10). brominating agent for the reaction can include copper (II) bromide, bromine, etc. and the reaction can be carried out in the range of 20 to 80° C. for 8 to 24 hours and ethyl acetate is preferably used as solvent.

In step 1-5, α-brominated compound (10) prepared in step 1-4 is reacted with thioamide (11), thus preparing compound (12) which has thiazole ring. In the reaction, thioamide (11) is a material to introduce substituent $R_1$ into the compound of formula 1 and can be selected according to their substituent radical. Reaction time and solvent vary according to thioamide compound (11), but in most case, the reaction can be carried out in the range of 60 to 90° C. for 5 to 24 hours. Thioamide compound (11) used for the reaction includes thioacetamide, thiopropionamide, thioisobutramide, trimethylthioacetamide, thiohexanoamide, cyclohexancarbothioicacid amide, N-(2-amino-2-thioxoethyl)-2-methylpropanamide, piperidin-4-carbothioic acid amide, thiourea, amidinothiourea, thiobenzoamide, glycine thioamide, 2,2-dimethyl thiopropionamide, which are available commercially or prepared simply with public methods. Ethanol or ethanol/water mixture is used as a solvent.

In step 1-6, compound (12) which has thiazole ring, prepared in step 1-5, is reacted with amine compound in the presence of bases, thus preparing compound (1a). In the case of N-hydroxy amidine ($R_5$=OH), hydroxylamine hydrochlowherein $R_2$, $R_3$, $R_4$, $R_5$, $X_1$, $X_2$ and $X_3$ are the same as defined in the compound of the formula 1 and n is an integer of 0 to 6.

Each step for preparing benzamidine compounds substituted with thiazole derivative of the present invention, is specifically described below:

In Reaction Scheme 1 to 4, the compound 2, the compound 5, the acid chloride 6, the compound 4, the compound 8, the thioamide 11, the thiourea 13, the halide compound (15, 17), the compound 19 of which both terminals are substituted with halogen are commercially available or can be prepared using the method well known in the art.

Reaction Scheme 1 is illustrated by using specific compounds as shown below.

In step 1-1, 4-hydroxy-benzonitrile (2; $R_4$=H, $X_3$=O) is reacted with 1-bromo-5-chloropentane (3; Br—$X_2$—Cl: $X_2$=pentylene), giving 4-(5-chloro-pentoxy)-benzonitrile ride is reacted in the presence of a base, and the base can be selected from organic bases such as triethylamine, 1,8-diazabicyclo[5.4.0]undec-7-ene, DBU, diethylmethylamine (Et$_2$NMe), N-methylmorpholine, N-methylpiperidine, pyridine and 2,6-dimethylpyridine, and inorganic bases such as potassium carbonate, potassium bicarbonate, sodium hydroxide, potassium hydroxide, sodium amide, sodium hydride, sodium methoxide, sodium ethoxide. The reaction is carried out in the range of 60 to 90° C. for 1 to 15 hrs. Methanol, ethanol, acetonitrile, etc., or their mixture with water can be used as a solvent.

In the case of amidine (R$_5$=H), methoxy imine is prepared from hydrocholide methanol solution in the range of 10 to 30° C. for 24 to 48 hours and then methanol is evaporated in vacuum condition. The resultant is reacted with ammonia ethanol solution in the range of 45 to 60° C. for 24 to 50 hours in high pressure reactor, finally preparing target amidines. Ethanol is preferably used as a solvent.

Reaction Scheme 2 is illustrated by using specific compounds as shown below.

Steps 2-1 to 2-4 in Reaction Scheme 2 are the same as those in Reaction Scheme 1.

In step 2-5, α-brominated compound (10) prepared in step 2-4 is reacted with thiourea (13), thus preparing benzonitrile compound (14) which has aminothiazole radical. In the reaction, thiourea (13) is a material to introduce substituent R$_1$ into the compound of the formula 1 and can be selected from thioureas with proper alkyl radical according to the type of substitutents. Reaction time and solvent vary according to the type of thiourea (13) selected which is available commercially or prepared in public methods. The reaction can be preferably carried out in the range of 60 to 90° C. for 5 to 24 hours preferentially. Ethanol or Ethanol/water mixture can be preferably used as a solvent.

In step 2-6, benzonitrile compound (14) which has aminothiazole radical prepared in step 2-5, is reacted with halide compound (15) in the presence of bases, thus preparing benzonitrile compound (16) which has thiazol ring substituted with amine. In the reaction, halide compound (15) is a material to introduce a substitutents into the amino group of the compound of the formula 1 of which the substituent R$_1$ is primary amine. Halide compound (15) can be selected according to their substituent radical. Reaction time and solvent vary according to selecting halide compound (15). The reaction can be preferably carried out in the range of 0 to 90° C. for 5 to 24 hours. Halide compound (15) can includes methyl iodide, ethyl iodide, propyl bromide, 2-chloroethylmethyl ether, chloroethyl morpholine, 3-bromomethylpyridine, bromoethanol, niconoylchloride, benzyl bromide, nicotinoyl chloride, ethanesulfonyl chloride, isoniconoyl chloride, bis-dibromide ethylester, acetoxyacetyl chloride, methoxyacetyl chloride, etc., which are commercially available or prepared in public methods. Acetonitrile or dimethylformamide can be preferably used as a solvent.

In step 2-7, benzonitrile compound (16) which has thiazol ring substituted with the primary amine, prepared in step 2-6, is reacted with amine compound in the same condition as that of step 1-6, thus preparing the compound of the formula 1.

Reaction Scheme 3 is illustrated by using specific compound as shown below.

Steps 3-1 to 3-6 in Reaction Scheme 3 are the same as those in Reaction Scheme 2.

In step 3-7, compound (16) prepared in step 3-6 is reacted with halide compound (17) in the presence of base, thus preparing benzonitrile compound (18) which has thiazole ring substituted with secondary amine. In the reaction, halide compound (17) is a material to introduce the second substituent into the amino group of the compound of the formula 1 of which the substituent R$_1$ is the secondary amine. Halide compound (17) can be selected according to its substituent radical. Reaction time and solvent vary according to selecting the halide compound (17) selected. The reaction can be preferably carried out in the range of 0 to 90° C. for 5 to 24 hours. Halide compound (17) can include methyl iodide, ethyl iodide, propyl bromide, 2-chloroethylmethyl ether, chloroethyl morpholine, 3-bromomethylpyridine, bromoethanol, niconoylchloride, benzyl bromide, nicotinoyl chloride, ethanesulfonyl chloride, isoniconoyl chloride, etc., which are commercially available or prepared in public methods. Acetonitrile or dimethylformamide can be preferably used as a solvent.

In step 3-8, benzonitrile compound (16) which has thiazol ring substituted with the secondary amine, prepared in step 3-7, is reacted with amine compound in the same condition as that of step 1-6, thus preparing the compound of the formula 1.

Reaction Scheme 4 is illustrated by using specific compounds as shown below.

Steps 4-1 to 4-5 in Reaction Scheme 4 are the same as those in Reaction Scheme 2.

In step 4-6, benzonitrile compound (14), which has aminothiazole, prepared in step 4-5, is reacted with the compound (19) of which both terminals are substituted by halogen in the presence of base, thus preparing benzonitrile compound (20) which has thiazole ring substituted with hetero ring. In the reaction, compound (19) is a material to introduce

into the substituent R$_1$ of the compound of the formula 1 and can be selected according to its substituents. The reaction can be carried out in the range of 0 to 90° C. for 4 to 24 hours. These halogenate compounds can include mechloethylamine, bisdibromide ethylester, 1,5-dibomopentane, etc., which are commercially available or prepared in public methods. Acetonitrile or dimethylformamide can be used as a solvent.

In step 4-7, benzonitrile compound (20) which has thiazole ring substituted with hetero ring, prepared in step 4-6, is reacted with the amine compound in the same condition ss that of step 1-6, thus preparing the compound of the formula 1.

In further aspect, the invention relates to a pharmaceutical composition for the prevention and treatment of osteoporosis, allergic inflammatory diseases and bone fracture comprising formula 1 and their pharmaceutically acceptable salts.

The term "osteoporosis" as used herein means the state that minerals and substrates are reduced abnormally in large amounts, so that there is no defect in their structure, however, o many pores develop in the bone, making it like sponge and more likely to fracture. In specific examples, the benzamidine compounds of the present invention suppressed the differentiation of osteoclast, facilitated bone formation, and remarkably inhibited the bone mass reduction in osteoporosis-induced animal models.

The term "bone fracture" as used herein means one of various physical injuries of a bone, based on a complete or incomplete disruption of the continuity of a bone, which are classified according to anatomical location (epiphyseal, metaphyseal, diaphyseal, intra-articular, proximal, midshaft, distal, etc.), degree of fracture (complete, incomplete), direction of fracture (transverse, oblique, spiral, longitudinal), presence of open wound (open, closed), number of fractures (simple, linear, segmental, comminuted, etc.), stability of fracture (stable, unstable), displacement of fracture, etc. As compared to a non-treated group, a group treated with the benzamidine compound of the formula 1 according to the present invention was found to have bony callus which significantly decreased in volume in a dose-dependent pattern, but increased both in bone density and in bone strength, with significance, in a dose-dependent pattern.

The term "allergic inflammatory diseases" means non-specific inflammatory diseases caused by various allergens, exemplified by allergic rhinitis, asthma, allergic conjunctivitis, allergic dermatitis, atopic dermatitis, contact dermatitis, urticaria, etc. In the specific embodiment of the present invention, the benzamidine compound of the formula 1 was found to have a great effect of reducing lung weight and total leukocyte numbers in asthma-induced animal models.

The composition of the present invention, a composition may comprises medicinally effective ingredient equivalents or similar in function to the benzamidine compound of Chemical Formula 1 or its pharmaceutically acceptable salt, in addition to Chemical Formula 1 or its pharmaceutically acceptable salt.

The composition of the present invention may comprise one or more pharmaceutically acceptable carriers. A proper carrier may be selected from a group consisting of saline, sterilized water, Ringer's solution, buffered saline, a dextrose solution, a maltodextrin solution, glycerol, ethanol, and combinations thereof, and may be, if necessary, further supplemented with other typical additives such as an antioxidant, a buffer, a static agent, etc. In combination with a diluent, a dispersant, a surfactant, a binder, and a lubricant, the composition of the present invention may also be formulated into injectable dosage forms, such as aqueous solutions, suspensions, emulsions, etc., pills, capsules, granules, and tablets. Moreover, depending on the kind of ingredient or disease, the formulation may be produced using methods known in the art or disclosed in Remington's Pharmaceutical Science ((latest version), Mack Publishing Company, Easton Pa.).

The composition of the present invention may be administered orally or parenterally (e.g., intravenously, subcutaneously, intraabdominally, or topically). The dosage of the composition of the present invention varies depending on body weight, age, gender, health state, diet, administration time period, administration route, excretion rate, disease severity, etc. When all of these factors are taken into account, the benzamidine compound of Chemical Formula 1 is administered once or many times at a dose of approximately 10 to 1,000 mg/kg a day, and preferably at a dose of approximately 50 to 500 mg/kg a day.

For the prevention and treatment of osteoporosis, allergic inflammatory disease and physical injury of bone comprising fracture, the administration of the composition of the present invention can be done alone or in combination with surgery, hormone therapy, chemical therapy, and/or a biological response controller.

A better understanding of the present invention may be obtained through the following examples which are set forth to illustrate, but are not to be construed as the limit of the present invention.

Preparative Example 1

Preparation of Compound (12) in Reaction Scheme 1

1-1: 4-(5-chloropentoxyl)-benzonitrile (4)

While 3.0 g (25.2 mmol) of 4-hydroxybenzonitrile were added to 80 ml of acetonitrile and stirred, 3.67 g (27 mmol) of potassium carbonate and 4.67 g (25.2 mmol) of 1-bromo-5-chloropentane were added. Subsequently, the temperature was gradually increased and stirring under reflux was continued for 7 hr, and then stirring was further continued to 80-82° C. The temperature was decreased to room temperature, and Ethyl acetate was added, and organic layer washed with distilled water. Thereafter, the organic layer was dried over anhydrous magnesium sulfate, and then concentrated under reduced pressure. The concentrated compound was recrystallized in methanol, then filtered, and washed with −10° C. methanol, thus obtaining 5.09 g (yield: 90.3%) of a title compound (4).

m.p. 47~49° C.;
$^1$H-NMR (CDCl$_3$) (ppm) 1.64 (m, 2H), 1.82 (m, 4H), 3.57 (t, 2H), 4.01 (t, 2H), 6.93 (d, 2H), 7.57 (d, 2H)

1-2: 1-(4-methoxyphenyl)-1-propanone (7)

While 49.3 g (370 mmol) of aluminium chloride were added to 200 ml of dichloromethane and stirred, 40 g (370 mmol) of anisole were slowly added in droplets at 5° C. Subsequently, 32 ml (370 mmol) of propionyl chloride were slowly added in droplets for 30 min, and stirring was further continued at room temperature for 2 hr. After the reaction was completed, the resultant reaction mixture was diluted with dichloromethane, and then washed with a saturated aqueous solution of sodium bicarbonate and water at 5° C. The organic layer was dried over anhydrous magnesium sulfate and then concentrated under reduced pressure. Organic residue was purified with column-chromatography in which the mixture of ethyl acetate and n-hexane (1:10) were used as a eluent, thus obtaining 59.5 g (yield: 98%) of a title compound (7).

$^1$H-NMR (DMSO-d$_6$) (ppm) 1.05 (t, 3H), 2.94 (q, 2H), 3.81 (s, 3H), 7.02 (d, 2H), 7.93 (d, 2H)

1-3: 1-(4-hydroxyphenyl)propan-1-one (8)

While 20 g (0.121 mmol) of 1-(4-methoxyphenyl)-1-propanone (7) prepared in Example 1-2 were added to 139 ml (2.4 mol) of acetic acid and stirred, 270 ml (2.4 mmol) of 48% bromic acid were added. Subsequently, the temperature was gradually increased to 100° C. and stirring under reflux was continued for 18 hr. The temperature was decreased to room temperature, and ethyl acetate was added, and organic layer was washed with water. Thereafter, the organic layer was washed with a saturated aqueous solution of potassium carbonate, then concentrated under reduced pressure, after which the precipitated solid was recrystallized with ethyl acetate/n-hexane system, and filtered, thus obtaining 12.7 g (yield: 70%) of a title compound (8) as a solid.

m.p.: 143~150° C.
$^1$H-NMR (DMSO-d$_6$) (ppm) 1.03 (t, 3H), 2.91 (q, 2H), 6.83 (d, 2H), 7.82 (d, 2H), 10.28 (s, 1H).

1-4: 4-[5-(4-propionylphenoxy)pentoxyl]-benzonitrile (9)

While 12 g (80 mmol) of 1-(4-hydroxyphenyl)propan-1-one (8) prepared in Example 1-3 were added to 100 ml of dimethylformamide and stirred, 3.5 g (84 mmol) of sodium hydride were added, and stirring was continued for 20 min. Thereafter, 17.9 g (80 mmol) of 4-(5-chloro-pentoxy)-benzonitrile (4) prepared in Example 1-1 were dissolved in 20 ml of dimethylformamide. The reaction temperature was gradually increased and stirring was continued at 40° C. for 4 hr. After the reaction was completed, the temperature was decreased to room temperature, and the resultant reaction mixture was added with ethylacetate, and then washed with distilled water. Subsequently, the organic layer was dried over anhydrous magnesium sulfate, and then concentrated under reduced pressure. The residue was purified with column-chromatography in which the mixture of ethylacetate and n-hexane (1:5) were used as a eluent, thus obtaining 21.6 g (yield: 80%) of a title compound (9).

m.p.: 107~111° C.

$^1$H-NMR (DMSO-$d_6$) (ppm) 1.04 (t, 3H), 1.56 (m, 2H), 1.78 (brm, 4H), 2.95 (q, 2H), 4.07 (4H), 7.00 (d, 2H), 7.08 (d, 2H), 7.74 (d, 2H), 7.90 (d, 2H).

1-5: 4-5-[4-(2-bromopropionyl)phenoxy]pentoxy-benzonitrile (10)

While 20 g (59 mmol) of 4-[5-(4-propionylphenoxy)pentoxy]-benzonitrile (9) prepared in Example 1-4 were added to 300 ml of ethylacetate and stirred, 26 g (119 mmol) of copper (II) bromide were added, and the reaction temperature was gradually increased and stirring was continued at 70° C. for 8 hr. After the reaction was completed, the resultant reaction mixture was cooled to room temperature and the salts were removed by filtration. The ethylacetate layer was washed with sodium bicarbonate and sodium chloride. Subsequently, the organic layer was dried over anhydrous magnesium sulfate and then concentrated under reduced pressure, thus obtaining 23 g (yield: 95.0%) of a title compound (10).

m.p.: 79~81° C.

$^1$H-NMR (DMSO-$d_6$) (ppm) 1.57 (m, 2H), 1.74 (d, 2H), 1.79 (brm, 4H), 4.08 (m, 4H), 5.77 (q, 1H), 7.07 (m, 4H), 7.74 (d, 2H), 7.99 (d, 2H).

1-6: 4-5-[4-(5-methyl-2-isopropyl-1,3-thiazol-4-yl)phenoxy]pentoxyl-benzonitrile (12)

While 1 g (2.4 mmol) of 4-5-[4-(2-bromopropionyl)phenoxy]pentoxyl-benzonitrile (10) prepared in Example 1-5 were added to 30 ml of ethanol and stirred, 0.25 g (2.4 mmol) of isobutrathioamide were added. Subsequently, the temperature was gradually increased to 80° C. and stirring under reflux was continued for 5 hr. After the reaction was completed, the resultant reaction mixture was concentrated under reduced pressure, and diluted with dichloromethane, and then washed with a saturated aqueous solution of sodium bicarbonate and brine. The organic layer was dried over anhydrous magnesium sulfate, and then concentrated under reduced pressure. The residue was purified with column-chromatography in which the mixture of ethylacetate and n-hexane (1:6) were used as a eluent, thus obtaining 0.9 g (yield: 89%) of a title compound (12).

m.p.: 70~73° C.

$^1$H-NMR (DMSO-$d_6$) (ppm) 1.32 (d, 6H), 1.59 (m, 2H), 1.79 (m, 4H), 2.47 (s, 3H), 3.21 (m, 1H), 4.02 (t, 2H), 4.09 (t, 2H), 6.98 (d, 2H), 7.09 (d, 2H), 7.55 (d, 2H), 7.74 (d, 2H).

Preparative Example 2

Preparation of Compound (16) in Reaction Scheme 2

2-1: 4-5-[4-(5-methyl-2-amino-1,3-thiazol-4-yl)phenoxy]pentoxy-benzonitrile (14)

While 3 g (7.2 mmol) of 4-5-[4-(2-bromopropionyl)phenoxy]pentoxyl-benzonitrile (10) prepared in Example 1-5 were added to 30 ml of ethanol and stirred, 0.58 g (7.6 mmol) of thiourea were added. Subsequently, the temperature was gradually increased to 80° C. and stirring under reflux was continued for 5 hr. After the reaction was completed, the resultant reaction mixture was concentrated under reduced pressure, and diluted with dichloromethane, and then washed with a saturated aqueous solution of sodium bicarbonate and brine. The organic layer was dried over anhydrous magnesium sulfate, and then concentrated under reduced pressure. The residue was purified with column-chromatography in which the mixture of ethylacetate and hexane (1:2) were used as a eluent, thus obtaining 2.5 g (yield: 89%) of a title compound (14).

$^1$H-NMR (DMSO-$d_6$) (ppm) 1.57 (m, 2H), 1.78 (m, 4H), 2.27 (s, 3H), 3.98 (t, 2H), 4.07 (t, 2H), 6.69 (s, 2H), 6.91 (d, 2H), 7.09 (d, 2H), 7.45 (d, 2H), 7.74 (d, 2H).

2-2: 4-5-[4-(5-methyl-2-ethylamino-1,3-thiazol-4-yl)phenoxy]pentoxy-benzonitrile (16)

While 0.60 g (1.52 mmol) of 4-5-[4-(5-methyl-2-amino-1,3-thiazol-4-yl)phenoxy]pentoxy-benzonitrile (14) prepared in Example 2-1 were added to 50 ml of dimethylformamide and stirred, 0.07 g (1.83 mmol) of sodium hydride were added. After stirring for 20 min, 0.13 ml (1.6 mmol) of ethyl iodide were added, and the temperature was gradually increased to 40° C. and stirring was continued for 4 hr. After the reaction was completed, the resultant reaction mixture was partitioned between distilled water and ethylacetate. The organic layer was dried over anhydrous magnesium sulfate, and then concentrated under reduced pressure. The residue was purified with column-chromatography in which the mixture of ethylacetate and n-hexane (1:2) were used as a eluent, thus obtaining 0.32 g (yield: 50%) of a title compound (16).

$^1$H-NMR (DMSO-$d_6$ (ppm) 1.13 (t, 3H), 1.56 (m, 2H), 1.78 (m, 4H), 2.28 (s, 3H), 3.19 (m, 2H), 3.99 (t, 2H), 4.07 (t, 2H), 6.92 (d, 2H), 7.09 (d, 2H), 7.26 (t, 1H), 7.47 (d, 2H), 7.74 (d, 2H).

Preparative Example 3

Preparation of Compound (18) in Reaction Scheme 3

4-5-[4-(5-methyl-2-[ethyl-(2-morpholinoethyl)amino]-1,3-thiazol-4-yl)phenoxy]pentoxy-benzonitrile (18)

While 0.40 g (0.94 mmol) of 4-5-[4-(5-methyl-2-ethylamino-1,3-thiazol-4-yl)phenoxy]pentoxy-benzonitrile (16) prepared in Example 2-2 were added to 50 ml of dimethylsulfoxide and stirred, 0.10 g (2.37 mmol) of sodium hydride were added. After stirring for 20 min, 0.18 g (0.99 mmol) of N-(2-chloroethyl)morpholine hydrochloride were added, and the temperature was gradually increased to 40° C. and stirring was continued for 4 hr. After the reaction was completed, the resultant reaction mixture was partitioned between distilled water and ethylacetate. The organic layer was dried over anhydrous magnesium sulfate, and then concentrated under reduced pressure. The residue was purified with column-chromatography in which the mixture of ethylacetate and n-hexane (1:2) were used as a eluent, thus obtaining 0.35 g (yield: 70%) of a title compound (18).

$^1$H-NMR (DMSO-$d_6$) (ppm) 1.15 (t, 3H), 1.55 (m, 2H), 1.77 (brm, 4H), 2.31 (s, 3H), 2.42 (brm, 4H), 2.51 (m, 2H), 3.39 (t, 2H), 4.07 (t, 2H), 6.93 (d, 2H), 7.09 (d, 2H), 7.48 (d, 2H), 7.74 (d, 2H).

Preparative Example 4

Preparation of Compound (20) in Reaction Scheme 4

4-5-[4-(5-methyl-2-piperidino-1,3-thiazol-4-yl)phenoxy]pentoxy-benzonitrile (20)

While 0.50 g (1.27 mmol) of 4-5-[4-(5-methyl-2-amino-1,3-thiazol-4-yl)phenoxy]pentoxy-benzonitrile (14) prepared in Example 2-1 were added to 50 ml of dimethylformamide and stirred, 0.11 g (2.79 mmol) of sodium hydride were added. After stirring for 20 min, 0.19 ml (1.4 mmol) of 1,5-dibromopentane was added, and the temperature was gradually increased to 40° C. and stirring was continued for 4 hr. After the reaction was completed, the resultant reaction mixture was partitioned between distilled water and ethylacetate. The organic layer was dried over anhydrous magnesium sulfate, and then concentrated under reduced pressure. The residue was purified with column-chromatography in which the mixture of ethylacetate and n-hexane (1:2) were used as a eluent, thus obtaining 0.57 g (yield: 98%) of a title compound (20).

$^1$H-NMR (DMSO-$d_6$) (ppm) 1.57 (m, 2H), 1.63 (brm, 6H), 1.77 (brm, 4H), 2.20 (s, 3H), 3.60 (brm, 4H), 4.04 (m, 4H), 7.04 (d, 4H), 7.40 (d, 2H), 7.68 (d, 2H).

Example 1

Preparation of N-hydroxy-4-5-[4-(5-methyl-2-isopropyl-1,3-thiazol-4-yl)phenoxy]pentoxyl-benzamidine While 0.3 g (0.71 mmol) of 4-5-[4-(5-methyl-2-isopropyl-1,3-thiazol-4-yl)phenoxy]pentoxyl-benzonitrile (12) prepared in Example 1-6 were added to 10 ml of ethanol and stirred, 0.11 g (2.9 mmol) of sodium hydroxide and 0.20 g (2.9 mmol) of hydrochloride, dissolved in ethanol (5 ml)/water (1 ml) co-solvent, were added. The temperature was gradually increased to 80° C. and stirring was continued for 15 hr. The resultant reaction mixture was concentrated under reduced pressure, and diluted with dichloromethane, and then washed with a distilled water. The organic layer was dried over anhydrous magnesium sulfate and then the resultant reaction mixture was concentrated under reduced pressure, then purified with column-chromatography in which the mixture of ethylacetate, n-hexane and methanol (5:10:1) were used as a eluent, thus obtaining 0.19 g (yield: 52%) of a title compound.

$^1$H-NMR (DMSO-$d_6$) (ppm) 1.31 (d, 6H), 1.58 (m, 2H), 1.79 (m, 4H), 2.47 (s, 3H), 3.21 (m, 1H), 4.00 (m, 4H), 5.71 (s, 2H), 6.91 (d, 2H), 6.99 (d, 2H), 7.56 (m, 4H), 9.44 (s, 1H).

Example 2

Preparation of 4-5-[4-(5-methyl-2-isopropyl-1,3-thiazol-4-yl)phenoxy]pentoxyl-benzamidine While 0.22 g (0.52 mmol) of 4-5-[4-(5-methyl-2-isopropyl-1,3-thiazol-4-yl)phenoxy]pentoxyl-benzonitrile (12) prepared in Example 1-6 were added to 10 ml of saturated hydrochloride/methanol solution and stirred for 24 hr, and the resultant reaction mixture was concentrated under reduced pressure. The organic residue was dissolved with 2 ml of ethanol, and put it in sealed tube. 10 ml of ammonia ethanol solution was added to the tube, and the temperature was gradually increased to 50° C. and stirring was continued for 40 hr. After the reaction was completed, the resultant reaction mixture was concentrated under reduced pressure, and was purified with column-chromatography in which the mixture of chloroform, methanol (8:1) were used as chromatography solvent, thus obtaining 0.10 g (yield: 48%) of a title compound.

$^1$H-NMR (DMSO-$d_6$) (ppm) 1.33 (d, 6H), 1.61 (m, 2H), 1.82 (brm, 4H), 2.49 (s, 3H), 3.22 (m, 1H), 4.04 (t, 2H), 4.14 (t, 2H), 7.01 (d, 2H), 7.17 (d, 2H), 7.57 (d, 2H), 7.85 (d, 2H).

Examples 3 to 83

1. N-hydroxy benzamidine ($R_5$=OH)

Examples 3 to 51, 57 to 83

Compound (12) prepared according to the same method as that in the Preparative Example 1-6 was reacted in the same manner as Example 1, obtaining the title compounds shown I Table 1.

Table 1 shows the title compounds, reactants and $^1$H-NMR data.

TABLE 1

| example | name | Acid chloride | Thioamide | Alkylhalide | NMR | solvent | mp |
|---|---|---|---|---|---|---|---|
| 1 | N-hydroxy-4-5-[4-(2-isopropyl-5-methyl-1,3-thiazol-4-yl)phenoxy]pentoxy-benzamidine | Propionylchloride | Thioisobutramide | | 1.31 (d, 6H), 1.58 (m, 2H), 1.79 (m, 4H), 2.47 (s, 3H), 3.21 (m, 1H), 4.00 (m, 4H), 5.71 (s, 2H), 6.91 (d, 2H), 6.99 (d, 2H), 7.56 (m, 4H), 9.44 (s, 1H) | DMSO-$d_6$ | — |
| 2 | 4-5-[4-(2-isopropyl-5-methyl-1,3-thiazol-4-yl)phenoxy]pentoxy-benzamidine | Propionylchloride | Thioisobutramide | | 1.33 (d, 6H), 1.61 (m, 2H), 1.82 (brm, 4H), 2.49 (s, 3H), 3.22 (m, 1H), 4.04 (t, 2H), 4.14 (t, 2H), 7.01 (d, 2H), 7.17 (d, 2H), 7.57 (d, 2H), 7.85 (d, 2H). | DMSO-$d_6$ | — |
| 3 | N-hydroxy-4-5-[4-(2-methyl-1,3-thiazol-4-yl)phenoxy]pentoxy-benzamidine | Acetylchloride | Thioacetamide | | 1.56 (m, 2H), 1.78 (brm, 4H), 2.68 (s, 3H), 4.00 (m, 4H), 5.70 (s, 2H), 6.90 (d, 2H), 6.96 (d, 2H), 7.57 (d, 2H), 7.72 (s, 1H), 7.83 (d, 2H), 9.43 (s, 1H) | DMSO-$d_6$ | 139-140 |

TABLE 1-continued

| example | name | Acid chloride | Thioamide | Alkylhalide | NMR | solvent | mp |
|---|---|---|---|---|---|---|---|
| 4 | N-hydroxy-4-5-[4-(2-ethyl-1,3-thiazol-4-yl)phenoxy]pentoxy-benzamidine | Acetylchloride | Thiopropionamide | | 1.32 (t, 3H), 1.57 (brm, 2H), 1.77 (brm, 4H), 3.01 (q, 2H), 4.00 (m, 4H), 5.71 (s, 2H), 6.91 (d, 2H), 6.96 (d, 2H), 7.57 (d, 2H), 7.75 (s, 1H), 7.84 (d, 2H), 9.43 (s, 1H) | DMSO-$d_6$ | |
| 5 | N-hydroxy-4-5-[4-(2-isopropyl-1,3-thiazol-4-yl)phenoxy]pentoxy-benzamidine | Acetylchloride | Thioisobutramide | | 1.35 (d, 6H), 1.58 (m, 2H), 1.78 (brm, 4H), 3.28 (m, 1H), 4.00 (m, 4H), 5.79 (brs, 2H), 6.91 (d, 2H), 6.97 (d, 2H), 7.58 (d, 2H), 7.76 (s, 1H), 7.84 (d, 2H), 9.47 (s, 1H) | DMSO-$d_6$ | 95-129 |
| 6 | N-hydroxy-4-5-[4-(2-phenyl-1,3-thiazol-4-yl)phenoxy]pentoxy-benzamidine | Acetylchloride | Thiobenzamide | | 1.58 (m, 2H), 1.80 (brm, 4H), 4.02 (m, 4H), 5.81 (brs, 2H), 6.92 (d, 2H), 7.01 (d, 2H), 7.51 (m, 3H), 7.58 (d, 2H), 7.96 (d, 2H), 8.01 (m, 3H), 9.49 (s, 1H) | DMSO-$d_6$ | 133-141 |
| 7 | N-hydroxy-4-5-[4-(2-pyridin-3-yl-1,3-thiazol-4-yl)phenoxy]pentoxy-benzamidine | Acetylchloride | Thionicotinamide | | 1.58 (brm 2H), 1.80 (brm, 4H), 4.02 (t, 4H), 5.73 (s, 2H), 6.91 (d, 2H), 7.02 (d, 2H), 7.55 (m, 3H), 7.82 (d, 2H), 7.97 (d, 2H), 8.10 (s, 1H), 8.36 (d, 1H), 8.67 (d, 1H), 9.19 (s, 1H), 9.45 (s, 1H) | DMSO-$d_6$ | 149-154 |
| 8 | N-hydroxy-4-5-[4-(2-cyclohexyl-1,3-thiazol-4-yl)phenoxy]pentoxy-benzamidine | Acetylchloride | Cyclohexanecarbothioic acide amide | | 1.23 (m, 1H), 1.47 (m, 6H), 1.65 (m, 1H), 1.77 (brm, 6H), 2.06 (m, 2H), 2.99 (m, 1H), 4.00 (m, 4H), 5.70 (s, 2H), 6.90 (d, 2H), 6.96 (d, 2H), 7.57 (d, 2H), 7.74 (d, 2H), 7.83 (d, 2H), 9.44 (s, 1H) | DMSO-$d_6$ | |
| 9 | N-hydroxy-4-5-[4-(2-pentyl-1,3-thiazol-4-yl)phenoxy]pentoxy-benzamidine | Acetylchloride | Thiohexanoamide | | 0.86 (t, 3H), 1.33 (brm, 4H), 1.56 (brm, 2H), 1.73 (brm, 6H), 2.97 (m, 2H), 4.00 (m, 4H), 5.70 (s, 2H), 6.90 (d, 2H), 6.96 (m, 2H), 7.57 (d, 2H), 7.74 (s, 1H), 7.83 (d, 2H), 9.44 (s, 1H) | DMSO-$d_6$ | |
| 10 | N-hydroxy-4-5-[4-(2,5-dimethyl-1,3-thiazol-4-yl)phenoxy]pentoxy-benzamidine | Propionylchloride | Thioacetamide | | 1.57 (m, 2H), 1.78 (m, 4H), 2.44 (s, 3H), 2.58 (s, 3H), 4.01 (m, 4H), 5.72 (s, 2H), 6.97 (d, 2H), 7.54 (d, 2H), 7.57 (d, 2H), 9.44 (s, 1H) | DMSO-$d_6$ | 128-133 |
| 11 | N-hydroxy-4-5-[4-(2-ethyl-5-methyl-1,3-thiazol-4-yl)phenoxy]pentoxy-benzamidine | Propionylchloride | Thiopropionamide | | 1.27 (t, 3H), 1.57 (m, 2H), 1.78 (brm, 4H), 2.45 (s, 3H), 2.91 (q, 2H), 4.01 (m, 4H), 5.75 (brs, 2H), 6.91 (d, 2H), 6.98 (d, 2H), 7.54 (d, 2H), 7.57 (d, 2H), 9.46 (s, 1H). | DMSO-$d_6$ | 127-131 |
| 12 | N-hydroxy-4-5-[4-(5-methyl-2-phenyl-1,3-thiazol-4-yl)phenoxy]pentoxy-benzamidine | Propionylchloride | Thiobenzamide | | 1.58 (m, 2H), 1.79 (m, 4H), 2.56 (s, 3H), 4.02 (m, 4H), 5.78 (brs, 2H), 6.91 (d, 2H), 7.03 (d, 2H). 7.49 (m, 3H), 7.58 (d, 2H), 7.65 (d, 2H), 7.91 (d, 2H), 9.45 (s, 1H) | DMSO-$d_6$ | 124-130 |
| 13 | N-hydroxy-4-5-[4-(5-methyl-2-pyridin-3-yl-1,3-thiazol-4-yl)phenoxy]pentoxy-benzamidine | Propionylchloride | Thionicotinamide | | 1.59 (m, 2H), 1.79 (m, 2H), 2.58 (s, 3H), 4.02 (m, 4H), 5.72 (s, 2H), 6.91 (d, 2H), 7.03 (d, 2H), 7.52 (m, 1H), 7.58 (d, 2H), 7.66 (d, 2H), 8.26 (d, 1H), 8.64 (d, 1H), 9.09 (d, 1H), 9.45 (s, 1H) | DMSO-$d_6$ | 138-150 |
| 14 | N-hydroxy-4-5-[4-(2-cyclohexyl-5-methyl-1,3-thiazol-4-yl)phenoxy]pentoxy-benzamidine | Propionylchloride | Cyclohexanecarbothioic acide amide | | 1.26 (m, 1H), 1.43 (brm, 4H), 1.61 (m, 2H), 1.67 (m, 1H), 1.80 (brm, 6H), 2.04 (m, 1H), 2.49 (s, 3H), 2.92 (m, 1H), 4.03 (m, 4H), 5.73 (s, 2H), 6.94 (d, 2H), 7.01 (d, 2H), 7.57 (d, 2H), 7.60 (d, 2H), 9.47 (s, 1H) | DMSO-$d_6$ | — |

TABLE 1-continued

| example | name | Acid chloride | Thioamide | Alkylhalide | NMR | solvent | mp |
|---|---|---|---|---|---|---|---|
| 15 | N-hydroxy-4-5-[4-(5-methyl-2-pentyl-1,3-thiazol-4-yl)phenoxy]pentoxy-benzamidine | Propionylchloride | Thiohexanoamide | | 0.86 (t, 3H), 1.31 (brm, 4H), 1.58 (m, 2H), 1.68 (m, 2H), 1.78 (brm, 4H), 2.46 (s, 3H), 2.88 (t, 2H), 4.01 (m, 4H), 5.72 (brs, 2H), 6.92 (d, 2H), 6.98 (d, 2H), 7.53 (d, 2H), 7.57 (d, 2H), 9.45 (s, 1H) | DMSO-$d_6$ | 81-89 |
| 16 | N-hydroxy-4-5-[4-(2-t-butyl-5-methyl-1,3-thiazol-4-yl)phenoxy]pentoxy-benzamidine | Propionylchloride | 2,2-dimethylthio-propionamide | | 1.36 (s, 9H), 1.57 (m, 2H), 1.78 (brm, 4H), 2.45 (s, 3H), 4.00 (m, 4H), 5.72 (s, 2H), 6.91 (d, 2H), 6.98 (d, 2H), 7.55 (d, 2H), 7.58 (d, 2H), 9.44 (s, 1H) | DMSO-$d_6$ | — |
| 17 | N-hydroxy-4-5-[4-(5-ethyl-2-methyl-1,3-thiazol-4-yl)phenoxy]pentoxy-benzamidine | Butrylchloride | Thioacetamide | | 1.26 (t, 3H), 1.66 (m, 2H), 1.85 (brm, 4H), 2.83 (s, 3H), 2.86 (q, 2H), 4.00 (m, 4H), 4.88 (brs, 1H), 6.87 (d, 2H), 6.91 (d, 2H), 7.46 (d, 2H), 7.52 (d, 2H) | CDCl$_3$ | — |
| 18 | N-hydroxy-4-5-[4-(2,5-diethyl-1,3-thiazol-4-yl)phenoxy]pentoxy-benzamidine | Butrylchloride | Thiopropionamide | | 1..22 (t, 3H), 1.28 (t, 3H), 1.57 (m, 2H), 1.78 (brm, 4H), 2.85 (q, 2H), 4.01 (m, 2H), 5.73 (s, 2H), 6.91 (d, 2H), 6.98 (d, 2H), 7.48 (d, 2H), 7.57 (d, 2H), 9.44 (s, 1H) | DMSO-$d_6$ | 121-127 |
| 19 | N-hydroxy-4-5-[4-(5-ethyl-2-isopropyl-1,3-thiazol-4-yl)phenoxy]pentoxy-benzamidine | Butrylchloride | Thioisobutramide | | 1.22 (t, 3H), 1.31 (d, 6H), 1.57 (m, 2H), 1.78 (brm, 4H), 2.86 (q, 2H), 3.24 (m, 1H), 4.01 (m, 4H), 5.70 (s, 2H), 6.90 (d, 2H), 6.98 (d, 2H), 7.49 (d, 2H), 7.58 (d, 2H), 9.43 (s, 1H) | DMSO-$d_6$ | |
| 20 | N-hydroxy-4-5-[4-(5-ethyl-2-phenyl-1,3-thiazol-4-yl)phenoxy]pentoxy-benzamidine | Butrylchloride | Thiobenzamide | | 1.29 (t, 2H), 1.58 (m, 2H), 1.79 (m, 4H), 2.96 (q, 2H), 4.03 (m, 4H), 5.70 (s, 2H), 6.91 (d, 2H), 7.03 (d, 2H), 7.43 (m, 3H), 7.58 (m, 4H), 7.90 (m, 2H), 9.43 (s, 1H) | DMSO-$d_6$ | 83-86 |
| 21 | N-hydroxy-4-5-[4-(5-ethyl-2-pyridin-3-yl-1,3-thiazol-4-yl)phenoxy]pentoxy-benzamidine | Butrylchloride | Thionicotinamide | | 1.30 (t, 3H), 1.58 (m, 2H), 1.79 (m, 4H), 2.98 (q, 2H), 4.02 (m, 4H), 5.69 (s, 2H), 6.91 (d, 2H), 7.04 (d, 2H), 7.52 (m, 1H), 7.59 (m, 4H), 8.26 (m, 1H), 8.63 (m, 1H), 9.10 (s, 1H), 9.42 (s, 1H) | DMSO-$d_6$ | 146-153 |
| 22 | N-hydroxy-4-5-[4-(2-cyclohexyl-5-ethyl-1,3-thiazol-4-yl)phenoxy]pentoxy-benzamidine | Butrylchloride | Cyclohexanecarbothioic acide amide | | 1.22 (m, 4H), 1.38 (m, 4H), 1.58 (m, 2H), 1.64 (m, 1H), 1.89 (brm, 6H), 2.01 (m, 2H), 2.87 (m, 3H), 4.01 (m, 4H), 5.71 (s, 2H), 6.91 (s, 2H), 6.98 (d, 2H), 7.48 (d, 2H), 7.57 (d, 2H), 9.44 (s, 1H) | DMSO-$d_6$ | — |
| 23 | N-hydroxy-4-5-[4-(5-ethyl-2-pentyl-1,3-thiazol-4-yl)phenoxy]pentoxy-benzamidine | Butrylchloride | Thiohexanoamide | | 0.86 (t, 3H), 1.21 (t, 3H), 1.32 (brm, 4H), 1.58 (m, 2H), 1.69 (m, 2H), 1.78 (brm, 4H), 2.87 (m, 4H), 4.01 (m, 4H), 5.72 (s, 2H), 6.91 (d, 2H), 6.98 (d, 2H), 7.48 (d, 2H), 7.58 (d, 2H), 9.44 (s, 1H) | DMSO-$d_6$ | 79-88 |
| 24 | N-hydroxy-4-5-[4-(2-ethyl-5-isopropyl-1,3-thiazol-4-yl)phenoxy]pentoxy-benzamidine | Isovalerylchloride | Thiopropionamide | | 1.26 (m, 9H), 1.57 (m, 2H), 1.79 (brm, 4H), 2.92 (q, 2H), 3.31 (m, 1H), 4.01 (m, 4H), 5.71 (brs, 2H), 6.91 (d, 2H), 6.98 (d, 2H), 7.43 (d, 2H), 7.57 (d, 2H) | DMSO-$d_6$ | — |
| 25 | N-hydroxy-4-5-[4-(2,5-diisopropyl-1,3-thiazol-4-yl)phenoxy]pentoxy-benzamidine | Isovalerylchloride | Thioisobutramide | | 1.24 (d, 6H), 1.31 (d, 6H), 1.56 (brm, 2H), 1.76 (brm, 5H), 3.21 (m, 1H), 3.90 (t, 2H), 4.01 (t, 2H), 5.68 (s, 2H), 6.79 (d, 2H), 6.99 (d, 2H), 7.25 (d, 2H), 7.43 (d, 2H), 8.27 (s, 1H) | DMSO-$d_6$ | |

TABLE 1-continued

| example | name | Acid chloride | Thioamide | Alkylhalide | NMR | solvent | mp |
|---|---|---|---|---|---|---|---|
| 26 | N-hydroxy-4-5-[4-(5-isopropyl-2-phenyl-1,3-thiazol-4-yl)phenoxy]pentoxy-benzamidine | Isovalerylchloride | Thiobenzamide | | 1.31 (d, 6H), 1.58 (brm, 2H), 1.78 (brm, 4H), 3.44 (m, 1H), 4.02 (m, 4H), 5.70 (s, 2H), 6.91 (d, 2H), 7.03 (d, 2H), 7.47 (m, 3H), 7.56 (m, 4H), 7.90 (d, 2H), 9.44 (s, 1H) | DMSO-$d_6$ | |
| 27 | N-hydroxy-4-5-[4-(5-isopropyl-2-pyridin-3-yl-1,3-thiazol-4-yl)phenoxy]pentoxy-benzamidine, | Isovalerylchloride | Thionicotinamide | | 1.32 (d, 6H), 1.57 (brm, 2H), 1.78 (brm, 4H), 4.00 (m, 4H), 5.71 (s, 2H), 6.91 (d, 2H), 7.04 (d, 2H), 7.51 (m, 1H), 7.58 (m, 4H), 8.27 (d, 1H), 8.64 (d, 1H), 9.10 (d, 1H), 9.44 (s, 1H) | DMSO-$d_6$ | |
| 28 | N-hydroxy-4-5-[4-(5-isopropyl-2-pentyl-1,3-thiazol-4-yl)phenoxy]pentoxy-benzamidine | Isovalerylchloride | Thiohexanoamide | | 0.84 (t, 3H), 1.23 (d, 6H), 1.32 (brm, 4H), 1.56 (m, 2H), 1.69 (m, 2H), 1.78 (brm, 4H), 2.88 (m, 2H), 3.36 (m, 1H), 4.01 (m, 4H), 5.73 (s, 2H), 6.91 (d, 2H), 6.98 (d, 2H), 7.43 (d, 2H), 7.58 (d, 2H), 9.45 (s, 1H) | DMSO-$d_6$ | |
| 29 | N-hydroxy-4-5-[4-(2-methyl-5-propyl-1,3-thiazol-4-yl)phenoxy]pentoxy-benzamidine | Pentanoyl chloride | Thioacetamide | | 0.91 (t, 3H), 1.57-1.61 (m, 4H), 1.78 (m, 4H), 2.60 (s, 3H), 2.80 (m, 2H), 4.01 (m, 4H), 5.85 (brs, 2H), 6.93 (d, 2H), 6.98 (d, 2H), 7.47 (d, 2H), 7.58 (d, 2H), 9.51 (s, 1H) | DMSO-$d_6$ | |
| 30 | N-hydroxy-4-5-[4-(5-butyl-2-methyl-1,3-thiazol-4-yl)phenoxy]pentoxy-benzamidine | Hexanoylchloride | Thioacetamide | | 0.83 (t, 3H), 1.30 (m, 2H), 1.53 (m, 4H), 1.78 (brm, 4H), 2.59 (s, 3H), 2.82 (m, 2H), 4.00 (m, 4H), 5.74 (brs, 2H), 6.91 (d, 2H), 7.46 (d, 2H), 7.57 (d, 2H), 9.45 (s, 1H) | DMSO-$d_6$ | 138-140 |
| 31 | N-hydroxy-4-5-[4-(5-butyl-2-ethyl-1,3-thiazol-4-yl)phenoxy]pentoxy-benzamidine | Hexanoylchloride | Thiopropionamide | | 0.84 (t, 3H), 1.27 (t, 3H), 1.31 (m, 2H), 1.56 (m, 4H), 1.78 (brm, 4H), 2.83 (t, 2H), 2.92 (m, 2H), 4.01 (m, 4H), 5.72 (brs, 2H), 6.91 (d, 2H), 6.98 (d, 2H), 7.47 (d, 2H), 7.58 (d, 2H), 9.45 (s, 2H) | DMSO-$d_6$ | 80-84 |
| 32 | N-hydroxy-4-5-[4-(5-butyl-2-isopropyl-1,3-thiazol-4-yl)phenoxy]pentoxy-benzamidine | Hexanoylchloride | Thioisobutramide | | 0.84 (t, 3H), 1.31 (m, 8H), 1.57 (m, 4H), 1.78 (brm, 4H), 2.83 (m, 2H), 3.24 (m, 1H), 4.01 (m, 4H), 5.74 (brs, 2H), 6.91 (d, 2H), 6.98 (d, 2H), 7.47 (d, 2H), 7.57 (d, 2H), 9.45 (s, 1H) | DMSO-$d_6$ | — |
| 33 | N-hydroxy-4-5-[4-(5-butyl-2-phenyl-1,3-thiazol-4-yl)phenoxy]pentoxy-benzamidine | Hexanoylchloride | Thiobenzamide | | 0.86 (t, 3H), 1.33 (m, 2H), 1.61 (m, 4H), 1.80 (m, 4H), 2.92 (t, 2H), 4.01 (m, 4H), 5.72 (brs, 2H), 6.91 (d, 2H), 7.02 (d, 2H), 7.46 (m, 3H), 7.59 (m, 4H), 7.91 (d, 2H), 9.45 (s, 1H) | DMSO-$d_6$ | — |
| 34 | N-hydroxy-4-5-[4-(5-butyl-2-pyridin-3-yl-1,3-thiazol-4-yl)phenoxy]pentoxy-benzamidine | Hexanoylchloride | Thionicotinamide | | 0.86 (t, 3H), 1.35 (m, 2H), 1.59 (m, 2H), 1.66 (m, 2H), 1.78 (m, 4H), 2.95 (t, 2H), 4.03 (m, 4H), 5.75 (brs, 2H), 6.91 (d, 2H), 7.04 (d, 2H), 7.51 (m, 1H), 7.58 (m, 4H), 8.26 (d, 1H), 8.63 (d, 1H), 9.09 (d, 1H), 9.45 (s, 1H) | DMSO-$d_6$ | 107-118 |
| 35 | N-hydroxy-4-5-[4-(5-butyl-2-cyclohexyl-1,3-thiazol-4-yl)phenoxy]pentoxy-benzamidine | Hexanoylchloride | Cyclohexanecarbothioic acid amide | | 0.84 (t, 3H), 1.28 (brm, 6H), 1.56 (brm, 6H), 1.77 (brm, 6H), 2.00 (m, 2H), 2.83 (t, 2H), 2.90 (m, 1H), 4.01 (m, 4H), 5.72 (s, 2H), 6.91 (d, 2H), 6.98 (d, 2H), 7.47 (d, 2H), 7.57 (d, 2H), 9.44 (s, 1H) | DMSO-$d_6$ | — |
| 36 | N-hydroxy-4-5-[4-(5-butyl-2-pentyl-1,3-thiazol-4-yl)phenoxy]pentoxy-benzamidine | Hexanoylchloride | Thiohexanoamide | | 0.85 (m, 6H), 1.31 (m, 2H), 1.58 (m, 4H), 1.69 (m, 2H), 1.78 (brm, 4H), 2.83 (t, 2H), 2.88 (t, 2H), 4.01 (m, 4H), 5.72 (brs, 2H), 6.91 (d, 2H), 6.98 (d, 2H), 7.47 (d, 2H), 7.57 (d, 2H), 9.44 (s, 1H) | DMSO-$d_6$ | — |
| 37 | N-hydroxy-4-5-[4-(5-butyl-2-t-butyl-1,3-thiazol-4- | Hexanoylchloride | 2,2-dimethylthio-propionamide | | 0.84 (t, 3H), 1.31 (m, 2H), 1.36 (s, 9H), 1.57 (brm, 4H), 1.79 (brm, 4H), 2.83 (m, 2H), 4.01 (m, 4H), 5.74 (brs, 2H), 6.91 (d, 2H), | DMSO-$d_6$ | — |

TABLE 1-continued

| example | name | Acid chloride | Thioamide | Alkylhalide | NMR | solvent | mp |
|---|---|---|---|---|---|---|---|
| | yl)phenoxy]pentoxy-benzamidine | | | | 6.97 (d, 2H), 7.48 (d, 2H), 7.58 (d, 2H), 9.45 (s, 1H) | | |
| 38 | N-hydroxy-4-5-[4-(5-benzyl-2-methyl-1,3-thiazol-4-yl)phenoxy]pentoxy-benzamidine | Hydrocinnamoyl chloride | Thioaectamide | | 1.56 (m, 2H), 1.78 (brm, 4H), 2.58 (s, 3H), 4.00 (m, 4H), 4.20 (s, 2H), 5.77 (brs, 2H), 6.91 (d, 2H), 6.98 (d, 2H), 7.17 (d, 2H), 7.22 (m, 1H), 7.30 (m, 2H), 7.52 (d, 2H), 7.57 (d, 2H), 9.47 (s, 1H) | DMSO-d$_6$ | — |
| 39 | N-hydroxy-4-5-[4-(5-benzyl-2-isopropyl-1,3-thiazol-4-yl)phenoxy]pentoxy-benzamidine | Hydrocinnamoyl chloride | Thioisobutramide | | 1.28 (d, 6H), 1.57 (m, 2H), 1.77 (brm, 4H), 3.19 (m, 1H), 4.00 (m, 2H), 4.21 (s, 2H), 5.70 (s, 2H), 6.90 (d, 2H), 6.98 (d, 2H), 7.19 (m, 3H), 7.30 (m, 2H), 7.53 (d, 2H), 7.56 (d, 2H), 9.44 (s, 1H) | DMSO-d$_6$ | 108-120 |
| 40 | N-hydroxy-4-5-[4-(5-benzyl-2-phenyl-1,3-thiazol-4-yl)phenoxy]pentoxy-benzamidine | Hydrocinnamoyl chloride | Thiobenzamide | | 1.58 (m, 2H), 1.79 (brm, 4H), 4.02 (m, 4H), 4.31 (s, 2H), 5.72 (brs, 2H), 6.91 (d, 2H), 7.03 (d, 2H), 7.24 (m, 3H), 7.32 (m, 2H), 7.46 (m, 3H), 7.58 (d, 2H), 7.64 (d, 2H), 7.89 (m, 2H), 9.44 (s, 2H) | DMSO-d$_6$ | — |
| 41 | N-hydroxy-4-5-[4-(5-benzyl-2-pyridin-3-yl-1,3-thiazol-4-yl)phenoxy]pentoxy-benzamidine | hydrocinnamoyl chloride | thionicotinamide | | 1.58 (m, 2H), 1.79 (brm, 4H), 4.02 (m, 4H), 4.34 (s, 2H), 5.73 (brs, 2H), 6.91 (d, 2H), 7.04 (d, 2H), 7.25 (m, 3H), 7.33 (,. 2H), 7.49 (m, 1H), 7.58 (d, 2H), 7.66 (d, 2H), 8.25 (d, 1H), 8.63 (d, 1H), 9.08 (s, 1H), 9.45 (s, 1H) | DMSO-d$_6$ | 134-143 |
| 42 | N-hydroxy-4-(5-[4-(5-(2-chloro-ethyl)-2-methyl-1,3-thiazol-4-yl]phenoxy)pentoxy)-benzamidine | 4-chloro-butyrylchloride | thioacetamide | | 1.65 (m, 2H), 1.86 (m, 4H), 2.72 (s, 3H), 3.30 (t, 2H), 3.67 (t, 2H), 4.02 (m, 4H), 5.70 (s, 2H), 6.92 (m, 4H), 7.45 (d, 2H), 9.43 (s, 1H) | DMSO-d$_6$ | |
| 43 | N-hydroxy-4-(5-[4-(5-cyclopentyl-2methyl-1,3-thiazol-4-yl)phenoxy]pentoxy)-benzamidine | cyclopentyl acetylchloride | thioacetamide | | 1.58 (brs, 6H), 1.77 (brs, 6H), 2.07 (brs, 2H), 2.62 (s, 3H), 3.30 (m, 1H), 3.98 (m, 4H), 6.75-6.92 (m, 4H), 7.39-7.60 (m, 4H) | CDCl$_3$ | |
| 44 | N-hydroxy-4-(5-[4-(5-isobutyl-2-methyl-1,3-thiazol-4-yl)phenoxy]pentoxy)-benzamidine | isocaproic chloride | thioacetamide | | 0.86 (d, 6H), 1.60 (m 2H), 1.78 (m, 5H), 2.61 (s, 2H), 2.72 (d, 2H), 4.01 (m, 4H), 5.77 (s, 2H), 6.91 (d, 2H), 6.98 (d, 2H), 7.45 (d, 2H), 7.59 (d, 2H), 9.47 (s, 1H) | DMSO-d$_6$ | |
| 45 | N-hydroxy-4-5-[4-(5-cyclopentylmethyl-2-methyl-1,3-thiazol-4-yl)phenoxy]pentoxy-benzamidine | cyclopentyl-propionylchloride | thioacetamide | | 1.14 (m, 2H), 1.48 (brm 6H), 1.69 (m, 2H), 1.78 (brm, 4H), 2.02 (m, 1H), 2.59 (s, 3H), 2.82 (d, 2H), 4.00 (m, 4H), 5.70 (s, 2H), 6.90 (d, 2H), 6.97 (d, 2H), 7.46 (d, 2H), 7.57 (d, 2H), 9.44 (s, 1H) | DMSO-d$_6$ | — |
| 46 | N-hydroxy-4-5-[4-(5-cyclopentylmethyl-2-ethyl-1,3-thiazol-4-yl)phenoxy]pentoxy-benzamidine | cyclopentyl-propionylchloride | thiopropionamide | | 1.11 (m, 2H), 1.27 (t, 3H), 1.52 (brm, 6H), 1.70 (m, 2H), 1.78 (brm, 4H), 2.03 (m, 1H), 2.83 (d, 2H), 2.92 (q, 2H), 4.00 (m, 4H), 5.70 (s, 2H), 6.91 (d, 2H), 6.98 (d, 2H), 7.46 (d, 2H), 7.79 (d, 2H), 9.44 (s, 1H) | DMSO-d$_6$ | — |
| 47 | N-hydroxy-4-5-[4-(5-cyclopentylmethyl-2-isopropyl-1,3-thiazol-4-yl)phenoxy]pentoxy-benzamidine | cyclopentyl-propionylchloride | thioisobutramide | | 1.11 (m, 2H), 1.31 (d, 6H), 1.49 (brm, 6H), 1.78 (brm, 6H), 2.04 (m, 1H), 2.83 (d, 2H), 3.21 (m, 1H), 4.01 (m, 4H), 5.72 (brs, 2H), 6.91 (d, 2H), 6.98 (d, 2H), 7.47 (d, 2H), 7.57 (d, 2H), 9.44 (s, 1H) | DMSO-d$_6$ | — |
| 48 | N-hydroxy-4-5-[4-(5-cyclopentylmethyl-2-phenyl-1,3-thiazol-4-yl)phenoxy]pentoxy-benzamidine | cyclopentyl-propionylchloride | thiobenzamide | | 1.15 (m, 2H), 1.50 (brm, 6H), 1.78 (brm, 6H), 2.11 (m, 1H), 2.92 (d, 2H), 4.01 (m, 4H), 5.71 (s, 2H), 6.91 (d, 2H), 7.02 (d, 2H), 7.46 (m, 3H), 7.58 (m, 4H), 7.91 (dd, 2H), 9.44 (s, 1H) | DMSO-d$_6$ | — |

TABLE 1-continued

| example | name | Acid chloride | Thioamide | Alkylhalide | NMR | solvent | mp |
|---|---|---|---|---|---|---|---|
| 49 | N-hydroxy-4-5-[4-(5-cyclopentylmethyl-2-pyridin-3-yl-1,3-thiazol-4-yl)phenoxy]pentoxy-benzamidine | cyclopentyl-propionylchloride | thionicotinamide | | 1.16 (m, 2H), 1.55 (brm, 6H), 1.78 (brm, 6H), 2.12 (m, 1H), 2.96 (d, 2H), 4.02 (m, 4H), 5.71 (brs, 2H), 6.91 (d, 2H), 7.04 (d, 2H), 7.52 (m, 1H), 7.58 (m, 4H), 8.26 (m, 1H), 8.64 (dd, 1H), 9.10 (d, 1H), 9.44 (s, 1H) | DMSO-$d_6$ | — |
| 50 | N-hydroxy-4-5-[4-(5-cyclopentylmethyl-2-cyclohexyl-1,3-thiazol-4-yl)phenoxy]pentoxy-benzamidine | cyclopentyl-propionylchloride | Cyclohexanecarbothioic acid amide | | 1.10 (m, 2H), 1.23 (m, 1H), 1.46 (brm, 11H), 1.77 (brm, 8H), 2.02 (m, 3H), 2.83 (d, 2H), 2.90 (m, 1H), 4.00 (m, 4H), 5.71 (s, 2H), 6.91 (d, 2H), 6.97 (d, 2H), 7.46 (d, 2H), 7.57 (d, 2H), 9.44 (s, 1H) | DMSO-$d_6$ | |
| 51 | N-hydroxy-4-5-[4-(5-cyclopentylmethyl-2-pentyl-1,3-thiazol-4-yl)phenoxy]pentoxy-benzamidine | cyclopentyl-propionylchloride | thiohexanoamide | | 0.85 (t, 3H), 1.10 (m, 2H), 1.31 (brm, 4H), 1.52 (brm, 6H), 1.58 (brm, 4H), 1.70 (brm, 4H), 2.03 (m, 1H), 2.83 (d, 2H), 2.89 (m, 2H), 4.01 (m, 4H), 5.71 (s, 2H), 6.91 (d, 2H), 6.98 (d, 2H), 7.46 (d, 2H), 7.57 (d, 2H), 9.44 (s, 1H) | DMSO-$d_6$ | |
| 57 | N-hydroxy-4-5-[4-(2-amino-1,3-thiazol-4-yl)phenoxy]pentoxy-benzamidine | acetylchloride | thiourea | | 1.56 (m, 2H), 1.77 (m, 4H), 3.98 (m, 4H), 5.72 (s, 2H), 6.80-6.99 (m, 7H), 7.58 (d, 2H), 7.69 (d, 2H), 9.46 (s, 1H) | DMSO-$d_6$ | |
| 58 | N-hydroxy-4-5-[4-(2-amino-5-methyl-1,3-thiazol-4-yl)phenoxy]pentoxy-benzamidine | propionylchloride | thiourea | | 1.57 (m, 2H), 1.77 (m, 4H), 2.27 (s, 3H), 3.99 (m, 4H), 5.72 (s, 2H), 6.70 (s, 2H), 6.91 (m, 4H), 7.45 (d, 2H), 7.57 (d, 2H), 9.44 (s, 1H) | DMSO-$d_6$ | |
| 59 | N-hydroxy-4-5-[4-(2-guanidino-5-methyl-1,3-thiazol-4-yl)phenoxy]pentoxy-benzamidine | propionylchloride | amidino thiourea | | 1.56 (m, 2H), 1.78 (m, 4H), 2.30 (s, 3H), 4.00 (t, 4H), 5.71 (s, 2H), 6.91 (d, 2H), 6.94 (d, 2H), 7.47 (d, 2H), 7.57 (d, 2H), 9.44 (s, 1H) | DMSO-$d_6$ | |
| 60 | N-hydroxy-4-5-[4-(2-amino-5-ethyl-1,3-thiazol-4-yl)phenoxy]pentoxy-benzamidine | butrylchloride | thiourea | | 1.15 (t, 3H), 1.57 (m, 2H), 1.76 (m, 4H), 2.68 (q, 2H), 3.99 (m, 4H), 5.69 (s, 2H), 6.72 (s, 2H), 6.91 (m, 4H), 7.39 (d, 2H), 7.57 (d, 2H), 9.43 (s, 1H) | DMSO-$d_6$ | |
| 61 | N-hydroxy-4-5-[4-(2-amino-5-isopropyl-1,3-thiazol-4-yl)phenoxy]pentoxy-benzamidine | isovalerylchloride | thiourea | | 1.17 (d, 6H), 1.56 (m, 2H), 1.78 (m, 3H), 3.20 (m, 1H), 4.00 (m, 4H), 5.70 (brm, 1H), 6.91 (m, 4H), 7.35 (m, 2H), 7.57 (m, 2H), 9.43 (s, 1H) | DMSO-$d_6$ | |
| 62 | N-hydroxy-4-5-[4-(2-guanidino-5-isopropyl-1,3-thiazol-4-yl)phenoxy]pentoxy-benzamidine | isovalerylchloride | amidino thiourea | | 1.17 (d, 6H), 1.56 (brm, 2H), 1.77 (brm, 4H), 3.22 (m, 1H), 4.00 (m, 4H), 5.71 (s, 2H), 6.93 (m, 5H), 7.38 (d, 2H), 7.57 (d, 2H), 9.44 (s, 1H) | DMSO-$d_6$ | |
| 63 | N-hydroxy-4-5-[4-(2-amino-5-butyl-1,3-thiazol-4-yl)phenoxy]pentoxy-benzamidine | hexanoylchloride | thiourea | | 0.83 (t, 3H), 1.30 (m, 2H), 1.48 (m, 2H), 1.56 (m, 2H), 1.77 (brm, 4H), 2.65 (t, 2H), 3.99 (m, 4H), 5.73 (brs, 2H), 6.72 (s, 2H), 6.91 (m, 4H), 7.38 (d, 2H), 7.57 (d, 2H), 9.45 (s, 1H) | DMSO-$d_6$ | |
| 64 | N-hydroxy-4-5-[4-(5-butyl-2-guanidino-1,3-thiazol-4-yl)phenoxy]pentoxy-benzamidine | hexanoylchloride | amidino thiourea | | 0.83 (t, 3H), 1.28 (m, 2H), 1.53 (m, 4H), 1.78 (m, 4H), 2.69 (m, 2H), 4.00 (m, 4H), 5.73 (brs, 2H), 6.91 (m, 4H), 6.95 (d, 2H), 7.42 (d, 2H), 7.57 (d, 2H), 9.45 (s, 1H) | DMSO-$d_6$ | |
| 65 | N-hydroxy-4-5-[4-(2-amino-5-benzyl-1,3-thiazol-4-yl)phenoxy]pentoxy-benzamidine | hydrocinnamoyl chloride | thiourea | | 1.55 (brm,, 2H), 1.77 (brm, 4H), 3.98 (m, 4H), 4.02 (s, 1H), 5.79 (s, 2H), 6.79 (s, 2H), 6.91 (m, 4H), 7.19 (m, 3H), 7.29 (m, 2H), 7.43 (d, 2H), 7.57 (d, 2H), 9.47 (s, 1H) | DMSO-$d_6$ | |
| 66 | N-hydroxy-4-5-[4-(5-benzyl-2- | hydrocinnamoyl chloride | amidino thiourea | | 1.55 (m, 2H), 1.77 (brm, 4H), 4.99 (m, 4H), 4.05 (s, 2H), 5.71 (s, | DMSO-$d_6$ | |

TABLE 1-continued

| example | name | Acid chloride | Thioamide | Alkylhalide | NMR | solvent | mp |
|---|---|---|---|---|---|---|---|
|  | guanidino-1,3-thiazol-4-yl)phenoxy]pentoxy-benzamidine |  |  |  | 2H), 4.92 (m, 4H), 7.19 (m, 3H), 7.29 (m, 2H), 7.45 (d, 2H), 7.57 (d, 2H), 9.44 (s, 1H) |  |  |
| 67 | N-hydroxy-4-5-[4-(2-amino-5-cyclopentylmethyl-1,3-thiazol-4-yl)phenoxy]pentoxy-benzamidine | cyclopentyl-propionylchloride | thiourea |  | 1.09 (brm, 2H), 1.48 (brm, 4H), 1.56 (m, 2H), 1.69 (m, 2H), 1.77 (brm, 4H), 1.97 (m, 1H), 2.65 (d, 2H), 3.98 (m, 4H), 5.70 (s, 2H), 6.72 (s, 2H), 6.90 (m, 4H), 7.38 (d, 2H), 7.57 (d, 2H), 9.44 (s, 1H) | DMSO-d$_6$ |  |
| 68 | N-hydroxy-4-5-[4-(5-cyclopentylmethyl-2-(1-propyl-piperidin-4-yl)-1,3-thiazol-4-yl)phenoxy]pentoxy-benzamidine | cyclopentyl-propionylchloride | piperidin-4-carbothioic acid amide | propyl-bromide | 0.84 (t, 3H), 1.11 (m, 2H), 1.43-1.78 (brm, 17H), 2.04 (m, 4H), 2.24 (m, 2H), 2.85 (m, 5H), 4.01 (m, 4H), 5.70 (s, 2H), 6.90 (d, 2H), 6.98 (d, 2H), 7.47 (d, 2H), 7.57 (d, 2H), 9.44 (s, 1H) | DMSO-d$_6$ |  |
| 69 | N-[4-(4-(5-[4-(N-hydroxy carbamimidoyl-phenoxy)pentoxy]-phenyl]-5-methyl-thiazol-2-ylmethyl)-isobutylamide | propionylchloride | N-2(amino-2-thioxoethyl)-2-methyl propanamide |  | 1.11 (d, 6H), 1.59 (m, 2H), 1.79 (m, 4H), 2.42 (s, 3H), 2.72 (m, 1H), 4.02 (m, 4H), 5.72 (s, 2H), 6.93 (d, 2H), 7.00 (d, 2H), 7.56 (m, 4H), 9.45 (s, 1H), 12.00 (s, 1H) | DMSO-d$_6$ |  |
| 70 | N-hydroxy-4-5-[4-(5-isopropyl-2-morpholinomethyl-1,3-thiazol-4-yl)phenoxy]pentoxy-benzamidine | isovalerylchloride | glycine thioamide | bis-(dibromide)-ethylester | 1.25 (d, 6H), 1.58 (m, 2H), 1.80 (m, 4H), 2.50 (m, 4H), 3.33 (m, 1H), 3.60 (m, 4H), 3.76 (s, 2H), 4.01 (m, 4H), 5.70 (s, 2H), 7.00 (m, 4H), 7.45 (d, 2H), 7.60 (d, 2H), 9.44 (s, 1H) | DMSO-d$_6$ |  |
| 71 | N-hydroxy-4-5-[4-(2-aminomethyl-5-benzyl-1,3-thiazol-4-yl)phenoxy]pentoxy-benzamidine | hydrocinnamoyl chloride | glycine thioamide |  | 1.56 (m, 2H), 1.78 (brm, 4H), 3.92 (s, 2H), 4.00 (m, 4H), 4.21 (s, 2H), 5.70 (s, 2H), 6.90 (d, 2H), 6.97 (d, 2H), 7.21 (m, 3H), 7.30 (m, 2H), 7.52 (d, 2H), 7.57 (d, 2H), 9.44 (s, 1H) | DMSO-d$_6$ |  |
| 72 | N-hydroxy-4-5-[4-(5-methyl-2-(1-propyl-piperidin-4yl)-1,3-thiazol-4-yl)phenoxy]pentoxy-benzamidine | propionylchloride | piperidin-4-carbothioic acid amide | propyl-bromide | 0.84 (t, 3H), 1.42 (m, 2H), 1.56 (m, 2H), 1.67 (m, 2H), 1.78 (brm, 4H), 2.00 (m, 4H), 2.24 (m, 2H), 2.46 (s, 3H), 2.89 (m, 3H), 4.00 (m, 4H), 5.71 (m, 2H), 6.90 (d, 2H), 6.98 (d, 2H), 7.56 (m, 4H), 9.44 (s, 1H) | DMSO-d$_6$ |  |
| 73 | N-hydroxy-4-5-[4-(5-isopropyl-2-aminomethyl-1,3-thiazol-4-yl)phenoxy]pentoxy-benzamidine | isovalerylchloride | 2-amino-thioacetamide |  | 1.25 (d, 6H), 1.57 (m, 2H), 1.79 (m, 4H), 3.35 (m, 1H), 3.96-4.04 (m, 6H), 5.74 (s, 2H), 6.91 (d, 2H), 6.98 (d, 2H), 7.93 (d, 2H), 7.58 (d, 2H) | DMSO-d$_6$ |  |
| 74 | N-hydroxy-4-5-[4-(5-vinyl-2-methyl-1,3-thiazol-4-yl)phenoxy]pentoxy-benzamidine | 4-chlorobutryl chloride | thioacetamide |  | 1.61 (m, 2H), 1.81 (m, 4H), 2.66 (s, 3H), 3.95 (m, 4H), 5.16 (s, 1H), 5.17 (d, 1H), 5.42 (d, 1H), 6.84 (m, 3H), 6.92 (d, 2H), 7.51 (d-d, 4H) | CDCl$_3$ |  |
| 75 | N-hydroxy-4-5-[4-(5-hydroxymethyl-2-methyl-1,3-thiazol-4-yl)phenoxy]pentoxy-benzamidine | methoxyacetyl chloride | thioacetamide |  | 1.58 (m, 2H), 1.79 (m, 4H), 2.63 (s, 3H), 4.01 (m, 4H), 4.12 (t, 1H), 4.67 (m, 2H), 5.70 (brs, 2H), 6.98 (m, 2H), 7.50 (m, 2H), 7.58 (m, 2H), 8.23 (s, 1H) |  |  |
| 76 | N-hydroxy-4-5-[4-(5-methoxymethyl-2-methyl-1,3-thiazol-4-yl)phenoxy]pentoxy-benzamidine | methoxyacetyl chloride | thioacetamide |  | 1.57 (m, 2H), 1.80 (m, 4H), 2.65 (s, 3H), 3.32 (s, 3H), 4.01 (m, 4H), 4.58 (s, 2H), 6.93 (m, 2H), 7.01 (m, 2H), 7.56 (m, 4H), 9.45 (brs, 1H) |  |  |
| 77 | N-hydroxy-4-5-[4-(5-(2-chloroethyl)-2-amino-1,3-thiazol-4-yl)phenoxy]pentoxy-benzamidine | 4-chlorobutryl chloride | thiourea |  | 1.57 (m, 2H), 1.79 (m, 4H), 3.36 (m, 2H), 3.77 (m, 2H), 4.00 (m, 4H), 5.73 (s, 2H), 6.91 (m, 2H), 7.42 (d, 2H), 7.58 (d, 2H), 9.47(s, 1H) | DMSO-d$_6$ |  |
| 78 | N-hydroxy-4-5-[4-(5-vinyl-2-amino-1,3-thiazol-4-yl | 4-chlorobutryl chloride | thiourea |  | 1.58 (m, 2H), 1.79 (m, 4H), 4.01 (m, 4H), 6.82-7.75 (m, 11H) | DMSO-d$_6$ |  |

TABLE 1-continued

| example | name | Acid chloride | Thioamide | Alkylhalide | NMR | solvent | mp |
|---|---|---|---|---|---|---|---|
| 79 | N-hydroxy-4-5-[4-(5-vinyl-2-(pyridin-3-yl)-1,3-thiazol-4-yl)phenoxy]pentoxy-benzamidine | 4-chlorobutryl chloride | thionicotinamide | | 1.59 (m, 2H), 1.81 (m, 4H), 4.05 (m, 4H), 5.44 (d, 1H), 5.71 (d, 1H), 5.85 (brs, 2H), 6.94 (m, 3H), 7.07 (m, 2H), 7.61 (m, 4H), 8.33 (m, 1H), 8.68 (m, 1H), 9.16 (brs, 1H), 9.52 (brs, 1H) | DMSO-$d_6$ | |
| 80 | N-hydroxy-4-5-[4-(5-(2-chloroethyl)-2-(pyridin-3-yl)-1,3-thiazol-4-yl)phenoxy]pentoxy-benzamidine | 4-chlorobutryl chloride | thionicotinamide | | 1.60 (m, 2H), 1.81 (m, 4H), 3.44 (m, 2H), 3.94 (m, 2H), 4.02-4.06 (m, 4H), 5.75 (brs, 2H), 6.91 (m, 2H), 7.06 (m, 2H), 7.61 (m, 4H), 8.30 (m, 1H), 8.68 (m, 1H), 9.13 (m, 1H), 9.46 (m, 1H) | DMSO-$d_6$ | |
| 81 | N-hydroxy-4-5-[4-(2-amino-5-cyclopentyl-1,3-thiazol-4-yl)phenoxy]pentoxy-benzamidine | cyclopentylacetyl chloride | thiourea | | 1.40 (m, 2H), 1.55-1.59 (m, 4H), 1.77-1.81 (m, 6H), 2.01 (m, 2H), 3.22-3.31 (m, 1H), 4.00-4.02 (m, 4H), 5.72 (s, 2H), 6.92 (m, 4H), 7.57 (d, 2H), 7.83 (d, 2H) | DMSO-$d_6$ | |
| 82 | N-hydroxy-4-5-[4-(5-ethyl-2-aminomethyl-1,3-thiazol-4-yl)phenoxy]pentoxy-benzamidine | butrylchloride | 2-amino-thioacetamide | | 1.21 (t, 3H), 1.58 (m, 2H), 1.78 (m, 4H), 2.85 (q, 2H), 3.93 (s, 2H), 4.00 (m, 4H), 5.70 (s, 2H), 6.90 (d, 2H), 6.97 (d, 2H), 7.48 (d, 2H), 7.58 (d, 2H), 9.43 (s, 1H) | DMSO-$d_6$ | |
| 83 | N-hydroxy-4-5-[4-(5-isopropyl-2-(piperidin-3-yl)-1,3-thiazol-4-yl)phenoxy]pentoxy-benzamidine | isovalerylchloride | piperidin-3-carbothioic acid amide | | 1.25 (d, 6H), 1.57 (m, 2H), 1.80 (m, 4H), 1.91 (m, 2H), 2.17 (m, 2H), 3.05 (m, 2H), 3.37 (m, 4H), 4.02-4.09 (m, 4H), 7.00 (d, 2H), 7.13 (d, 2H), 7.44 (d, 2H), 7.67 (d, 2H) | DMSO-$d_6$ | |

2. Benzamidine ($R_5$=H)

Examples 52 to 56

Compound (12) prepared according to the same method as that in the Preparative Example 1-6 was reacted in the same manner as Example 2, obtaining the title compounds shown I Table 2.

Table 2 shows the title compounds, reactants and $^1$H-NMR data.

TABLE 2

| example | name | Acid chloride | Thioamide | Alkylhalide | NMR | solvent | mp |
|---|---|---|---|---|---|---|---|
| 52 | 4-5-[4-(2-methyl-1,3-thiazol-4-yl)phenoxy]pentoxy-benzamidine | acetylchloride | thioacetamide | | 1.57 (brm, 2H), 1.79 (brm, 4H), 2.68 (s, 3H), 4.01 (t, 2H), 4.11 (t, 2H), 6.96 (d, 2H), 7.13 (d, 2H), 7.81 (m, 4H) | DMSO-$d_6$ | |
| 53 | 4-5-[4-(2-isopropyl-1,3-thiazol-4-yl)phenoxy]pentoxy-benzamidine | acetylchloride | thioisobutramide | | 1.35 (d, 6H), 1.56 (brm, 2H), 1.78 (brm, 4H), 3.30 (m, 1H), 4.02 (m, 4H), 6.95 (m, 4H), 7.77 (s, 1H), 7.83 (m, 4H) | DMSO-$d_6$ | |
| 54 | 4-5-[4-(2,5-dimethyl-1,3-thiazol-4-yl)phenoxy]pentoxy-benzamidine | propionylchloride | thioacetamide | | 1.57 (brm, 2H), 1.79 (brm, 4H), 2.68 (s, 3H), 4.01 (t, 2H), 4.11 (t, 2H), 6.96 (d, 2H), 7.12 (d, 2H), 7.73 (s, 1H), 7.81 (m, 4H) | DMSO-$d_6$ | |
| 55 | 4-5-[4-(5-ethyl-2-isopropyl-1,3-thiazol-4-yl)phenoxy]pentoxy-benzamidine | butrylchloride | thioisobutramide | | 1.32 (d, 6H), 1.59 (m, 2H), 1.79 (m, 4H), 2.47 (s, 3H), 3.21 (m, 1H), 4.02 (t, 2H), 4.09 (t, 2H), 6.98 (d, 2H), 7.09 (d, 2H), 7.55 (d, 2H), 7.74 (d, 2H) | DMSO-$d_6$ | |

TABLE 2-continued

| example | name | Acid chloride | Thioamide | Alkylhalide | NMR | solvent | mp |
|---|---|---|---|---|---|---|---|
| 56 | 4-5-[4-(5-ethyl-2-phenyl-1,3-thiazol-4-yl)phenoxy]pentoxy-benzamidine | butrylchloride | thiobenzamide | | 1.29 (t, 3H), 1.59 (m, 2H), 1.81 (brm, 4H), 2.95 (q, 2H), 4.04 (t, 2H), 4.11 (t, 2H0, 7.03 (d, 2H), 7.15 (d, 2H), 7.47 (m, 3H), 7.59 (d, 2H), 7.84 (d, 2H), 7.91 (m, 2H) | DMSO-$d_6$ | |

Examples 84 to 117

Compound (16) prepared according to the same method as that in the Preparative Example 2-2 was reacted in the same manner as Example 1, obtaining the title compounds shown I Table 3.

Table 3 shows the title compounds, reactants and $^1$H-NMR data.

TABLE 3

| example | name | Acid chloride | Thioamide | Alkylhalide | NMR | solvent | mp |
|---|---|---|---|---|---|---|---|
| 84 | N-hydroxy-4-5-[4-(2-ethylamino-1,3-thiazol-4-yl)phenoxy]pentoxy-benzamidine | acetylchloride | thiourea | iodoethane | 1.17 (t, 3H), 1.55 (brm, 2H), 1.77 (brm, 2H), 3.25 (m, 2H), 3.99 (m, 4H), 5.73 (s, 2H), 6.84 (m, 1H), 6.90 (m, 2H), 7.57 (d, 2H), 7.71 (d, 2H) | DMSO-$d_6$ | |
| 85 | N-hydroxy-4-5-[4-(2-ethansulfonylamino-1,3-thiazol-4-yl)phenoxy]pentoxy-benzamidine | acetylchloride | thiourea | ethansulfonylchloride | 1.20 (t, 3H), 1.55 (brm, 2H), 1.77 (brm, 4H), 3.02 (q, 2H), 4.00 (m, 4H), 5.77 (brm, 2H), 6.91 (d, 2H), 6.98 (d, 2H), 7.00 (s, 1H), 7.57 (d, 2H), 7.65 (d, 2H), 9.47 (brs, 1H), 12.86 (s, 1H) | DMSO-$d_6$ | |
| 86 | N-hydroxy-4-5-[4-(5-methyl-2-methylamino-1,3-thiazol-4-yl)phenoxy]pentoxy-benzamidine | propionylchloride | thiourea | iodomethane | 1.56 (m, 2H), 1.77 (m, 4H), 2.29 (s, 3H), 2.77 (d, 3H), 3.99 (m, 4H), 5.72 (s, 2H), 6.91 (m, 4H), 7.22 (m, 1H), 7.48 (d, 2H), 7.50 (d, 2H), 9.44 (s, 1H) | DMSO-$d_6$ | |
| 87 | N-hydroxy-4-5-[4-(2-ethylamino-5-methyl-1,3-thiazol-4-yl)phenoxy]pentoxy-benzamidine | propionylchloride | thiourea | iodoethane | 1.12 (t, 3H), 1.56 (m, 2H), 1.78 (m, 4H), 2.28 (s, 3H), 3.18 (p, 2H), 3.99 (t, 4H), 5.72 (s, 2H), 6.94 (m, 4H), 7.27 (t, 1H), 7.47 (d, 2H), 7.57 (d, 2H), 9.44 (s, 1H) | DMSO-$d_6$ | |
| 88 | N-hydroxy-4-5-[4-(5-methyl-2-propylamino-1,3-thiazol-4-yl)phenoxy]pentoxy-benzamidine | propionylchloride | thiourea | propylbromide | 0.89 (t, 3H), 1.54 (m, 4H), 1.78 (m, 4H), 2.28 (s, 3H), 3.12 (m, 2H), 3.99 (m, 4H), 5.72 (s, 1H), 6.92 (m, 4H), 7.32 (t, 1H), 7.47 (d, 2H), 7.57 (d, 2H), 9.44 (s, 1H) | DMSO-$d_6$ | |
| 89 | N-hydroxy-4-5-[4-(5-cyclopentylmethyl-2-(3-pyridylcarbonyl)amino-1,3-thiazol-4-yl)phenoxy]pentoxy-benzamidine | cyclopentyl-propionylchloride | thiourea | niconoylchloride | 1.15 (m, 2H), 1.57 (brm, 6H), 1.77 (brm, 6H), 2.10 (m, 1H), 2.85 (d, 2H), 4.00 (m, 4H), 5.72 (brs, 2H), 6.91 (d, 2H), 7.00 (d, 2H), 7.51 (d, 2H), 7.58 (d, 2H), 7.38 (m, 1H), 8.40 (d, 1H), 8.77 (d, 1H), 9.19 (s, 1H), 9.44 (s, 1H), 12.83 (s, 1H) | DMSO-$d_6$ | |
| 90 | N-hydroxy-4-5-[4-(2-hydroxyacetylamino-5-methyl-1,3-thiazol-4-yl)phenoxy]pentoxy-benzamidine | propionylchloride | thiourea | acetoxyacetyl chloride | 1.56 (brm, 2H), 1.78 (brm, 4H), 2.42 (s, 3H), 4.01 (m, 4H), 4.10 (d, 2H), 5.47 (t, 1H), 5.73 (brs, 2H), 6.92 (d, 2H), 6.98 (d, 2H), 7.55 (m, 4H), 9.45 (s, 1H), 11.67 (s, 1H) | DMSO-$d_6$ | |
| 91 | N-hydroxy-4-5-[4-(5-methyl-2-(4-pyridylcarbonyl)amino-1,3-thiazol-4-yl)phenoxy]pentoxy-benzamidine | propionylchloride | thiourea | isoniconoylchloride | 1.57 (brm, 4H), 1.79 (brm, 4H), 2.48 (s, 3H), 4.02 (m, 4H), 5.73 (brm, 2H), 6.91 (d, 2H), 7.01 (d, 2H), 7.58 (d, 4H), 7.98 (dd, 2H), 8.78 (dd, 2H), 9.45 (s, 1H) | DMSO-$d_6$ | |
| 92 | N-hydroxy-4-5-[4-(5-methyl-2-(3-pyridylcarbonyl)amino- | propionylchloride | thiourea | niconoylchloride | 1.58 (m, 2H), 1.79 (m, 4H), 2.46 (s, 3H), 4.01 (m, 4H), 5.74 (s, 2H), 6.91 (d, 2H), | DMSO-$d_6$ | |

TABLE 3-continued

| example | name | Acid chloride | Thioamide | Alkylhalide | NMR | solvent | mp |
|---|---|---|---|---|---|---|---|
| | 1,3-thiazol-4-yl)phenoxy]pentoxy-benzamidine | | | | 7.00 (d, 2H), 7.57 (m, 4H), 8.41 (d, 1H), 8.77 (d, 1H), 9.20 (d, 1H), 9.46 (brs, 1H), 12.80 (brs, 1H) | | |
| 93 | N-hydroxy-4-5-[4-(2-ethansulfonylamino-5-methyl-1,3-thiazol-4-yl)phenoxy]pentoxy-benzamidine | propionylchloride | thiourea | ethansulfonylchloride | 0.94 (t, 3H), 1.56 (m, 2H), 1.78 (brm, 4H), 2.18 (s, 3H), 2.98 (q, 2H), 4.01 (m, 4H), 5.73 (s, 2H), 6.90 (d, 2H), 7.01 (d, 2H), 7.38 (d, 2H), 7.57 (d, 2H), 9.44 (s, 1H), 12.52 (s, 1H) | DMSO-$d_6$ | |
| 94 | N-hydroxy-4-(5-4-[2-(2-methoxyethyl)amino-5-methyl-1,3-thiazol-4-yl]phenoxypentoxy)-benzamidine | propionylchloride | thiourea | 2-chloroethylmethylester | 1.58 (m, 2H), 1.80 (m, 4H), 2.30 (s, 3H), 3.26 (s, 3H), 3.39 (m, 2H), 3.37 (m, 2H), 4.01 (m, 4H), 5.71 (s, 2H), 6.90 (d, 2H), 6.96 (d, 2H), 7.48 (d, 2H), 7.58 (d, 2H), 9.44 (s, 1H) | DMSO-$d_6$ | |
| 95 | N-hydroxy-4-5-[4-(2-ethansulfonylamino-5-ethyl-1,3-thiazol-4-yl)phenoxy]pentoxy-benzamidine | butrylchloride | thiourea | ethansulfonylchloride | 1.13 (t, 3H), 1.21 (t, 3H), 1.57 (m, 2H), 1.78 (brm, 4H), 2.59 (q, 2H), 2.99 (q, 2H), 4.01 (m, 4H), 5.70 (s, 2H), 6.90 (s, 2H), 7.01 (d, 2H), 7.35 (d, 2H), 7.57 (d, 2H), 9.43 (s, 1H), 12.50 (brs, 1H) | DMSO-$d_6$ | |
| 96 | N-hydroxy-4-5-[4-(5-ethyl-2-methylamino-1,3-thiazol-4-yl)phenoxy]pentoxy-benzamidine | butrylchloride | thiourea | iodomethane | 1.15 (t, 3H), 1.57 (m, 2H), 1.78 (m, 4H), 2.70 (q, 2H), 2.78 (d, 3H), 3.99 (m, 4H), 5.80 (brs, 2H), 6.92 (m, 4H), 7.25 (q, 1H), 7.42 (d, 2H), 7.58 (d, 2H), 9.48 (s, 1H) | DMSO-$d_6$ | |
| 97 | N-hydroxy-4-5-[4-(5-ethyl-2-ethylamino-1,3-thiazol-4-yl)phenoxy]pentoxy-benzamidine | butrylchloride | thiourea | iodoethane | 1.41 (m, 6H), 1.57 (m, 2H), 1.78 (t, 4H), 2.69 (q, 2H), 3.19 (q, 2H), 3.99 (t, 4H), 5.69 (s, 2H), 6.92 (m, 4H), 7.30 (t, 1H), 7.41 (d, 2H), 7.57 (d, 2H), 9.43 (s, 1H) | DMSO-$d_6$ | |
| 98 | N-hydroxy-4-5-[4-(5-ethyl-2-propylamino-1,3-thiazol-4-yl)phenoxy]pentoxy-benzamidine | butrylchloride | thiourea | propylbromide | 0.89 (t, 3H), 1.15 (t, 3H), 1.55 (brm, 4H), 1.77 (brm, 4H), 2.68 (q, 2H), 3.12 (m, 2H), 3.98 (m, 4H), 5.72 (s, 2H), 6.92 (m, 4H), 7.35 (t, 1H), 7.40 (d, 2H), 7.57 (d, 2H), 9.44 (s, 1H) | DMSO-$d_6$ | |
| 99 | N-hydroxy-4-5-[4-(5-ethyl-2-methoxyacetylamino-1,3-thiazol-4-yl)phenoxy]pentoxy-benzamidine | butrylchloride | thiourea | methoxyacetyl chloride | 1.23 (t, 3H), 1.57 (m, 2H), 1.78 (brm, 4H), 2.84 (q, 2H), 3.33 (s, 3H), 4.00 (m, 4H), 4.11 (s, 2H), 5.70 (s, 2H), 6.90 (d, 2H), 6.98 (d, 2H), 7.47 (d, 2H), 7.82 (d, 2H), 9.43 (s, 1H), 11.96 (s, 1H) | DMSO-$d_6$ | |
| 100 | N-hydroxy-4-5-[4-(5-ethyl-2-(4-pyridylcarbonyl)amino-1,3-thiazol-4-yl)phenoxy]pentoxy-benzamidine | butrylchloride | thiourea | isoniconoylchloride | 1.26 (t, 3H), 1.57 (m, 2H), 1.79 (brm, 4H), 2.88 (q, 2H), 4.00 (m, 4H), 5.74 (s, 2H), 6.91 (d, 2H), 7.01 (d, 2H), 7.52 (d, 2H), 7.55 (d, 2H), 7.98 (d, 2H), 8.79 (d, 2H), 9.45 (s, 1H), 12.92 (s, 1H) | DMSO-$d_6$ | |
| 101 | N-hydroxy-4-5-[4-(5-ethyl-2-(3-pyridylcarbonyl)amino-1,3-thiazol-4-yl)phenoxy]pentoxy-benzamidine | butrylchloride | thiourea | niconoylchloride | 1.26 (t, 3H), 1.57 (brm, 2H), 1.79 (brm, 4H), 2.88 (q, 2H), 4.00 (m, 4H), 5.71 (brs, 2H), 6.91 (d, 2H), 7.01 (d, 2H), 7.56 (m, 5H), 8.40 (m, 1H), 8.77 (dd, 1H), 9.20 (d, 1H), 9.43 (s, 1H), 12.82 (s, 1H) | DMSO-$d_6$ | |
| 102 | N-hydroxy-4-5-[4-(5-ethyl-2-(2-methoxyethyl)amino-1,3-thiazol-4-yl)phenoxy]pentoxy-benzamidine | butrylchloride | thiourea | 2-chloroethylmethylester | 1.14 (t, 3H), 1.60 (m, 2H), 1.78 (m, 4H), 2.69 (m, 2H), 3.26 (s, 3H), 3.40 (m, 2H), 3.38 (m, 2H), 4.02 (m, 4H), 5.67 (s, 2H), 5.75 (s, 1H), 6.90-7.00 (m, 4H), 7.40 (d, 2H), 7.58 (d, 2H), 9.45 (s, 1H) | DMSO-$d_6$ | |
| 103 | N-hydroxy-4-5-[4-(5-isopropyl-2-methylamino-1,3- | isovalerylchloride | thiourea | iodomethane | 1.17 (d, 6H), 1.56 (brm, 2H), 1.77 (brm, 2H), 2.77 (d, 3H), 3.21 (m, 1H), 5.72 (s, 2H), | DMSO-$d_6$ | |

TABLE 3-continued

| example | name | Acid chloride | Thioamide | Alkylhalide | NMR | solvent | mp |
|---|---|---|---|---|---|---|---|
| | thiazol-4-yl)phenoxy]pentoxy-benzamidine | | | | 6.91 (d, 2H), 6.94 (d, 2H), 7.25 (m, 1H), 7.38 (d, 2H), 7.57 (d, 2H), 9.44 (s, 1H) | | |
| 104 | N-hydroxy-4-5-[4-(2-ethylamino-5-isopropyl-1,3-thiazol-4-yl)phenoxy]pentoxy-benzamidine | isovalerylchloride | thiourea | iodoethane | 0.85 (m, 3H), 1.17 (d, 6H), 1.58 (m, 2H), 1.82 (m, 4H), 3.20 (m, 3H), 4.04 (m, 4H), 6.95 (m, 4H), 7.39 (m, 2H), 7.82 (m, 2H) | DMSO-$d_6$ | |
| 105 | N-hydroxy-4-5-[4-(5-butyl-2-methylamino-1,3-thiazol-4-yl)phenoxy]pentoxy-benzamidine | hexanoylchloride | thiourea | iodomethane | 0.83 (t, 3H), 1.30 (m, 2H), 1.48 (m, 2H), 1.56 (m, 2H), 1.77 (m, 4H), 2.67 (t, 2H), 2.78 (d, 3H), 4.01 (m, 4H), 5.72 (brs, 2H), 6.92 (m, 4H), 7.26 (m, 1H), 7.41 (d, 2H), 7.58 (d, 2H), 9.44 (s, 1H) | DMSO-$d_6$ | |
| 106 | N-hydroxy-4-5-[4-(5-butyl-2-ethylamino-1,3-thiazol-4-yl)phenoxy]pentoxy-benzamidine | hexanoylchloride | thiourea | iodoethane | 0.83 (t, 3H), 1.13 (t, 3H), 1.28 (m, 2H), 1.53 (m, 4H), 1.78 (m, 4H), 2.64 (t, 2H), 3.18 (m, 2H), 3.99 (m, 4H), 5.75 (brs, 2H), 6.92 (m, 4H), 7.31 (t, 1H), 7.40 (d, 2H), 7.57 (d, 2H), 9.46 (s, 1H) | DMSO-$d_6$ | |
| 107 | N-hydroxy-4-5-[4-(5-benzyl-2-methylamino-1,3-thiazol-4-yl)phenoxy]pentoxy-benzamidine | hydrocinnamoyl chloride | thiourea | iodomethane | 1.55 (m, 2H), 1.76 (brm, 4H), 2.77 (d, 3H), 3.98 (m, 4H), 4.03 (s, 2H), 5.72 (brs, 2H), 6.91 (m, 4H), 7.20 (m, 3H), 7.29 (m, 3H), 7.46 (d, 2H), 7.57 (d, 2H), 9.44 (s, 1H) | DMSO-$d_6$ | |
| 108 | N-hydroxy-4-5-[4-(5-benzyl-2-ethylamino-1,3-thiazol-4-yl)phenoxy]pentoxy-benzamidine | hydrocinnamoyl chloride | thiourea | iodoethane | 1.14 (m, 3H), 1.55 (m, 2H), 1.77 (brm, 4H), 3.18 (m, 2H), 4.00 (m, 4H), 4.03 (s, 2H), 6.94 (m, 4H), 7.17 (m, 3H), 7.29 (m, 2H), 7.39 (t, 1H), 7.45 (d, 2H), 7.58 (d, 2H), 9.64 (s, 1H) | DMSO-$d_6$ | |
| 109 | N-hydroxy-4-5-[4-(5-cyclopentylmethyl-2-methylamino-1,3-thiazol-4-yl)phenoxy]pentoxy-benzamidine | cyclopentyl-propionylchloride | thiourea | iodomethane | 1.10 (brm, 2H), 1.49 (brm, 4H), 1.56 (m, 2H), 1.69 (m, 2H), 1.78 (m, 4H), 1.97 (m, 1H), 2.66 (d, 2H), 2.78 (d, 3H), 3.99 (m, 4H), 5.71 (s, 2H), 6.92 (m, 4H), 7.25 (m, 1H), 7.40 (d, 2H), 7.57 (d, 2H), 9.44 (s, 1H) | DMSO-$d_6$ | |
| 110 | N-hydroxy-4-5-[4-(5-cyclopentylmethyl-2-ethylamino-1,3-thiazol-4-yl)phenoxy]pentoxy-benzamidine | cyclopentyl-propionylchloride | thiourea | iodomethane | 1.13 (m, 5H), 1.49 (m, 6H), 1.69 (m, 2H), 1.77 (m, 4H), 1.97 (m, 1H), 2.66 (d, 2H), 3.19 (m, 2H), 3.99 (m, 4H), 5.70 (s, 2H), 6.91 (m, 4H), 7.29 (t, 1H), 7.40 (d, 2H), 7.57 (d, 2H), 9.44 (s, 1H) | DMSO-$d_6$ | |
| 111 | N-hydroxy-4-5-[4-(5-cyclopentylmethyl-2-propylamino-1,3-thiazol-4-yl)phenoxy]pentoxy-benzamidine | cyclopentyl-propionylchloride | thiourea | propylbromide | 0.88 (t, 3H), 1.10 (brm, 2H), 1.55 (brm, 8H), 1.77 (brm, 6H), 1.97 (m, 1H), 2.65 (d, 2H), 3.11 (m, 2H), 3.99 (m, 4H), 5.70 (s, 2H), 6.90 (d, 2H), 6.92 (d, 2H), 7.33 (t, 1H), 7.39 (d, 2H), 7.57 (d, 2H), 9.44 (s, 1H) | DMSO-$d_6$ | |
| 112 | N-hydroxy-4-5-[4-(5-cyclopentylmethyl-2-(4-pyridylcarbonyl)amino-1,3-thiazol-4-yl)phenoxy]pentoxy-benzamidine | cyclopentyl-propionylchloride | thiourea | isoniconoylchloride | 1.55 (m, 2H), 1.49 (brm, 6H), 1.77 (brm, 6H), 2.10 (m, 1H), 2.86 (d, 2H), 4.00 (m, 4H), 5.74 (s, 2H), 6.91 (d, 2H), 7.01 (d, 2H), 7.51 (d, 2H), 7.58 (d, 2H), 7.97 (d, 2H), 8.79 (d, 2H), 9.46 (s, 1H), 12.91 (s, 1H) | DMSO-$d_6$ | |
| 113 | N-hydroxy-4-5-[4-(5-cyclopentyl-2-propylamino-1,3-thiazol-4-yl)phenoxy]pentoxy-benzamidine | cyclopentylacetyl chloride | thiourea | propylbromide | 0.89 (t, 3H), 1.55-1.62 (m, 8H), 1.77-1.80 (m, 8H), 3.31-3.37 (m, 3H), 4.00-4.02 (m, 4H), 6.90-7.05 (m, 4H), 7.39-7.80 (m, 4H) | DMSO-$d_6$ | |
| 114 | N-hydroxy-4-5-[4-(5-isopropyl-2-[(pyridin-3- | isovalerylchloride | thiourea | 3-bromomethylpyridin | 0.82 (d, 6H), 1.17-1.25 (m, 2H), 1.78-1.80 (m, 4H), 3.25 (m, 1H), 3.37 (s, 2H), 4.01 (m, 4H), 6.94-7.83 (m, 12H) | DMSO-$d_6$ | |

TABLE 3-continued

| example | name | Acid chloride | Thioamide | Alkylhalide | NMR | solvent | mp |
|---|---|---|---|---|---|---|---|
| | ylmethyl)amino]-1,3-thiazol-4-yl)phenoxy]pentoxy-benzamidine | | | | | | |
| 115 | N-hydroxy-4-5-[4-(5-(2-chloroethyl)-2-methylamino-1,3-thiazol-4-yl)phenoxy]pentoxy-benzamidine | 4-chlorobutryl-chloride | thiourea | iodomethane | 1.58 (m, 2H), 1.80 (m, 4H), 2.81 (s, 3H), 3.13 (m, 2H), 3.78 (m, 2H), 4.01 (m, 4H), 5.73 (m, 2H), 6.93 (m, 4H), 7.44 (m, 2H), 7.59 (m, 2H), 9.46 (s, 1H) | DMSO-$d_6$ | |
| 116 | N-hydroxy-4-5-[4-(2-methylamino-1,3-thiazol-4-yl)phenoxy]pentoxy-benzamidine | propyl chloride | thiourea | iodomethane | 1.57 (m, 2H), 1.77-1.81 (m, 4H), 2.86 (d, 3H), 3.99-4.01 (m, 4H), 5.72 (s, 2H), 6.88-6.93 (m, 5H), 7.59 (d, 2H), 7.74 (d, 2H), 9.46 (s, 1H) | DMSO-$d_6$ | |
| 117 | N-hydroxy-4-5-[4-(5-ethyl-2-[(pyridin-3-ylmethyl)amino-1,3-thiazol-4-yl)phenoxy]pentoxy-benzamidine | butyryl chloride | thiourea | 3-bromomethylpyridin | 1.24 (t, 3H), 1.57 (m, 2H), 1.79 (m, 4H), 2.87 (q, 2H), 3.79 (s, 2H), 3.91 (s, 2H), 4.02 (m, 4H), 5.74 (s, 1H), 6.94 (d-d, 4H), 7.35 (m, 1H), 7.48 (d, 2H), 7.77 (d, 1H), 7.82 (d, 2H), 8.45 (d, 1H), 8.54 (s, 1H) | DMSO-$d_6$ | |

Examples 118 to 163

Compound (18) prepared according to the same method as that in the Preparative Example 3 was reacted in the same manner as Example 1, obtaining the title compounds shown I Table 4.

Table 4 shows the title compounds, reactants and $^1$H-NMR data.

TABLE 4

| example | name | Acid chloride | Thioamide | Alkylhalide | NMR | solvent | mp |
|---|---|---|---|---|---|---|---|
| 118 | N-hydroxy-4-5-[4-(2-(ethansulfonyl-methyl-amino)-1,3-thiazol-4-yl)phenoxy]pentoxy-benzamidine | acetylchloride | thiourea | ethansulfonyl-chloride | 1.20 (t, 3H), 1.57 (m, 2H), 1.79 (m, 4H), 3.50 (m, 5H), 4.01 (m, 4H), 5.71 (s, 2H), 6.96 (m, 4H), 7.55 (m, 2H), 7.81 (m, 3H), 9.44 (s, 1H) | DMSO-$d_6$ | |
| 119 | N-hydroxy-4-5-[4-(2-methyl-(2-morpholinoethyl)amino-1,3-thiazol-4-yl)phenoxy]pentoxy-benzamidine | acetylchloride | thiourea | chloroethyl-morpholine | 1.56 (brm, 2H), 1.78 (brm, 4H), 2.43 (m, 4H), 2.55 (m, 2H), 3.05 (s, 3H), 3.52 (m, 4H), 3.60 (m, 2H), 3.99 (brm, 4H), 5.70 (s, 2H), 6.91 (m, 4H), 6.95 (s, 1H), 7.57 (d, 2H), 7.73 (d, 2H), 9.44 (s, 1H) | DMSO-$d_6$ | |
| 120 | N-hydroxy-4-5-[4-(2-(2-hydroxyethyl)-methyl-amino]-5-methyl-1,3-thiazol-4-yl)phenoxy]pentoxy-benzamidine | propionylchloride | thiourea | bromoethanol | 1.56 (m, 2H), 1.78 (brm, 4H), 2.31 (s, 3H), 3.02 (s, 3H), 3.44 (t, 2H), 3.59 (q, 2H), 4.00 (t, 4H), 4.79 (t, 1H), 5.71 (s, 2H), 6.90 (d, 2H), 6.94 (d, 2H), 7.48 (d, 2H), 7.57 (d, 2H), 9.43 (s, 1H) | DMSO-$d_6$ | |
| 121 | N-hydroxy-4-5-[4-(2-(ethyl-(2-hydroxyethyl)-amino)-5-methyl-1,3-thiazol-4-yl)phenoxy]pentoxy-benzamidine | propionylchloride | thiourea | bromoethanol | 1.14 (t, 3H), 1.56 (m, 2H), 1.78 (brm, 4H), 2.31 (s, 3H), 3.41 (m, 4H), 3.58 (m, 2H), 4.00 (m, 4H), 4.82 (t, 1H), 5.73 (s, 2H), 6.91 (d, 2H), 6.94 (d, 2H), 7.48 (d, 2H), 7.57 (d, 2H), 9.45 (s, 1H) | DMSO-$d_6$ | |
| 122 | N-hydroxy-4-5-[4-(2-(bis-(2-methoxyethyl)-amino)-5-methyl-1,3-thiazol-4-yl)phenoxy]pentoxy-benzamidine | propionylchloride | thiourea | 2-chloroethyl-methylester | 1.59 (m, 2H), 1.79 (m, 4H), 2.32 (s, 3H), 3.26 (s, 6H), 3.55 (s, 8H), 4.03 (m, 4H), 5.70 (s, 2H), 6.91 (d, 2H), 6.95 (d, 2H), 7.49 (d, 2H), 7.82 (d, 2H), 9.44 (s, 1H) | DMSO-$d_6$ | |
| 123 | N-hydroxy-4-5-[4-(5-methyl-2-(methyl-(2-morpholinoethyl)- | propionylchloride | thiourea | chloroethyl-morpholine | 1.56 (m, 2H), 1.77 (brm, 4H), 2.32 (s, 3H), 2.41 (brm, 4H), 2.51 (m, 2H), 2.99 (s, 3H), 3.51 (brm, 4H), 3.99 (t, 4H), | DMSO-$d_6$ | |

TABLE 4-continued

| example | name | Acid chloride | Thioamide | Alkylhalide | NMR | solvent | mp |
|---|---|---|---|---|---|---|---|
| | amino)-1,3-thiazol-4-yl)phenoxy]pentoxy-benzamidine | | | | 5.70 (s, 2H), 6.90 (d, 2H), 6.94 (d, 2H), 7.48 (d, 2H), 7.57 (d, 2H), 9.44 (s, 1H) | | |
| 124 | N-hydroxy-4-5-[4-(2-(ethyl-1-(2-morpholinoethyl)-amino)-5-methyl-1,3-thiazol-4-yl)phenoxy]pentoxy-benzamidine | propionylchloride | thiourea | chloroethyl-morpholine | 1.15 (t, 3H), 1.56 (m, 2H), 1.77 (brm, 4H), 2.31 (s, 3H), 2.42 (brm, 4H), 2.52 (m, 2H), 3.40 (m, 2H), 3.49 (m, 2H), 3.54 (brm, 4H), 3.99 (m, 4H), 5.71 (brs, 2H), 6.90 (d, 2H), 6.94 (d, 2H), 7.48 (d, 2H), 7.57 (d, 2H), 9.44 (s, 1H) | DMSO-$d_6$ | |
| 125 | N-hydroxy-4-5-[4-(2-(benzyl-methyl-amino)-5-methyl-1,3-thiazol-4-yl)phenoxy]pentoxy-benzamidine | propionylchloride | thiourea | benzyl bromide | 1.57 (m, 2H), 1.77 (brm, 4H), 2.29 (s, 3H), 2.98 (s, 3H), 3.99 (m, 4H), 4.64 (s, 2H), 5.70 (s, 2H), 6.90 (d, 2H), 6.94 (d, 2H), 7.30 (m, 5H), 7.51 (d, 2H), 7.57 (d, 2H), 9.44 (s, 1H) | DMSO-$d_6$ | |
| 126 | N-hydroxy-4-5-[4-(5-methyl-2-(methyl-pyridin-3-yl-methyl-amino)-1,3-thiazol-4-yl)phenoxy]pentoxy-benzamidine | propionylchloride | thiourea | 3-bromomethyl-pyridin | 1.56 (brm, 2H), 1.77 (brm, 4H), 2.33 (s, 3H), 3.00 (s, 3H) 4.00 (m, 4H), 4.68 (s, 2H), 5.71 (s, 2H), 6.90 (d, 2H), 6.95 (d, 2H), 7.36 (m, 1H), 7.51 (d, 2H), 7.57 (d, 2H), 7.72 (d, 1H), 8.48 (d, 1H), 8.55 (s, 1H), 9.44 (s, 1H) | DMSO-$d_6$ | |
| 127 | N-hydroxy-4-5-[4-(2-(benzyl-ethyl-amino)-5-methyl-1,3-thiazol-4-yl)phenoxy]pentoxy-benzamidine | propionylchloride | thiourea | benzyl bromide | 1.12 (t, 3H), 1.56 (brm, 2H), 1.77 (brm, 4H), 2.31 (s, 3H), 3.40 (q, 2H), 3.99 (m, 4H), 4.62 (s, 2H), 5.71 (s, 2H), 6.90 (d, 2H), 6.94 (d, 2H), 7.26 (m, 1H), 7.31 (m, 4H), 7.50 (d, 2H), 7.57 (d, 2H), 9.44 (s, 1H) | DMSO-$d_6$ | |
| 128 | N-hydroxy-4-5-[4-(2-(bis-(2-hydroxyethyl)-amino)-5-methyl-1,3-thiazol-4-yl)phenoxy]pentoxy-benzamidine | propionylchloride | thiourea | bromoethanol | 1.57 (m, 2H), 1.80 (m, 4H), 2.24 (s, 3H), 3.0-4.5 (brs, 2H), 3.67 (s, 8H), 4.05 (m, 4H), 5.72 (s, 2H), 7.03 (d, 2H), 7.12 (d, 2H), 7.44 (d, 2H), 7.82 (d, 2H) 9.45 (s, 1H) | DMSO-$d_6$ | |
| 129 | N-hydroxy-4-5-[4-(5-ethyl-2-((2-hydroxyethyl)-methyl-amino)-1,3-thiazol-4-yl)phenoxy]pentoxy-benzamidine | butrylchloride | thiourea | bromoethanol | 1.17 (t, 3H), 1.57 (m, 2H), 1.78 (brm, 4H), 2.72 (q, 2H), 3.03 (s, 3H), 3.45 (t, 2H), 3.59 (m, 2H), 4.01 (m, 4H) 4.79 (t, 1H), 5.70 (s, 2H) 6.90 (d, 2H), 6.96 (d, 2H), 7.42 (d, 2H) 7.57 (d, 2H), 9.43 (s, 1H) | DMSO-$d_6$ | |
| 130 | N-hydroxy-4-5-[4-(5-ethyl-2-(ethyl-(2-hydroxyethyl)-amino)-1,3-thiazol-4-yl)phenoxy]pentoxy-benzamidine | butrylchloride | thiourea | bromoethanol | 1.15 (m, 6H), 1.56 (brm, 2H), 1.76 (brm, 4H), 2.71 (q, 2H), 3.43 (m, 4H), 4.00 (t, 4H), 4.81 (t, 1H), 5.70 (s, 2H) 6.90 (d, 2H), 6.94 (d, 2H) 7.42 (d, 2H), 7.81 (d, 2H), 9.43 (s, 1H) | DMSO-$d_6$ | |
| 131 | N-hydroxy-4-5-[4-(5-ethyl-2-(methyl-(2-morpholinoethyl)-amino)-1,3-thiazol-4-yl)phenoxy]pentoxy-benzamidine | butrylchloride | thiourea | chloroethyl-morpholine | 1.17 (t, 3H) 1.56 (m, 2H), 1.77 (m, 4H), 2.41 (brm, 4H) 2.51 (m, 2H), 2.72 (q, 2H), 3.00 (s, 3H), 3.53 (brm, 6H), 3.99 (t, 4H), 5.70 (s, 2H) 6.90 (d, 2H), 6.94 (d, 2H), 7.42 (d, 2H) 7.57 (d, 2H), 9.43 (s, 1H) | DMSO-$d_6$ | |
| 132 | N-hydroxy-4-5-[4-(5-ethyl-2-(ethyl-(2-morpholinoethyl)-amino)-1,3-thiazol-4-yl)phenoxy]pentoxy-benzamidine | butrylchloride | thiourea | chloroethyl-morpholine | 1.15 (m, 6H), 1.56 (m, 2H), 1.78 (brm, 4H), 2.42 (brm, 4H), 2.51 (m, 2H), 2.70 (q, 2H), 3.40 (m, 2H), 3.48 (m, 2H) 3.53 (brm, 4H), 4.00 (m, 4H) 5.70 (s, 2H), 6.90 (d, 2H), 6.94 (d, 2H) 7.42 (d, 2H), 7.57 (d, 2H) 9.43 (s, 1H) | DMSO-$d_6$ | |
| 133 | N-hydroxy-4-5-[4-(2-(benzyl-methyl-amino)-5-ethyl-1,3-thiazol-4-yl)phenoxypentoxy]-benzamidine | butrylchloride | thiourea | benzyl bromide | 1.17 (t, 3H), 1.57 (brm, 2H), 1.77 (brm, 4H), 2.74 (q, 2H), 2.98 (s, 3H), 3.99 (m, 4H), 4.64 (s, 2H), 5.71 (s, 2H), 6.90 (d, 2H), 6.94 (d, 2H), 7.30 (m, 5H), 7.45 (d, 2H), 7.57 (d, 2H), 9.44 (s, 1H) | DMSO-$d_6$ | |
| 134 | N-hydroxy-4-5-[4-(5-ethyl-2-(methyl- | butrylchloride | thiourea | 3-bromomethyl-pyridin | 1.18 (t, 3H), 1.56 (m, 2H), 1.77 (brm, 4H), 2.74 (q, 2H), | DMSO-$d_6$ | |

TABLE 4-continued

| example | name | Acid chloride | Thioamide | Alkylhalide | NMR | solvent | mp |
|---|---|---|---|---|---|---|---|
| | (pyridin-3-yl-methyl)amino)-1,3-thiazol-4-yl)phenoxy]pentoxy-benzamidine | | | | 3.01 (s, 3H), 3.99 (t, 4H), 4.69 (s, 2H), 5.70 (s, 2H), 5.90 (d, 2H), 6.95 (d, 2H), 7.37 (m, 1H), 7.45 (d, 2H), 7.57 (d, 2H), 7.72 (d, 1H), 8.47 (d, 1H), 8.55 (s, 1H), 9.43 (s, 1H) | | |
| 135 | N-hydroxy-4-5-[4-(2-(benzyl-ethyl-amino)-5-ethyl-1,3-thiazol-4-yl)phenoxy]pentoxy-benzamidine | butrylchloride | thiourea | benzyl bromide | 1.15 (m, 6H), 1.56 (m, 2H), 1.76 (brm, 4H), 2.73 (q, 2H), 3.41 (q, 2H), 3.99 (t, 4H), 4.63 (s, 2H), 5.70 (s, 2H), 6.90 (d, 2H), 6.94 (d, 2H), 7.25 (m, 1H), 7.32 (m, 4H), 7.44 (d, 2H), 7.57 (d, 2H), 9.43 (s, 1H) | DMSO-$d_6$ | |
| 136 | N-hydroxy-4-5-[4-(5-ethyl-2-(ethyl-(pyridin-3-yl-methyl)amino)-1,3-thiazol-4-yl)phenoxy]pentoxy-benzamidine | butrylchloride | thiourea | 3-bromomethyl-pyridin | 1.15 (m, 6H), 1.56 (m, 2H), 1.76 (m, 4H), 2.73 (q, 2H), 3.44 (q, 2H), 3.99 (t, 4H), 4.66 (s, 2H), 5.70 (s, 2H), 5.74 (s, 1H), 6.90 (d, 2H), 6.94 (d, 2H), 7.36 (m, 1H), 7.43 (d, 2H), 7.57 (d, 2H), 7.73 (d, 2H), 8.46 (d, 1H), 8.56 (d, 1H), 9.44 (s, 1H) | DMSO-$d_6$ | |
| 137 | N-hydroxy-4-5-[4-(2-(bis-(pyridin-3-yl-methyl)amino)-5-ethyl-1,3-thiazol-4-yl)phenoxy]pentoxy-benzamidine | butrylchloride | thiourea | 3-bromomethyl-pyridin | 1.15 (t, 3H), 1.56 (brm, 2H), 1.79 (brm, 4H), 2.73 (q, 2H), 3.99 (t, 2H), 4.09 (t, 2H), 4.91 (s, 4H), 6.95 (d, 2H), 7.14 (d, 2H), 7.41 (d, 2H), 7.67 (d, 2H), 7.82 (m, 2H), 8.26 (m, 2H), 8.73 (m, 2H), 8.79 (s, 2H). | DMSO-$d_6$ | |
| 138 | N-hydroxy-4-5-[4-(2-dipropylamino-5-ethyl-1,3-thiazol-4-yl)phenoxy]pentoxy-benzamidine | butrylchloride | thiourea | propylbromide | 0.86 (t, 6H), 1.17 (t, 3H), 1.59 (brm, 6H), 1.77 (brm, 4H), 2.71 (q, 2H), 3.30 (m, 4H), 3.99 (m, 4H), 5.71 (brs, 2H), 6.91 (d, 2H), 6.94 (d, 2H), 7.42 (d, 2H), 7.57 (d, 2H), 9.44 (s, 1H) | DMSO-$d_6$ | |
| 139 | N-hydroxy-4-5-[4-(2-(bis-(2-hydroxyethyl)amino)-5-ethyl-1,3-thiazol-4-yl)phenoxy]pentoxy-benzamidine | butrylchloride | thiourea | bromoethanol | 1.17 (t, 3H), 1.57 (brm, 2H), 1.77 (brm, 4H), 2.71 (q, 2H), 3.48 (m, 4H), 3.63 (m, 4H), 3.99 (m, 4H), 4.87 (t, 2H), 5.69 (s, 2H), 6.90 (d, 2H), 6.94 (d, 2H), 7.41 (d, 2H), 7.57 (d, 2H), 9.43 (s, 1H) | DMSO-$d_6$ | |
| 140 | N-hydroxy-4-5-[4-(2-((2-hydroxyethyl)-methyl-amino)-5-isopropyl-1,3-thiazol-4-yl)phenoxy]pentoxy-benzamidine | isovalerylchloride | thiourea | bromoethanol | 1.26 (d, 6H), 1.57 (m, 2H), 1.79 (m, 4H), 3.33 (m, 5H), 3.47 (m, 1H), 3.61 (m, 2H), 4.00 (m, 4H), 5.72 (s, 2H), 6.90-7.00 (b, 4H), 7.45 (d, 2H), 7.57 (d, 2H), 9.45 (s, 1H) | DMSO-$d_6$ | |
| 141 | N-hydroxy-4-5-[4-(5-isopropyl-2-(methyl-(pyridin-3-ylmethyl)amino)-1,3-thiazol-4-yl)phenoxy]pentoxy-benzamidine | isovalerylchloride | thiourea | 3-bromomethyl-pyridin | 1.20 (d, 6H), 1.56 (m, 2H), 1.79 (m, 4H), 3.01 (s, 3H), 3.24 (m, 1H), 3.32 (s, 2H), 4.00 (m, 4H), 5.70 (s, 2H), 6.90 (b, 4H), 7.40 (b, 3H), 7.57 (d, 2H), 7.92 (m, 1H), 8.47-8.56 (b, 2H), 9.43 (s, 1H) | DMSO-$d_6$ | |
| 142 | N-hydroxy-4-5-[4-(2-(ethansulfonyl-methyl-amino)-5-isopropyl-1,3-thiazol-4-yl)phenoxy]pentoxy-benzamidine | isovalerylchloride | thiourea | ethansulfonyl-chloride | 1.24 (m, 9H), 1.56 (brm, 2H), 1.79 (brm, 4H), 3.41 (s, 3H), 3.46 (q, 2H), 4.00 (m, 4H), 5.74 (s, 2H), 6.91 (d, 2H), 6.95 (d, 2H), 7.45 (d, 2H), 7.57 (d, 2H), 9.45 (s, 1H) | DMSO-$d_6$ | |
| 143 | N-hydroxy-4-5-[4-(5-butyl-2-((2-hydroxyethyl)-methyl-amino)-1,3-thiazol-4-yl)phenoxy]pentoxy-benzamidine | hexanoylchloride | thiourea | bromoethanol | 0.84 (t, 3H), 1.32 (m, 2H), 1.54 (m, 4H), 1.78 (m, 4H), 2.70 (t, 2H), 3.303 (s, 3H), 3.46 (t, 2H), 3.54 (m, 2H), 4.01 (m, 4H), 5.71 (s, 2H), 6.91 (d, 2H), 6.94 (d, 2H), 7.42 (d, 2H), 7.58 (d, 2H), 9.46 (s, 1H) | DMSO-$d_6$ | |
| 144 | N-hydroxy-4-5-[4-(5-butyl-2-(methyl-(2-morpholinoethyl)amino)-1,3-thiazol-4-yl)phenoxy]pentoxy-benzamidine | hexanoylchloride | thiourea | chloroethyl-morpholine | 0.83 (t, 3H), 1.30 (m, 2H), 1.53 (m, 4H), 1.77 (brm, 4H), 2.42 (brm, 4H), 2.52 (m, 2H), 2.69 (m, 2H), 2.99 (s, 3H, 3.52 (brm, 6H), 4.00 (m, 4H), 5.72 (s, 2H), 6.92 (m, 4H), 7.41 (d, 2H), 7.57 (d, 2H), 9.44 (s, 1H) | DMSO-$d_6$ | |

TABLE 4-continued

| example | name | Acid chloride | Thioamide | Alkylhalide | NMR | solvent | mp |
|---|---|---|---|---|---|---|---|
| 145 | N-hydroxy-4-5-[4-(5-butyl-2-(methyl-(pyridin-3-yl-methyl)amino)-1,3-thiazol-4-yl)phenoxy]pentoxy-benzamidine | hexanoylchloride | thiourea | 3-bromomethyl-pyridin | 0.82 (t, 3H), 1.29 (m, 2H), 1.52 (brm, 4H), 1.76 (brm, 4H), 2.70 (m, 2H), 3.00 (s, 3H), 3.98 (m, 4H), 4.68 (s, 2H), 5.76 (s, 2H), 6.90 (d, 2H), 6.94 (d, 2H), 7.37 (m, 1H), 7.44 (d, 2H), 7.58 (d, 2H), 7.72 (d, 1H), 8.47 (d, 1H), 8.55 (s, 1H), 9.48 (s, 1H) | DMSO-d$_6$ | |
| 146 | N-hydroxy-4-5-[4-(5-butyl-2-dipropylamino-1,3-thiazol-4-yl)phenoxyl]pentoxy-benzamidine | hexanoylchloride | thiourea | propylbromide | 0.84 (m, 9H), 1.30 (m, 2H), 1.57 (m, 8H), 1.77 (brm, 4H), 2.68 (m, 2H), 3.33 (m, 4H), 4.00 (m, 4H), 5.70 (s, 2H), 6.90 (d, 2H), 6.94 (d, 2H), 7.41 (d, 2H), 7.57 (d, 2H), 9.43 (s, 1H) | DMSO-d$_6$ | |
| 147 | N-hydroxy-4-5-[4-(5-cyclopentylmethyl-2-(methyl-(pyridin-3-yl-methyl)amino)-1,3-thiazol-4-yl)phenoxy]pentoxy-benzamidine | cyclopentyl-propionylchloride | thiourea | 3-bromomethyl-pyridin | 1.10 (m, 2H), 1.51 (m, 6H), 1.76 (brm, 6H), 1.99 (m, 1H), 2.71 (d, 2H), 3.00 (s, 3H), 3.99 (t, 4H), 4.68 (s, 2H), 5.72 (s, 2H), 6.90 (d, 2H), 6.95 (d, 2H), 7.36 (m, 1H), 7.43 (d, 2H), 7.57 (d, 2H), 7.72 (d, 1H), 8.48 (d, 1H), 8.55 (s, 1H), 9.45 (s, 1H) | DMSO-d$_6$ | |
| 148 | N-hydroxy-4-5-[4-(5-cyclopentylmethyl-2-(methyl-(2-morpholinoethyl)amino)-1,3-thiazol-4-yl)phenoxy]pentoxy-benzamidine | cyclopentyl-propionylchloride | thiourea | chloroethyl-morpholine | 1.11 (brm, 2H), 1.52-1.56 (brm, 6H), 1.77 (brm, 6H), 2.0 (m, 1H), 2.69 (m, 2H), 3.00 (s, 3H), 3.33 (m, 4H), 3.55 (m, 6H), 4.00 (m, 4H), 5.81 (s, 2H), 6.93 (m, 4H), 7.40 (d, 2H), 7.57 (d, 2H), 9.50 (s, 1H) | DMSO-d$_6$ | |
| 149 | N-hydroxy-4-5-[4-(5-cyclopentylmethyl-2-dipropylamino-1,3-thiazol-4-yl)phenoxy]pentoxy-benzamidine | cyclopentyl-propionylchloride | thiourea | propylbromide | 0.85 (m, 6H), 1.08 (m, 2H), 1.46-1.77 (brm, 16H), 1.99 (m, 1H), 2.67 (d, 2H), 3.30 (m, 4H), 3.99 (m, 4H), 6.04 (s, 2H), 6.90 (d, 2H), 6.93 (d, 2H), 7.41 (d, 2H), 7.59 (d, 2H), 9.60 (s, 1H) | DMSO-d$_6$ | |
| 150 | N-hydroxy-4-5-[4-(5-butyl-2-diethylamino-1,3-thiazol-4-yl)phenoxy]pentoxy-benzamidine | hexanoylchloride | thiourea | iodoethane | 0.84 (m, 3H), 1.14 (t, 6H), 1.30 (m, 2H), 1.55 (m, 4H), 1.77 (m, 4H), 2.69 (m, 2H), 3.40 (m, 4H), 3.98 (m, 4H), 5.73 (s, 2H), 6.92 (d-d, 4H), 7.43 (d, 2H), 7.60 (d, 2H), 9.49 (s, 1H) | DMSO-d$_6$ | |
| 151 | N-hydroxy-4-5-[4-(5-butyl-2-ethylmethylamino-1,3-thiazol-4-yl)phenoxy]pentoxy-benzamidine | hexanoylchloride | thiourea | iodoethane | 0.85 (t, 3H), 1.12 (t, 3H), 1.30 (m, 2H), 1.53 (m, 4H), 1.78 (m, 4H), 2.70 (m, 2H), 2.96 (s, 3H), 3.42 (m, 2H), 5.74 (s, 2H), 6.93 (m, 4H), 7.43d, 2H), 7.59 (d, 2H), 9.47 (s, 1H) | DMSO-d$_6$ | |
| 152 | N-hydroxy-4-5-[4-(5-butyl-2-dimethylamino-1,3-thiazol-4-yl)phenoxy]pentoxy-benzamidine | hexanoylchloride | thiourea | iodomethane | 0.81 (t, 3H), 1.25 (m, 2H), 1.52 (m, 4H), 1.76 (m, 4H), 2.67 (m, 2H), 2.97 (s, 6H), 3.97 (m, 4H), 5.70 (s, 2H), 6.91 (d-d, 4H), 7.41 (d, 2H), 7.57 (d, 2H), 9.50 (s, 1H) | DMSO-d$_6$ | |
| 153 | N-hydroxy-4-[5-(4-5-cyclopentyl-2-[methyl-(2-morpholinoethyl)amino]-1,3-thiazol-4-ylphenoxy)pentoxy]-benzamidine | cyclopentyl-ethylchloride | thiourea | chloroethyl-morpholine | 1.56-1.59 (m, 6H), 1.73-1.81 (m, 6H), 2.00-2.10 (m, 2H), 2.38-2.49 (m, 4H), 2.50-2.51 (m, 2H), 3.01 (s, 3H), 3.25 (m, 1H), 3.52--3.55 (m, 6H), 4.00-4.03 (m, 4H), 5.74 (s, 2H), 6.91-6.97 (m, 4H), 7.41 (d, 2H), 7.59 (d, 2H), 9.47 (s, 1H) | DMSO-d$_6$ | |
| 154 | N-hydroxy-4-[5-(4-5-isobutyl-2-[methyl-(2-morpholinoethyl)amino]-1,3-thiazol-4-ylphenoxy)pentoxy]-benzamidine | isocaproylchloride | thiourea | chloroethyl-morpholine | 0.88 (d, 6H), 1.78 (m, 2H), 1.80-1.82 (m, 5H), 2.43 (s, 3H), 2.50 (m, 2H), 2.53 (m, 2H), 3.01 (m, 2H), 3.18 (m, 2H), 3.54 (m, 6H), 4.02 (m, 4H), 5.76 (s, 2H), 6.94-6.97 (m, 4H), 7.41 (d, 2H), 7.60 (d, 2H), 9.46 (s, 1H) | DMSO-d$_6$ | |
| 155 | N-hydroxy-4-5-[4-(5-(2-chloroethyl)-2- | 4-chlorobutrylchloride | thiourea | iodomethane | 1.58-1.66 (m, 2H), 1.78-1.81 (m, 4H) 3.14 (s, 6H), 3.15 (t, 2H), 3.81 (t, 2H), 4.02 (m, 4H), 5.72 (s, 2H), | DMSO-d$_6$ | |

TABLE 4-continued

| example | name | Acid chloride | Thioamide | Alkylhalide | NMR | solvent | mp |
|---|---|---|---|---|---|---|---|
| | dimethylamino-1,3-thiazol-4-yl)phenoxy]pentoxy-benzamidine | | | | 6.91-6.98 (m, 4H), 7.46 (d, 2H), 7.59 (d, 2H), 9.45 (s, 1H) | | |
| 156 | N-hydroxy-4-5-[4-(5-cyclopentyl-2-diethylamino-1,3-thiazol-4-yl)phenoxy]pentoxy-benzamidine | cyclopentyl-ethylchloride | thiourea | propylbromide | 0.86-0.88 (m, 6H), 1.58-1.61 (m, 10H), 1.78 (m, 8H), 3.32-3.39 (m, 5H), 4.02-4.05 (m, 4H), 6.95-7.18 (m, 4H), 7.40 (d, 2H), 7.83 (d, 2H) | DMSO-d$_6$ | |
| 157 | N-hydroxy-4-5-[4-[5-isopropyl-2-dipropylamino-1,3-thiazol-4-yl)phenoxy]pentoxy-benzamidine | isovalerylchloride | thiourea | propylbromide | 0.84-0.88 (m, 6H), 1.24 (d, 6H), 1.57-1.63 (m, 6H), 1.77-1.79 (m, 4H), 3.28-3.38 (m, 5H), 3.97-4.01 (m, 4H), 5.71 (s, 2H), 6.89-6.95 (m, 4H), 7.41-4.59 (m, 4H), 9.45 (s, 1H) | DMSO-d$_6$ | |
| 158 | N-hydroxy-4-5-[4-(5-ethyl-2-diethylamino-1,3-thiazol-4-yl)phenoxy]pentoxy-benzamidine | butrylchloride | thiourea | ethylbromide | 1.15 (t, 3H), 1.23 (t, 6H), 1.58 (m, 2H), 1.79-1.83 (m, 4H), 2.51 (m, 2H), 3.60-3.64 (m, 4H), 4.08-4.12 (m, 4H), 7.13-7.16 (m, 4H), 7.43 (d, 2H), 7.69 (d, 2H) | DMSO-d$_6$ | |
| 158 | N-hydroxy-4-[5-(4-5-isopropyl-2-[methyl-(2-morpholinoethyl)amino]-1,3-thiazol-4-ylphenoxy)pentoxy]-benzamidine | isovalerylchloride | thiourea | chloroethyl-morpholine | 1.22 (d, 6H), 1.56 (m 2H), 1.78 (m, 4H), 2.43 (m, 4H), 2.55 (t, 2H), 3.05 (s, 3H), 3.34 (m, 1H), 3.51 (m, 4H), 3.61 (t, 2H), 3.99 (m, 4H), 5.70 (brs, 2H), 6.90 (m, 4H), 7.57 (m, 2H), 7.73 (m, 2H), 9.44 (brs, 1H) | DMSO-d$_6$ | |
| 160 | N-hydroxy-4-5-[4-(5-cyclopentylmethyl-2-diethylamino-1,3-thiazol-4-yl)phenoxy]pentoxy-benzamidine | cyclopentyl-propionylchloride | thiourea | iodoethane | 1.12-1.16 (m, 8H), 1.56 (m, 6H), 1.78 (m, 6H), 1.98-2.00 (m, 1H), 2.68 (d, 2H), 3.38-3.40 (m, 4H), 4.00 (m, 4H), 5.89 (s, 2H), 6.91-6.95 (d-d, 4H), 7.42 (d, 2H), 7.59 (d, 2H), 9.53 (s, 1H) | DMSO-d$_6$ | |
| 161 | N-hydroxy-4-5-[4-(5-isopropyl-2-dimethylamino-1,3-thiazol-4-yl)phenoxy]pentoxy-benzamidine | isovalerylchloride | thiourea | iodomethane | 1.20 (d, 6H), 1.56 (m, 2H), 1.78 (m, 4H), 2.98 (s, 6H), 3.34 (m, 1H), 3.98-4.01 (m, 4H), 5.77 (s, 2H), 6.90-6.96 (m, 4H), 7.39 (d, 2H), 7.58 (d, 2H), 9.47 (s, 1H) | DMSO-d$_6$ | |
| 162 | N-hydroxy-4-5-[4-(5-isopropyl-2-diethylamino-1,3-thiazol-4-yl)phenoxy]pentoxy-benzamidine | isovalerylchloride | thiourea | iodoethane | 1.14 (m, 6H), 1.20 (d, 6H), 1.56 (m, 2H), 1.78 (m, 4H), 3.30 (m, 1H), 3.40 (m, 4H), 5.84 (s, 2H), 6.91-7.59 (m, 8H), 9.51 (s, 1H) | DMSO-d$_6$ | |
| 163 | N-hydroxy-4-5-[4-(5-cyclopentylmethyl-2-dimethylamino-1,3-thiazol-4-yl)phenoxy]pentoxy-benzamidine | cyclopentyl-propionylchloride | thiourea | iodomethane | 1.10-1.18 (m, 2H), 1.44-1.57 (m, 6H), 1.70-1.79 (m, 6H), 1.98-2.01 (m, 1H), 2.69 (d, 2H), 2.98 (s, 6H), 3.97-4.02 (m, 4H), 5.77 (s, 2H), 6.90-6.94 (d-d, 4H), 7.42 (d, 2H), 7.59 (d, 2H), 9.48 (s, 1H) | DMSO-d$_6$ | |

Examples 164 to 176

Compound (20) prepared according to the same method as that in the Preparative Example 4 was reacted in the same manner as Example, 1, obtaining the title compounds shown I Table 5.

Table 5 shows the title compounds, reactants and $^1$H-NMR data.

TABLE 5

| example | name | Acid chloride | Thioamide | Alkylhalide | NMR | solvent | mp |
|---|---|---|---|---|---|---|---|
| 164 | N-hydroxy-4-5-[4-(5-methyl-2-piperidino-1,3- | propionylchloride | thiourea | 1,5-dibromo-pentane | 1.56 (m, 2H), 1.63 (brm, 6H), 1.78 (brm, 4H), 3.60 (brm, 4H), 4.02 (t, 2H), 4.06 (t, 2H), 7.04 (d, 2H), 7.09 (d, 2H), | DMSD-d$_6$ + TFA-d$_1$ | |

TABLE 5-continued

| example | name | Acid chloride | Thioamide | Alkylhalide | NMR | solvent | mp |
|---|---|---|---|---|---|---|---|
| | thiazol-4-yl)phenoxy]pentoxy-benzamidine | | | | 7.40 (d, 2H), 7.66 (d, 2H) | | |
| 165 | N-hydroxy-4-5-[4-(5-methyl-2-morpholine-1,3-thiazol-4-yl)phenoxy]pentoxy-benzamidine | propionylchloride | thiourea | bisdibromid-ethylester | 1.56 (m, 2H), 1.78 (brm, 4H), 2.21 (s, 3H), 3.60 (brm, 4H), 3.74 (brm, 4H), 4.02 (t, 2H), 4.05 (t, 2H), 7.03 (d, 2H), 7.09 (d, 2H), 7.40 (d, 2H), 7.65 (d, 2H) | DMSD-$d_6$ + TFA-$d_1$ | |
| 166 | N-hydroxy-4-5-[4-(5-ethyl-2-piperidino-1,3-thiazol-4-yl)phenoxy]pentoxy-benzamidine | butrylchloride | thiourea | 1,5-dibromo-pentane | 1.09 (t, 3H), 1.55 (m, 2H), 1.61 (brm, 6H), 1.77 (brm, 4H), 2.56 (q, 2H), 3.59 (brm, 4H), 4.00 (t, 2H), 4.03 (t, 2H), 7.01 (d, 2H), 7.06 (d, 2H), 7.34 (d, 2H), 7.64 (d, 2H) | DMSD-$d_6$ + TFA-$d_1$ | |
| 167 | N-hydroxy-4-5-[4-(5-cyclopentylmethyl-2-piperidino-1,3-thiazol-4-yl)phenoxy]pentoxy-benzamidine | cyclopentyl-propionylchloride | thiourea | 1,5-dibromo-pentane | 1.01 (brm, 2H), 1.43 (brm, 4H), 1.56 (brm, 2H), 1.63 (brm, 8H), 1.78 (brm, 4H), 1.94 (m, 1H), 2.56 (d, 2H), 3.61 (brm, 4H), 4.05 (m, 4H), 7.04 (d, 2H), 7.10 (d, 2H), 7.36 (d, 2H), 7.66 (d, 2H) | DMSD-$d_6$ + TFA-$d_1$ | |
| 168 | N-hydroxy-4-5-[4-(5-cyclopentylmethyl-2-morpholino-1,3-thiazol-4-yl)phenoxy]pentoxy-benzamidine | cyclopentyl-propionylchloride | thiourea | bisdibromid-ethylester | 1.02 (brm, 2H), 1.43 (brm, 4H), 1.56 (brm, 2H), 1.66 (brm, 2H), 1.78 (brm, 4H), 1.94 (m, 1H), 2.58 (d, 2H), 3.61 (brm, 4H), 3.74 (brm, 4H), 4.05 (m, 4H), 7.04 (d, 2H), 7.09 (d, 2H), 7.36 (d, 2H), 7.65 (d, 2H) | DMSD-$d_6$ + TFA-$d_1$ | |
| 169 | N-hydroxy-4-(5-[4-(5-isopropyl-2-morpholin-4-yl-1,3-thiazol-4-yl)phenoxy]pentoxy)-benzamidine | isovaleryl-chloride | thiourea | bisdibromid-ethylester | 1.22 (d, 6H), 1.58 (m, 2H), 1.78 (m, 4H), 3.26 (m, 1H), 3.35 (m, 4H), 3.70 (m, 4H), 4.02 (m, 4H), 5.71 (brs, 2H), 6.95 (m, 4H), 7.40 (d, 2H), 7.58 (d, 2H), 9.44 (s, 1H) | DMSO-$d_6$ | |
| 170 | N-hydroxy-4-(5-4-[5-cyclopentylmethyl-2-(4-methylpiperazino)-1,3-thiazol-4-yl]phenoxypentoxy)-benzamidine | cyclopentyl-propionylchloride | thiourea | mechlore-thamine | 1.11 (brm, 2H), 1.52-1.56 (brm, 6H), 1.77 (brm, 6H), 2.00 (m, 1H), 2.50 (m, 2H), 2.69 (m, 2H), 3.00 (s, 3H), 3.33 (m, 4H), 3.55 (m, 6H), 4.00 (m, 4H), 5.81 (brs, 2H), 6.93 (m, 4H), 7.40 (d, 2H), 7.57 (d, 2H), 9.50 (brs, 1H) | DMSO-$d_6$ | |
| 171 | N-hydroxy-4-[5-[4-(5-vinyl-2-morpholin-4-yl-1,3-thiazol-4-yl)phenoxy]pentoxy)-benzamidine | 4-chlorobutryl-chloride | thiourea | bisdibromid-ethylether | 1.55 (m, 2H), 1.79 (m, 4H), 3.17 (d, 1H), 3.35 (m, 4H), 3.42 (m, 2H), 3.72 (m, 4H), 4.01 (m, 4H), 5.74 (s, 2H), 6.92 (m, 4H), 7.60 (d, 2H), 7.77 (d, 2H), 9.45 (s, 1H) | DMSO-$d_6$ | |
| 172 | N-hydroxy-4-(5-[4-(5-cyclopentyl-2-morpholin-4-yl-1,3-thiazol-4-yl)phenoxy]pentoxy)-benzamidine | cyclopentylethyl-chloride | thiourea | bisdibromid-ethylether | 1.58-1.60 (m, 7H), 1.74-1.81 (m, 7H), 2.51 (m, 4H), 3.34-3.36 (m, 1H), 3.69-3.71 (m, 4H), 4.00-4.02 (m, 4H), 5.77 (s, 2H), 6.92-6.98 (m, 4H), 7.42 (d, 2H), 7.59 (d, 2H), 9.48 (s, 1H) | DMSO-$d_6$ | |
| 173 | N-hydroxy-4-(5-[4-(5-isobutyl-2-morpholin-4-yl-1,3-thiazol-4-yl)phenoxy]pentoxy)-benzamidine | isocaproyl-chloride | thiourea | bisdibromid-ethylether | 0.88 (d, 6H), 1.59 (m, 2H), 1.80 (m, 4H), 2.60 (m, 1H), 3.35 (m, 8H), 3.70 (m, 2H), 4.01 (m, 4H), 5.77 (brs, 2H), 6.94 (m, 4H), 7.44 (m, 2H), 7.59 (m, 2H), 9.48 (brs, 1H) | DMSO-$d_6$ | |
| 174 | N-hydroxy-4-(5-4-[5-ethyl-2-(4-methylpiperazino)-1,3-thiazol-4-yl]phenoxypentoxy)-benzamidine | butrylchloride | thiourea | mechlore-thamine | 1.19 (t, 3H), 1.50-1.59 (m, 2H), 1.80 (m, 4H), 2.21 (s, 3H), 2.41 (m, 4H), 3.36 (m, 6H), 4.01 (m, 4H), 5.71 (brs, 2H), 6.93-6.96 (m, 4H), 7.44 (m, 2H), 7.58 (m, 2H), 9.46 (brs, 1H) | DMSO-$d_6$ | |
| 175 | N-hydroxy-4-(5-[4-(2-morpholin-4-yl-1,3-thiazol-4-yl)phenoxy]pentoxy)-benzamidine | propionylchloride | thiourea | bisdibromid-ethylether | 1.56 (m, 2H), 1.77 (m, 4H), 3.42 (m, 8H), 3.98 (m, 4H), 5.73 (brs, 2H), 6.81 (m, 2H), 6.92 (m, 2H), 7.11 (s, 1H), 7.27 (m, 2H), 7.77 (m, 2H), 8.35 (brs, 1H) | DMSO-$d_6$ | |

TABLE 5-continued

| example | name | Acid chloride | Thioamide | Alkylhalide | NMR | solvent | mp |
|---|---|---|---|---|---|---|---|
| 176 | N-hydroxy-4-(5-4-[5-isopropyl-2-(4-methylpiperazino)-1,3-thiazol-4-yl]phenoxypentoxy)-benzamidine | isovaleryl-chloride | thiourea | mechlore-thamine | 1.23 (d, 6H), 1.58 (m, 2H), 1.77 (m, 4H), 2.21 (s, 3H), 2.40 (m, 4H), 2.21 (s, 3H), 2.40 (m, 4H), 3.33 (m, 1H), 3.35 (m, 4H), 4.00 (m, 4H), 5.71 (s, 2H), 6.93-6.97 (m, 4H), 7.40 (d, 2H), 7.58 (d, 2H), 9.45 (s, 1H) | DMSO-$d_6$ | |

Examples 177 to 213

Compound (12) prepared according to the same method as that in the Preparative Example 1-6 was reacted in the same manner as Example 1, obtaining the title compounds shown I Table 6.

Table 6 shows the title compounds, reactants and $^1$H-NMR data.

TABLE 6

| example | name | Acid chloride | Thioamide | Alkylhalide | NMR | solvent | mp |
|---|---|---|---|---|---|---|---|
| 177 | N-hydroxy-4-(5-[4-(5-isopropyl-2-methyl-1,3-thiazol-4-yl)-phenoxy]-pentylamino)-benzamidine | isovalerylchloride | thioacetamide | — | 1.23 (d, 6H), 1.52 (m, 2H), 1.60 (m, 2H), 1.75 (m, 2H), 2.60 (s, 3H), 3.03 (m, 2H), 3.32 (m, 1H), 4.00 (t, 2H), 5.52 (s, 2H), 5.79 (m, 1H), 6.51 (d, 2H), 6.99 (d, 2H), 7.37 (d, 2H), 7.42 (d, 2H), 9.19 (s, 1H) | DMSO-$d_6$ | |
| 178 | N-hydroxy-4-2-[2-(4-(5-isopropyl-2-methyl-1,3-thiazol-4-yl)-phenoxy)-ethoxy]-ethoxy-benzamidine | " | " | — | 1.25 (d, 6H), 2.64 (s, 3H), 3.33 (m, 1H), 3.90 (m, 4H), 4.14 (m, 4H), 6.90 (m, 4H), 7.40 (m, 4H) | CDCl$_3$ | |
| 179 | N-hydroxy-4-(3-hydroxy-5-[4-(5-isopropyl-2-methyl-1,3-thiazol-4-yl)-phenoxy)-3-methyl-pentyloxy]-benzamidine | " | " | — | 1.26 (d, 6H), 1.32 (s, 3H), 2.06 (m, 4H), 2.65 (s, 3H), 3.33 (m, 1H), 4.20 (m, 4H), 5.01 (brs, 1H), 6.86 (d, 2H), 6.92 (d, 2H), 7.43 (d, 2H), 7.50 (d, 2H) | CDCl$_3$ | |
| 180 | N-hydroxy-4-(2-(2-[4-(5-isopropyl-2-methyl-1,3-thiazol-4-yl)-phenoxy]-1-methyl-ethylamino)-ethoxy)-benzamidine | " | " | — | 1.10 (d, 3H), 1.23 (d, 6H), 2.59 (s, 3H), 2.96 (m, 2H), 3.05 (m, 1H), 3.32 (m, 2H), 3.90 (m, 2H), 4.04 (m, 2H), 5.71 (s, 2H), 6.92 (d, 2H), 6.99 (d, 2H), 7.43 (d, 2H), 7.58 (d, 2H), 9.45 (s, 1H) | DMSO-$d_6$ | |
| 181 | N-hydroxy-4-3-[4-(3-(4-(5-isopropyl-2-methyl-1,3-thiazol-4-yl)-phenoxy)-propyl)-piperazin-1-yl]-propoxy-benzamidine | " | " | — | 1.23 (d, 6H), 1.85 (m, 4H), 2.40 (brm, 12H), 2.45 (s, 3H), 3.30 (m, 1H), 4.00 (m, 4H), 5.70 (s, 2H), 6.89 (d, 2H), 6.94 (d, 2H), 7.41 (d, 2H), 7.57 (d, 2H), 9.51 (s, 1H) | DMSO-$d_6$ | |
| 182 | N-hydroxy-4-5-[4-(5-isopropyl-2-methyl-1,3-thiazol-4-yl)-phenoxy]-pentanoyl-amino-benzamidine | " | " | — | 1.23 (d, 6H), 1.77 (brs, 4H), 2.40 (m, 2H), 2.60 (s, 3H), 3.33 (m, 1H), 4.02 (brs, 2H), 5.72 (s, 2H), 6.99 (d, 2H), 7.43 (d, 2H), 7.58-7.80 (m, 4H), 9.51 (s, 1H), 10.00 (s, 1H) | DMSO-$d_6$ | |
| 183 | N-hydroxy-4-5-[4-(5-isopropyl-2-methyl-1,3-thiazol-4-yl)-phenoxy]-pentyl-methyl-amino-benzamidine | " | " | — | 1.22 (d, 6H), 1.43 (m, 2H), 1.55 (m, 2H), 1.76 (m, 2H), 2.59 (s, 3H), 2.89 (s, 3H), 3.33 (m, 1H), 3.98 (m, 2H), 5.55 (s, 2H), 6.64 (d, 2H), 6.97 (d, 2H), 7.45 (m, 4H), 9.23 (s, 1H) | DMSO-$d_6$ DMSO-$d_6$ | |
| 184 | N-hydroxy-4-4-[4-(5-isopropyl-2-methyl-1,3-thiazol-4-yl)-phenoxy]-2-butenyloxy-benzamidine | isovalerylchloride | thioacetamide | — | 1.23 (d, 6H), 2.60 (s, 3H), 3.31 (m, 1H), 4.63 (brs, 4H), 5.73 (s, 2H), 6.08 (brs, 2H), 6.94 (d, 2H), 7.01 (d, 2H), 7.44 (d, 2H), 7.58 (d, 2H), 9.46 (s, 1H) | DMSO-$d_6$ | |
| 185 | N-hydroxy-4-(4-[4-(5-isopropyl-2- | " | " | — | 1.23 (d, 6H), 2.64 (s, 3H), 3.32 (m, 1H), 5.15 (s, 2H), | DMSO-$d_6$ | |

TABLE 6-continued

| example | name | Acid chloride | Thioamide | Alkylhalide | NMR | solvent | mp |
|---|---|---|---|---|---|---|---|
| | methyl-1,3-thiazol-4-yl)-phenoxymethyl]-benzyloxy)-benzamidine | | | | 5.23 (s, 2H), 5.72 (s, 2H), 7.07 (d, 2H), 7.19 (d, 2H), 7.46 (m, 6H), 7.73 (d, 2H), 9.46 (s, 1H) | | |
| 186 | N-hydroxy-4-(2-(2-[4-(5-isopropyl-2-methyl-1,3-thiazol-4-yl)phenoxy]-ethylamino)-ethoxy)-benzamidine | " | " | — | 1.23 (d, 6H), 2.59 (s, 3H), 3.01 (brs, 4H), 3.33 (m, 1H), 4.09 (m, 4H), 5.71 (s, 2H), 6.92 (d, 2H), 7.00 (d, 2H), 7.43 (d, 2H), 7.58 (d, 2H), 9.45 (s, 1H) | DMSO-$d_6$ | |
| 187 | N-hydroxy-2-fluoro-4-(5-[4-(5-isopropyl-2-methyl-1,3-thiazol-4-yl)-phenoxy]-pentyloxy)-benzamidine | " | " | — | 1.23 (d, 6H), 1.57 (m, 2H), 1.79 (m, 4H), 2.49 (s, 3H), 3.33 (m, 1H), 4.02 (m, 4H), 5.70 (s, 2H), 6.83 (m, 2H), 6.98 (d, 2H), 7.43 (m, 3H), 9.51 (s, 1H) | DMSO-$d_6$ | |
| 188 | 2,N-dihydroxy-4-(5-[4-(5-isopropyl-2-methyl-1,3-thiazol-4-yl)-phenoxy]-pentyloxy)-benzamidine | " | " | — | 1.23 (d, 6H), 1.56 (m, 2H), 1.77 (m, 4H), 2.60 (s, 3H), 3.32 (m, 1H), 4.00 (m, 4H), 6.25 (s, 2H), 6.36 (m, 2H), 7.00 (d, 2H), 7.42 (d, 2H), 7.52 (d, 1H), 9.81 (s, 1H), 12.40 (s, 1H) | DMSO-$d_6$ | |
| 189 | N-hydroxy-4-(5-[4-(5-isopropyl-2-methyl-1,3-thiazol-4-yl)-phenoxy]-pentyloxy)-3-methoxy-benzamidine | " | " | — | 1.24 (d, 6H), 1.58 (m, 2H), 1.80 (m, 4H), 2.61 (s, 3H), 3.35 (m, 1H), 3.77 (s, 3H) 4.02 (m, 4H), 5.77 (s, 2H), 6.98 (m, 3H), 7.26 (m, 2H), 7.46 (d, 2H), 9.48 (s, 1H) | DMSO-$d_6$ | |
| 190 | N-hydroxy-2-cyclohexylamino-4-(5-[4-(5-isopropyl-2-methyl-1,3-thiazol-4-yl)-phenoxy]-pentyloxy)-benzamidine | " | " | — | 1.23 (m, 12H), 1.54 (m, 2H), 1.65 (m, 2H), 1.76 (m, 4H), 1.78 (m, 2H), 2.60 (s, 3H), 3.34 (m, 1H), 3.99 (m, 4H), 5.66 (s, 2H), 6.09 (m, 2H), 6.97 (d, 2H), 7.31 (d, 1H), 7.43 (d, 2H), 7.70 (d, 1H), 9.48 (s, 1H) | DMSO-$d_6$ | |
| 191 | N-hydroxy-4-(5-[3-fluoro-4-(5-isopropyl-2-methyl-1,3-thiazol-4-yl)-phenoxy]-pentyloxy)-benzamidine | " | " | — | 1.17 (d, 6H), 1.57 (m, 2H), 1.79 (brs, 4H), 2.98 (m, 1H), 4.04 (m, 4H), 5.71 (s, 2H), 6.90 (m, 3H), 7.31 (d, 2H), 7.59 (d, 2H), 9.44 (s, 1H) | DMSO-$d_6$ | |
| 192 | N-hydroxy-2-fluoro-4-(5-[3-fluoro-4-(5-isopropyl-2-methyl-1,3-thiazol-4-yl)-phenoxy]-pentyloxy)-benzamidine | isovalerylchloride | thioacetamide | — | 1.17 (d, 6H), 1.57 (brs, 2H), 1.79 (brs, 4H), 2.98 (m, 1H), 4.05 (m, 4H), 5.73 (s, 2H), 6.82-6.89 (m, 4H), 7.27-7.40 (m, 2H), 9.52 (s, 1H) | DMSO-$d_6$ | |
| 193 | N-hydroxy-4-(3-[4-(5-isopropyl-2-methyl-1,3-thiazol-4-yl)phenoxy]propoxy)-benzamidine | " | " | — | 1.24 (d, 6H), 2.20 (m, 2H), 2.60 (s, 3H), 3.30 (m, 1H), 4.17 (m, 4H), 5.71 (s, 2H), 6.96 (d, 2H), 7.01 (d, 2H), 7.44 (d, 2H), 7.60 (d, 2H), 9.45 (s, 1H) | DMSO-$d_6$ | |
| 194 | N-hydroxy-4-(4-[4-(5-isopropyl-2-methyl-1,3-thiazol-4-yl)phenoxy]butoxy)-benzamidine | " | " | — | 1.26 (d, 2H), 1.89 (m, 4H), 2.60 (s, 3H), 3.30 (m, 1H), 4.06 (m, 4H), 5.72 (s, 2H), 6.92 (d, 2H), 7.00 (d, 2H), 7.44 (d, 2H), 7.60 (d, 2H), 9.45 (s, 1H) | DMSO-$d_6$ | |
| 195 | N-hydroxy-3-(5-[4-(5-isopropyl-2-methyl-1,3-thiazol-4-yl)-phenoxy]-pentylamino)-benzamidine | " | " | — | 1.24 (d, 6H), 1.50-1.62 (m, 3H), 1.77-1.79 (m, 2H), 2.65 (s, 3H), 3.02-3.04 (m, 1H), 3.37-3.44 (m, 3H), 3.99-4.03 (m, 2H), 6.57-6.98 (m, 4H), 7.00 (d, 2H), 7.44 (d, 2H) | DMSO-$d_6$ | |
| 196 | N-hydroxy-4-(4-[4-(2-cyclohexyl-5-ethyl-1,3-thiazol-4-yl)-phenoxy]-butoxy)-benzamidine | butrylchloride | cyclohexan-carbothioic acid amide | — | 1.22 (t, 3H), 1.39-1.44 (m, 3H), 1.59 (m, 1H), 1.77 (m, 2H), 1.89 (m, 4H), 2.03 (m, 2H), 2.90 (m, 3H), 4.18 (m, 4H), 7.00 (m, 4H), 7.49 (m, 2H), 7.60 (m, 2H) | DMSO-$d_6$ | |

TABLE 6-continued

| example | name | Acid chloride | Thioamide | Alkylhalide | NMR | solvent | mp |
|---|---|---|---|---|---|---|---|
| 197 | N-hydroxy-4-[5-(4-5-ethyl-2-[(2-hydroxyethyl)-methyl-amino]-1,3-thiazol-4-yl-phenoxy)propoxy]-benzamidine | " | thiourea | bromoethanol | 1.17 (m, 3H), 2.19 (m, 2H), 2.72 (m, 2H), 3.05 (s, 3H), 3.39-3.79 (m, 4H), 4.16-4.20 (m, 4H), 5.72 (s, 2H), 6.96 (m, 4H), 7.40-7.84 (m, 4H), 9.47 (s, 1H) | DMSO-$d_6$ | |
| 198 | N-hydroxy-4-[5-(4-5-ethyl-2-[(2-hydroxyethyl)-methyl-amino]-1,3-thiazol-4-yl-phenoxy)butoxy]-benzamidine | " | " | " | 1.15 (t, 3H), 1.90 (m, 4H), 2.64 (q, 2H), 3.25 (s, 3H), 3.40-3.80 (m, 4H), 4.10-4.15 (m, 4H), 7.09-7.15 (m, 4H), 7.42 (d, 2H), 7.73 (d, 2H) | DMSO-$d_6$ | |
| 199 | N-hydroxy-4-[5-(4-5-ethyl-2-[methyl-(pyridin-3-yl-methyl)amino]-1,3-thiazol-4-yl-phenoxy)propoxy]-benzamidine | " | thiourea | 3-bromo-methylpyridin | 1.86 (t, 3H), 2.50 (m, 2H), 2.73 (m, 2H), 3.15 (s, 3H), 4.17-4.25 (m, 4H), 4.96 (s, 2H), 7.01 (d, 2H), 7.17 (d, 2H), 7.44 (d, 2H), 7.73 (d, 2H), 8.06 (m, 1H), 8.54 (d, 1H), 8.87 (d, 1H), 8.94 (s, 1H) | DMSO-$d_6$ | |
| 200 | N-hydroxy-4-[5-(4-5-ethyl-2-[methyl-(pyridin-3-yl-methyl)amino]-1,3-thiazol-4-yl-phenoxy)butoxy]-benzamidine | " | " | 3-bromo-methylpyridin | 1.19 (t, 3H), 1.79-1.89 (m, 4H), 2.72-2.74 (m, 2H), 3.17 (s, 3H), 4.07-4.15 (m, 4H), 4.98 (s, 2H), 7.00 (d, 2H), 7.14 (d, 2H), 7.44 (d, 2H), 7.72 (d, 2H), 8.05 (m, 1H), 8.55 (d, 1H), 8.87 (d, 1H), 8.95 (s, 1H) | DMSO-$d_6$ | |
| 201 | N-hydroxy-4-(4-[4-(5-cyclopentylmethyl-2-isopropyl-1,3-thiazol-4-yl)-phenoxymethyl]-benzyloxy)-benzamidine | cyclopentyl-propionylchloride | thioisobutyl-amide | — | 1.14 (m, 2H), 1.32 (d, 6H), 1.48 (m, 4H), 1.74 (m, 2H), 2.04 (m, 1H), 2.85 (d, 2H), 3.38 (m, 1H), 5.14 (s, 4H), 5.73 (s, 2H), 7.01 (d, 2H), 7.08 (d, 2H), 7.48 (s, 4H), 7.50 (d, 2H), 7.58 (d, 2H), 9.48 (s, 1H) | DMSO-$d_6$ | |
| 202 | N-hydroxy-4-(4-[4-(5-butyl-2-isopropyl-1,3-thiazol-4-yl)-phenoxymethyl]-benzyloxy)-benzamidine | hexanoylchloride | thioisobutyl-amide | — | 0.85 (t, 3H), 1.32 (d, 6H), 1.35 (m, 2H), 1.60 (m, 2H), 1.85 (m, 2H), 3.25 (m, 1H), 5.15 (s, 4H), 5.74 (s, 2H), 7.01 (d, 2H), 7.08 (d, 2H), 7.48 (s, 4H), 7.50 (d, 2H), 7.60 (d, 2H), 9.49 (s, 1H) | DMSO-$d_6$ | |
| 203 | N-hydroxy-4-(4-[4-(5-cyclopentylmethyl-2-amino-1,3-thiazol-4-yl)-phenoxymethyl]-benzyloxy)-benzamidine | cyclopentyl-propionylchloride | thiourea | — | 1.07-1.09 (m, 2H), 1.47-1.50 (m, 4H), 1.70 (m, 2H), 1.99 (m, 1H), 2.34 (s, 6H), 2.62 (d, 2H), 5.18 (s, 2H), 5.25 (s, 2H), 7.17-7.24 (m, 4H), 7.41 (d, 2H), 7.50 (m, 4H), 7.68 (d, 2H) | DMSO-$d_6$ | |
| 204 | N-hydroxy-4-(4-[4-(5-cyclopentylmethyl-2-amino-1,3-thiazol-4-yl)-phenoxymethyl]-benzyloxy)-2-fluoro-benzamidine | cyclopentyl-propionylchloride | " | — | 1.05 (m, 2H), 1.49 (m, 4H), 1.71 (m, 2H), 2.00 (m, 1H), 2.34 (s, 6H), 2.63 (d, 2H), 5.15-5.26 (d, 4H), 7.05-7.24 (m, 3H), 7.41-7.62 (m, 8H) | DMSO-$d_6$ | |
| 205 | N-hydroxy-4-(4-[4-(2-methylamino-1,3-thiazol-4-yl)-phenoxymethyl]-benzyloxy)-benzamidine | acetylchloride | " | iodomethane | 2.86 (s, 3H), 5.16 (m, 4H), 6.00 (brs, 2H), 7.02 (m, 4H), 7.48 (m, 4H), 7.60 (s, 1H), 7.76 (m, 4H), 9.57 (brs, 1H) | DMSO-$d_6$ | |
| 206 | N-hydroxy-4-(6-[4-(5-isopropyl-2-methyl-1,3-thiazol-4-yl)-phenoxymethyl]-pyridin-2-yl-methoxy)-benzamidine | isovalerylchloride | thioacetamide | — | 1.26 (d, 6H), 2.61 (s, 3H), 3.35 (m, 1H), 5.25 (m, 4H), 5.75 (brs, 2H), 7.11 (m, 1H), 7.13 (m, 2H), 7.47 (m, 4H), 7.49 (m, 2H), 7.80-7.90 (m, 2H), 9.49 (brs, 1H) | DMSO-$d_6$ | |
| 207 | N-hydroxy-2-fluoro-4-(5-[4-(5-isopropyl-2-methyl-1,3-thiazol-4-yl)-phenoxy]-butoxy)-benzamidine | " | " | — | 1.25 (d, 6H), 1.89 (m, 4H), 2.61 (s, 3H), 3.34 (m, 1H), 4.10 (m, 4H), 6.80-6.90 (m, 2H), 7.02 (m, 2H), 7.46 (m, 3H) | DMSO-$d_6$ | |
| 208 | N-hydroxy-4-(2-[4-(5-isopropyl-2-methyl-1,3-thiazol-4-yl)-phenoxymethyl]-benzyloxy)-benzamidine | " | " | — | 1.23 (d, 6H), 2.60 (s, 3H), 3.33 (m, 1H), 5.28 (s, 4H), 5.80 (s, 2H), 7.04-7.12 (m, 4H), 7.37 (m, 2H), 7.47 (d, 2H), 7.55 (m, 2H), 7.64 (d, 2H), 9.57 (s, 1H) | DMSO-$d_6$ | |

TABLE 6-continued

| example | name | Acid chloride | Thioamide | Alkylhalide | NMR | solvent | mp |
|---|---|---|---|---|---|---|---|
| 209 | N-hydroxy-4-(3-[4-(5-isopropyl-2-methyl-1,3-thiazol-4-yl)-phenoxymethyl]-benzyloxy)-benzamidine | " | " | — | 1.23 (d, 6H), 2.60 (s, 3H), 3.31 (m, 1H), 5.14 (s, 2H), 5.15 (s, 2H), 5.72 (s, 2H), 7.00 (d, 2H), 7.08 (d, 2H), 7.42-7.46 (m, 5H), 7.55-7.61 (m, 3H), 9.46 (s, 1H) | DMSO-$d_6$ | |
| 210 | N-hydroxy-4-(4-[4-(5-cyclopentylmethyl-2-cyclohexyl-1,3-thiazol-4-yl)-phenoxymethyl]-benzyloxy)-benzamidine | cyclopentyl-propionylchloride | cyclohexan-carbothioic acid amide | — | 1.10 (m, 2H), 1.23 (m, 1H), 1.46 (br, 9H), 1.77 (br, 4H), 2.02 (m, 3H), 2.83 (d, 2H), 2.90 (m, 1H), 5.16 (m, 4H), 5.81 (brs, 2H), 7.02 (m, 4H), 7.48 (m, 4H), 7.76 (m, 4H), 9.57 (brs, 1H) | DMSO-$d_6$ | |
| 211 | N-hydroxy-4-(6-[4-(5-isopropyl-2-methyl-1,3-thiazol-4-yl)phenoxy]-hexyloxy)-benzamidine | isovalerylchloride | thioacetamide | — | 1.24 (d, 6H), 1.49 (m, 4H), 1.76 (m, 4H), 2.61 (s, 3H), 3.32-3.37 (m, 1H), 3.99-4.02 (m, 4H), 5.81 (s, 2H), 6.91 (d, 2H), 6.99 (d, 2H), 7.44 (d, 2H), 7.59 (d, 2H), 9.49 (s, 1H) | DMSO-$d_6$ | |
| 212 | N-hydroxy-4-(5-[2-ethyl-5-hydroxy-4-(2-methyl-1,3-thiazol-4-yl)phenoxy]-pentyloxy)-benzamidine | butrylchloride | " | — | 1.13 (t, 3H), 1.61 (m, 2H), 1.81 (m, 4H), 2.51 (m, 2H), 2.79 (s, 3H), 3.97-4.10 (m, 4H), 6.60 (s, 1H), 7.12 (d, 2H), 7.69-7.86 (m, 4H), 8.81 (s, 1H), 9.26 (s, 1H) | DMSO-$d_6$ | |
| 213 | N-hydroxy-4-(5-[2-ethyl-4-(2-methyl-1,3-thiazol-4-yl)-5-propoxy-phenoxy]-pentyloxy)-benzamidine | butrylchloride | thioacetamide | — | 1.03 (t, 3H), 1.13 (t, 3H), 1.62 (m, 2H), 1.79-1.85 (m, 6H), 2.55 (m, 2H), 2.69 (s, 3H), 4.01-4.08 (m, 6H), 5.73 (s, 2H), 6.67 (s, 1H), 6.92 (d, 2H), 7.59-7.93 (m, 4H), 9.47 (s, 1H) | DMSO-$d_6$ | |

Experimental Example 1

Inhibitory Effects on Osteoclast Differentiation

The effect of benzamidine derivatives of the present invention on osteoclast proliferation and differentiation process was evaluated via co-culture with osteoblast.

1-1. Preparation of Cells
a) Preparation of Bone Marrow Cells

Tibia and Femora were aseptically ectomized from male ddY mice of 6-8 weeks to harvest bone marrow cells by using a syringe (21G, Korea Green Cross).

The bone marrow cells were suspended in 5 mL α-MEM medium (Gibco BRL Co.) containing sodium bicarbonate (2.0 g/L), streptomycin (100 mg/L) and penicillin (100,000 unit/mL). The harvested cells were centrifuged at 600×g for 5 mins to collect the whole quantity. To remove the red blood cells within bone marrow cells, 3 mL of Tris HCl (0.83% $NH_4Cl$, pH7.5) was added and well mixed. After centrifuging above cells, the numbers of bone marrow cells were counted and then, the bone marrow cells were immediately used for co-culture system with osteoblast.

b) Preparation of Osteoblast

The calvaria were aseptically ectomized from neonate ICR mice of 1~2 days, washed with PBS solution and incubated with a mixture of enzyme solution (0.2% collagenase and 0.1% dispase) at 37° C. gentle shaker. This procedure was sequentially repeated (10, 10, 10, 20, 20 and 20 mins), and then the calvaria cells having the characteristics of osteoblast mostly released from III-VI digestion groups were collected and washed with the medium (serum-free α-MEM). The washed cells were cultivated in α-MEM medium containing 10% FBS for 2~3 days. After subculturing, these cells were used for this experiment, and diluted to reach the concentration of $1\times10^6$ cell/mL for storage at −70° C.

1-2. Measurement of Osteoclast Differentiation
a) Preparation of Specimen

Benzamidine derivatives of the present invention were dissolved in a sterile distilled water or ethanol to make desired concentrations following dilution. The final volume of specimen added to the medium was determined at the ratio of 1:1000.

b) Reaction with Specimens Via Co-Culture System

Bone marrow cells prepared, in the above and osteoblast from calvaria were co-cultured for osteoclast differentiation. Both bone marrow cells (25,000 cells/cm$^2$) and osteoblast (10,000 cells/cm$^2$) were plated on a 96 well plate in α-MEM medium containing FBS with specimen, and then cultured with test materials for 7 days. Differentiation factors, such as dexamethasone ($10^{-7}$M) and vitamin $D_3$ ($10^{-8}$M), were also continuously added to the medium from the first day of cultivation. The medium was changed with fresh media containing a mixture of specimens and differentiation factors every 2~3 day.

c) Evaluation of Osteoclast Differentiation
1) Preparation of Tartarate Resistance Acid Phosphatase (TRAP) Staining Solution TRAP was used as a marker to measure osteoclast in consideration of its characteristics showing a positive reaction to TRAP staining solution. TRAP staining solution was prepared in a manner that 5 mg of naphtol AS-MS phosphate (sigma N-4875), a substrate and 25 mg of coloring agent (Fast Red Violet LB salt) were dissolved in N,N-dimethylformamide (about 0.5 mL), 0.1N $NaHCO_3$ buffer solution (50 mL) containing 50 mM tartaric acid was added, and the reaction mixture was stored at refrigerator prior to use.

2) Staining Method

After culturing the cells for 7 days, the medium was removed from the wells, the cells were once washed with PBS solution and fixed to PBS containing 10% formalin for 2~5 mins. The cells were fixed again in a mixed solution of ethanol and acetone (1/1) for about 1 min, and dried off. The cells were further treated by TRAP staining solution for 15 mins and washed with PBS. The experimental results were measured by counting the number of osteoclasts with 3 or more nuclei showing TRAP-positive reaction under a microscopic examination. Each of tests was confirmed over three times for gaining more reliable data.

As shown in the following table 7, the inhibitory effect of each experimental group on the differentiation of osteoclast versus controls was expressed by inhibitory percentage value.

TABLE 7

| sample | % inhibitory activity on osteoclastogenesis |
|---|---|
| | 1 μm |
| Example 1 | 87.0 |
| Example 2 | 78.4 |
| Example 3 | 41.4 |
| Example 4 | 81.1 |
| Example 5 | 87.5 |
| Example 6 | — |
| Example 7 | 94.5 |
| Example 8 | 88.3 |
| Example 9 | 100 |
| Example 10 | 1.8 |
| Example 11 | 53.2 |
| Example 12 | — |
| Example 13 | 73.5 |
| Example 14 | 89.2 |
| Example 15 | 68.3 |
| Example 16 | 64.3 |
| Example 17 | 59.1 |
| Example 18 | 24.8 |
| Example 19 | 42.6 |
| Example 20 | 35.6 |
| Example 21 | — |
| Example 22 | 92.6 |
| Example 23 | 47.7 |
| Example 24 | 57.8 |
| Example 25 | 26.5 |
| Example 26 | 42.9 |
| Example 27 | 56.5 |
| Example 28 | 29.6 |
| Example 29 | 96.3 |
| Example 30 | 47.7 |
| Example 31 | 35.6 |
| Example 32 | 59.4 |
| Example 33 | 49.5 |
| Example 34 | 28.7 |
| Example 35 | 69.8 |
| Example 36 | 46.4 |
| Example 37 | 52.9 |
| Example 38 | 56.8 |
| Example 39 | 37.5 |
| Example 40 | 60.1 |
| Example 41 | 64.0 |
| Example 42 | 90.9 |
| Example 43 | 98.6 |
| Example 44 | 96.6 |
| Example 45 | 97.7 |
| Example 46 | 96.9 |
| Example 47 | 90.0 |
| Example 48 | 72.1 |
| Example 49 | 77.1 |
| Example 50 | 79.8 |
| Example 51 | 74.8 |
| Example 52 | 0 |
| Example 53 | 0 |
| Example 54 | 94.2 |

TABLE 7-continued

| sample | % inhibitory activity on osteoclastogenesis |
|---|---|
| Example 55 | 67.8 |
| Example 56 | 58.7 |
| Example 57 | 60.4 |
| Example 58 | — |
| Example 59 | — |
| Example 60 | 28.2 |
| Example 61 | 0 |
| Example 62 | 19.1 |
| | 1 m |
| Example 63 | 56.5 |
| Example 64 | 43.7 |
| Example 65 | 46.0 |
| Example 66 | 38.5 |
| Example 67 | 81.4 |
| Example 68 | 83.0 |
| Example 69 | 99.6 |
| Example 70 | 32.7 |
| Example 71 | — |
| Example 72 | 67.9 |
| Example 73 | 54.2 |
| Example 74 | 92.6 |
| Example 75 | 40.2 |
| Example 76 | 99.0 |
| Example 77 | 83.3 |
| Example 78 | 97.5 |
| Example 79 | 96.4 |
| Example 80 | 96.4 |
| Example 81 | 29.5 |
| Example 82 | 8.9 |
| Example 83 | 23.8 |
| Example 84 | 100 |
| Example 85 | 5.3 |
| Example 86 | 52.9 |
| Example 87 | 58.1 |
| Example 88 | 15.9 |
| Example 89 | 81.2 |
| Example 90 | 61.9 |
| Example 91 | 92.9 |
| Example 92 | 49.0 |
| Example 93 | 63.7 |
| Example 94 | 77.2 |
| Example 95 | 47.1 |
| Example 96 | 64.3 |
| Example 97 | 42.6 |
| Example 98 | 94.7 |
| Example 99 | — |
| Example 100 | 63.0 |
| Example 101 | 43.7 |
| Example 102 | 96.4 |
| Example 103 | 25.4 |
| Example 104 | 40.0 |
| Example 105 | 61.1 |
| Example 106 | 0 |
| Example 107 | 53.2 |
| Example 108 | 25.4 |
| Example 109 | 80.5 |
| Example 110 | 100 |
| Example 111 | 99.5 |
| Example 112 | 76.8 |
| Example 113 | 86.7 |
| Example 114 | 50.9 |
| Example 115 | 96.0 |
| Example 116 | 51.3 |
| Example 117 | 2.7 |
| Example 118 | 82.9 |
| Example 119 | 92.6 |
| Example 120 | 35.7 |
| Example 121 | 69.4 |
| Example 122 | 55.8 |
| Example 123 | 26.3 |
| Example 124 | 87.9 |
| Example 125 | 73.0 |
| Example 126 | 71.2 |
| Example 127 | 41.5 |
| Example 128 | 75.5 |

TABLE 7-continued

| sample | % inhibitory activity on osteoclastogenesis |
|---|---|
| Example 129 | 64.7 |
| Example 130 | 55.8 |
| Example 131 | 69.0 |
| Example 132 | — |
| Example 133 | 76.6 |
| Example 134 | 63.7 |
| Example 135 | 48.6 |
| Example 136 | 49.2 |
| Example 137 | 62.7 |
| Example 138 | 91.0 |
| Example 139 | 84.1 |
| Example 140 | 18.9 |
| Example 141 | 74.8 |
| Example 142 | 54.1 |
| Example 143 | 69.5 |
| Example 144 | 94.4 |
| Example 145 | 96.2 |
| Example 146 | 94.4 |
| Example 147 | 81.1 |
| Example 148 | 90.1 |
| Example 149 | 79.2 |
| Example 150 | 95.4 |
| Example 151 | 93.0 |
| Example 152 | 83.8 |
| Example 153 | 96.4 |
| Example 154 | 9.3 |
| Example 155 | — |
| Example 156 | 15.6 |
| Example 157 | 92.3 |
| Example 158 | — |
| Example 159 | — |
| Example 160 | 83.7 |
| Example 161 | 89.1 |
| Example 162 | 87.4 |
| Example 163 | 88.1 |
| Example 164 | 67.4 |
| Example 165 | 66.9 |
| Example 166 | 81.2 |
| Example 167 | 99.0 |
| Example 168 | 87.0 |
| Example 169 | 83.3 |
| Example 170 | 93.9 |
| Example 171 | 96.2 |
| Example 172 | 87.8 |
| Example 173 | 9.0 |
| Example 174 | — |
| Example 175 | 61.9 |
| Example 176 | — |
| Example 177 | 96.1 |
| Example 178 | 36.8 |
| Example 179 | 100 |
| Example 180 | 32.6 |
| Example 181 | 54.1 |
| Example 182 | 81.1 |
| Example 183 | 65.6 |
| Example 184 | 74.5 |
| Example 185 | 89.4 |
| Example 186 | 71.0 |
| Example 187 | 92.5 |
| Example 188 | 82.6 |
| Example 189 | 38.7 |
| Example 190 | 27.3 |
| Example 191 | 8.8 |
| Example 192 | 70.5 |
| Example 193 | 54.1 |
| Example 194 | 19.8 |
| Example 195 | 42.3 |
| Example 196 | 82.0 |
| Example 197 | — |
| Example 198 | 36.9 |
| Example 199 | 82.9 |
| Example 200 | 38.7 |
| Example 201 | 85.6 |
| Example 202 | 85.6 |
| Example 203 | 68.8 |
| Example 204 | 45.-7 |
| Example 205 | — |
| Example 206 | — |
| Example 207 | 14.4 |
| Example 208 | — |
| Example 209 | 14.3 |
| Example 210 | 68.8 |
| Example 211 | 44.0 |
| Example 212 | — |
| Example 213 | 91.8 |

As shown in the table 7, the results indicate that the benzamidine derivatives were significantly inhibited the osteoclast differentiation at a low concentration.

Experimental Example 2

Effect on Bone Formation

The osteoblast, treated in this experiment, was prepared from the osteoblast as prepared in the above.

2-1: Experiment 1

The osteoblast, isolated from sequential enzymatic treatment of calvariae from neonated ICR mice, was cultured in α-MEM medium containing 10% FBS for 4~5 days. The osteoblast was also cultured for 24 hr after seeding the cells on a 12 well plate ($10^5$ cell/well), and medium was exchanged with the osteogenic differentiation medium containing 10 mM β-glycerophosphate and 50 μg/ml ascorbic acid.

The test substances at the concentration of 0.1 uM and 0.1 nM were added to the above medium for evaluating the effect promoting bone formation. The differentiation medium containing the test substances was exchanged every 3 or 4 days for 14 to 21 days until confirming the nodule mineralization.

The cell was rinsed twice with distilled water, and fixed by the 10% formalin solutions for 30 minutes. Alizarin red S and Von-kossa Solution were treated on the plate for measuring deposited calcium and phosphate in cell matrix, and the activity of the test substances on the bone formation was analyzed by determining stained area.

Additionally, for the purpose of estimating quantitative Arizarin red S in cell matrix, stained Arizarin red S was extracted by treating 10 mM sodium phosphate solution (pH 7.0), containing 10% cetylpyridinium chloride, for 15~30 minutes in the shaking incubator, and then the amount of the deposited calcium was estimated by calculating the absorbance of the extracted Arizarin red S at 564 nm.

2-2: Experiment 2

$1 \times 10^5$ of calvarial cells per well from neonated ICR mice were loaded on a 12 well plate and cultured for 24 h. The osteogenic differentiation medium containing 10 mM β-glycerophosphate and 50 μg/ml ascorbic acid was exchanged at the confluent state of the cell, and the compounds for investigating their activities on the osteoblast were added.

The differentiation medium containing the test substances was exchanged every 3 days, and the culturing period was prolonged approximately 15 days.

The medium containing the test compounds was removed from the cells at the end of culture and then, the cells were washed with sterilized distilled water once or twice and fixed to 10% formalin solution about 30-60 minutes. These fixed plates were again washed once or twice, and stained 40 mM Arizarin red S for 10 minutes after drying the plates. These stained plates were rinsed 3~5 times for eliminating waste Arizarin red S. For measuring the amount of the deposited Arizarin red S, 570 ul of 10% (w/v) cetylpyridinium chloride were added on plates, extracted and stained Arizarin red S for 15-30 minutes in the shaking incubator at 37° C. Finally, the amount of calcium was estimated by calculating the absorbance of the extracted Arizarin red S at 564 nm.

The results are listed in in Table 8.

TABLE 8

| sample | bone forming activity (%) | |
| --- | --- | --- |
| | 0.1 μM | 0.1 nM |
| Example 7 | 9.61 | 1.24 |
| Example 9 | 13.68 | 6.14 |
| Example 14 | 12.06 | 10.56 |
| Example 22 | 8.56 | 10.33 |
| Example 47 | 11.31 | 9.4 |
| Example 110 | 9.37 | 9.76 |
| Example 119 | 10.23 | 9.62 |
| Example 124 | 12.9 | 6.44 |
| Example 129 | 11.54 | 11.18 |
| Example 138 | 6.32 | 8.81 |

As shown in Table 8, benzamidine derivatives of the present invention have the excellent activities on the osteoblast, and thus these compounds are effective on the bone formation process.

Experimental Example 3

Therapeutic Effect in the Ovariectomized Osteoporetic Mouse Model of Each Test Substance The therapeutic effects of each benzamidine derivates were evaluated on the ovariectomized ddY mouse. Benzamidine derivates were dosed from 4 weeks after operation for 4 weeks and the changes on the trabecular bone volume (TBV) of the femur were observed via histomorphometry.

3-1. Animals and Husbandry

Female ddY mice (6-wk old upon receipt, SLC, Japan) were used after acclimatization for 7 days. Animals were allocated 5 per polycarbonate cage in a temperature (20-25° C.) and humidity (30-35%) controlled room. Light:dark cycle was 12 hr:12 hr and feed (Samyang, Korea) and water were supplied free to access.

3-2. Preparations and Administration of Drugs

Salts of benzamidine derivatives (Methansulfonic acid or HCl) were used for the test substances of this invention. Test substances are dissolved and/or suspended in injectable distilled water and administered at a dosage volume of 10 ml/kg by oral gavage. All test substances are dosed from 4 weeks after operation for 4 weeks at 50 mg/kg/day.

3-3. Ovariectomy

To induce estrogen-deficient osteoporosis, bilateral ovaries are removed and then closed by routine methods. Operation was conduct under Ketamine hydrochloride and xylazine hydrochloride anesthesia.

3-4. Histology

The left femur of each mouse were separated at sacrifice, and fixed in 10% neutral buffered formalin (NBF), then decalcified in decalcifying solution (24.4% formic acid, and 0.5N sodium hydroxide) for 5 days (mixed decalcifying solution was exchanges once a day for 5 days). After the dexalcification, the femur was embedded in paraffin, sectioned (3~4 μm) and stained with hematoxylin-eosin stain.

3-5. Histomorphometry

TBV was calculated using automated image analysis (analySIS Image Processing; SIS, Germany) under magnification of ×200 in the uniform area of trochlea epiphyseal regions (growth plate regions were excluded) of prepared histological specimens. TBV was calculated as percentage (%) levels.

3-6. Changes vs Vehicle Control

The changes of TBV compared to that of vehicle control are calculated as following Equation 1 to help the understanding of the efficacy of test substances.

Percentage changes=[((TBV of $a$−TBV of $b$)/TBV of $b$)×100]   Equation 1 a: test substance-dosing groups
b: vehicle control
Results are listed in Table 9.

TABLE 9

| sample | Changes on TBV (% changes vs vehicle control) |
| --- | --- |
| Example 13 | 81.97 |
| Example 21 | 75.49 |
| Example 23 | 28.03 |
| Example 43 | 154.8 |
| Example 47 | 139.8 |
| Example 111 | 69.26 |
| Example 119 | 144.2 |
| Example 124 | 72.82 |
| Example 138 | 164.17 |
| Example 145 | 91.68 |
| Example 165 | 37.52 |
| Example 167 | 55.2 |
| Example 168 | 56.6 |
| Example 169 | 186 |
| Example 177 | 88.66 |
| Example 184 | 146.66 |
| Example 185 | 152.06 |
| Example 187 | 117.19 |
| Example 188 | 91.96 |
| Example 152 | 71.48 |

As shown in the table 9, the experimental results indicate that the test substances have inhibitory effects on the decrease of bone volumes induced by ovariectomy. TBV of test substance-dosing groups are dramatically increased compared to that of vehicle control.

Therefore, it is considered that the test substances prove to be effective for the treatment of osteoporosis.

Experimental Example 4

Effect of Promoting Fracture Healing in Rib Fracture-Induced at Model

The benzamidine compounds were assayed for therapeutic effect on bone fracture in rat models subjected to rib fracture. Benzamidine derivates are dosed from 2 days after operation for 2 weeks, and the changes on the volume and histology of callus were observed.

4-1. Experimental Animals and Breeding Management

A total of 54 SD rats (8 weeks old upon receipt, Jung Ang Lab. Animal Co., Korea) were used. While being housed at a density of three to a plastic cage, the experimental animals were kept in a breeding room under controlled temperature (20-25° C.) and humidity (30-35%). Under light-dark cycles of 12 hours, the rats were allowed to have free access to feedstuff and tap water.

4-2. Preparations and Administration of Sample 200 mg of benzamidine compounds (Methansulfonic acid or Hydrochloride) were completely dissolved in 5 ml of sterilized distilled water. The benzamidine derivatives in the solutions was orally administered at doses of 200 mg per kg of body weight once a day for 2 weeks from day 2 of the surgery.

4-3. Induction of Rib-Fracture

8th and 9th rib of each animal was exposed by general operation under ketamine HCl and xylazine HCl anesthesia, and the exposed ribs were crossly dissected using surgical scissors. After rib-fracture, surgical wounds were closed with general skin suture.

4-4. Volume of Bony Callus

8th and 9th ribs of each animal were separated at sacrifice and then the long axis and short axis of callus were calculated as mm units. The volume of callus was calculated as following Equation 2.

Callus volume(mm$^3$)=$(a \times b^2)/2$   Equation 2 a: long diameter of bony callus
b: short diameter of bony callus
Results are listed in Table 10.

TABLE 10

| Sample | Changes on callus volume (mm$^3$) |
| --- | --- |
| Vehicle control | 37.22 ± 8.23 |
| Example 13 | 23.15 ± 7.85* |
| Example 47 | 27.56 ± 6.94** |
| Example 115 | 24.06 ± 9.64* |
| Example 119 | 25.92 ± 10.35** |
| Example 138 | 27.34 ± 5.46* |

*$p < 0.01$ compared to that of vehicle control
**$p < 0.05$ compared to that of vehicle control As shown in the table 10, the experimental results indicate that the callus volume of test substance-dosing groups are significantly ($p<0.01$ or $p<0.05$) decreased compared to that of vehicle control.

Therefore, it is considered that the test substances have facilitating effects on the disappearance of callus volume induced by rib-fracture.

4-5. Histopathological Observation

The 8th rib including fracture sites of each rat was separated and fixed in 10% neutral buffered formalin, and then decalcified in decalcifying solution (24.4% formic acid, and 0.5N sodium hydroxide) for 5 days (mixed decalcifying solution was exchanges once a day for 5 days). After decalcification, the rib was embedded in paraffin, sectioned (3~4 μm) and stained with hematoxylin-eosin or Masson's trichrome for composition of callus observation.

Osteloid volume (OV/callus) in callus regions of prepared histological specimens were detected as % levels using automated image analysis (analySIS Image Processing; SIS, Germany) under microscopy.

Results are listed in Table 11.

TABLE 11

| sample | Changes on callus osteoid volume (OV/callus, %) |
| --- | --- |
| Vehicle control | 35.88 ± 5.06 |
| Example 13 | 43.19 ± 4.47** |
| Example 47 | 45.69 ± 7.07 |

TABLE 11-continued

| sample | Changes on callus osteoid volume (OV/callus, %) |
| --- | --- |
| Example 115 | 41.94 ± 6.33 |
| Example 119 | 50.18 ± 8.42* |
| Example 138 | 53.83 ± 7.84* |

*$p < 0.01$ compared to that of vehicle control
**$p < 0.05$ compared to that of vehicle control As shown in the table 11, the experimental results indicate that the callus osteoid volume of test substance-dosing groups are significantly ($p<0.01$ or $p<0.05$) increased compared to that of vehicle control.

Therefore, it is considered that the test substances have favorable effects on the facilitating the ossification in the callus induced by rib-fracture.

Experimental Example 5

Therapeutic Effect in Mouse Model of Asthma Induced with Ovalbumin

The benzamidine compounds were assated for therapeutic effect on allergic inflammation in mouse models of ovalbumin-induced asthma. Starting on the day of immunization the benzamidine compounds were dosed for 17 consecutive days. The experimental animals were re-exposed to ovalbumin 14 days after the sensitization and then sacrificed 3 days after the re-exposure. Changes in lung weight, cellular components of peripheral blood and bronchoalveolar lavage fluid, and lung histopathology were observed.

5-1. Experimental Animals and Breeding Management

A total of 110 female C57BL/6 mice (7-week-old, SLC, Japan) were adapted to a laboratory environment for 6 days before being used in earnest experiments. While being housed at a densirt of five in a plastic cage, the experimental animals were breed in a breeding room with controlled temperature (20-25° C.) and humidity (30-35%). Under light-dark cycles of 12 hours, mice were allowed to have free access to feedstuff and tap water. While asthma was induced in 100 mice by ovalbumin, 10 mice were used as a non-treated group.

5-2. Preparations and Administration of Sample 200 mg of benzamidine compounds (Methansulfonic acid or Hydrochloride) were completely dissolved in 5 ml of sterilized distilled water. The benzamidine compound in the solutions was orally administered at doses of 200 mg per kg of body weight once a day from the day of the sensitization with ovalbumin. The control group was administered with equal volumes of sterilized distilled water in the same manner.

5-3. Asthma Induction by Immunization with and Exposure to Ovalbumine

A solution of 200 μg of ovalbumin (Grade VI; Sigma, st. Louis, Mo., USA) and 180 mg of aluminium hydroxide (Al(OH)$_3$, dried powder gel; Aldrich, Milwaukee, USA) in 4 ml of physiological saline was allowed to stand at 4° C. overnight and was administered to the experimental animals (200 μl, abdominal injection) for sensitization. As for the non-treated group, a solution of only aluminium hydroxide in saline was injected. 15 days after sensitization, a 1.5% ovalbumin solution was sprayed in air using a nebulizer, followed by exposing the experimental animals to the spray for 10 min to induce asthma therein. The non-treated group was exposed only to saline in the same manner. All the experimental animals were sacrificed 3 days after the exposure.

5-4. Measurement of Lung Weight

On the final day of experiment, the lungs were separated form adjacent organs. The removed lungs were weight among individual animals, the relative weight of the lungs was calculated as a percentage of body weight using the following Equation 3.

Relative weight of Lung(%)=(Absolute lung weight/Body weight)×100   Equation 3

Results are listed in Table 12.

TABLE 12

| Group | Changes on the lung weight | |
|---|---|---|
| | Absolute (g) | Relative (%) |
| Sham (?) | 0.110 ± 0.009 | 0.694 ± 0.049 |
| Vehicle control | 0.134 ± 0.012* | 0.780 ± 0.103** |
| Example 13 | 0.108 ± 0.009# | 0.695 ± 0.075 |
| Example 47 | 0.122 ± 0.010**, ## | 0.706 ± 0.059 |
| Example 115 | 0.114 ± 0.009# | 0.705 ± 0.046 |
| Example 119 | 0.113 ± 0.010# | 0.720 ± 0.103 |
| Example 138 | 0.113 ± 0.011# | 0.691 ± 0.065## |
| Example 169 | 0.113 ± 0.003# | 0.696 ± 0.032## |
| Example 185 | 0.116 ± 0.003# | 0.720 ± 0.061 |

*$p < 0.01$ compared to that of sham
**$p < 0.05$ compared to that of sham
$p < 0.01$ compared to that of vehicle control
$p < 0.05$ compared to that of vehicle control As shown in the table 12, significantly ($p<0.01$ or $p<0.05$) increase of absolute and relative lung weights are detected in vehicle control compared to those of sham. However, they were significantly ($p<0.01$ or $p<0.05$) or dramatically decreased in test substance-dosing groups compared to that of vehicle control.

Therefore, it is considered that the test substances inhibit the increase of lung weight induced by asthmatic changes.

5-5. Changes on the Total Count of Leukocytes in the Peripheral Blood and BALF a) Total Count of Leukocytes in Peripheral Blood On the final day of experiment, all the experimental animals were etherized and underwent laparotomy to expose the abdominal vena cava, from which 1 ml of blood was the taken. Using a hemocytometer, a blood sample was measured for total leukocyte counts in a $\times 10^3/1$ mm$^3$ units.

b) Total Count of Leukocytes in BALF

On the final day of experiment, secretions present in bronchi and alveola were examined for cyrological constitution. After veing etherized, the experimental animals were operated to open the cervical region and the thorax. The jugular vein was allowed to bleed, followed by endotracheal intubation. 3 ml of phosphate buffered saline was injected twice through the tube and the thorax was massaged for 30 sec to obtain cell suspension from the lungs. Using a hemocytometer, a blood sample was measured for total leukocyte counts in a $\times 10^5/1$ ml units.

Results are listed in Table 13.

TABLE 13

| Group | Total leukocytes in peripheral blood ($\times 10^3/1$ mm$^3$) | Total leukocytes in BALF ($\times 10^5/1$ ml) |
|---|---|---|
| Sham | 10.27 ± 0.93 | 51.75 ± 2.15 |
| Vehicle control | 14.49 ± 0.88* | 75.68 ± 4.67* |
| Example 13 | 14.06 ± 1.07* | 72.75 ± 4.88 |
| Example 47 | 12.55 ± 1.35*, # | 62.40 ± 7.56*, # |
| Example 119 | 13.83 ± 1.27* | 74.75 ± 6.33* |
| Example 138 | 13.60 ± 0.83*, # | 68.83 ± 5.29*, ## |
| Example 169 | 13.20 ± 2.22* | 72.25 ± 7.95* |
| Example 185 | 11.90 ± 1.45**, # | 66.47 ± 7.41*, # |

*$p < 0.01$ compared to that of sham
**$p < 0.05$ compared to that of sham
$p < 0.01$ compared to that of vehicle control
$p < 0.05$ compared to that of vehicle control As shown in the table 13, significant ($p<0.01$) increase of total leukocytes in peripheral blood and BALF are detected in vehicle control compared to those of sham, respectively. However, they were significantly ($p<0.01$ or $p<0.05$) or dramatically decreased in the test substance-dosing groups compared to that of vehicle control, respectively.

Therefore, it is considered that the test substances have favorable effects on the inhibition of the inflammatory responses induced by asthmatic changes.

Experimental Example 6

Cytotoxicity Test

Cytotoxic effect of benzamidine derivatives was evaluated by the experiment described below.

The test substance was diluted in appropriate solvent at $10^{-2}$M concentration. This substance was diluted in culture medium at $10^{-5}$ concentration, and loaded into a 96-well microplate in a dose of 100 μL per well. Cells to be used in cytotoxitic test were plated on a 96-well microplate in a dose of $1 \times 10^4$ cell/100 μL per well and cultured for 72 hrs. 25 μL of MTT [3-(4,5-dimethyl-2-thiazolyl)-2,5-diphenyl-2H-tetrazolium bromide] dissolved in PBS at 2 mg/mL were added before 4 hrs of the end of culture. After reaction, the plates were centrifuged, medium was decanted and 100 μL of DMSO was added to dissolve formazan. Lastly, the absorbance of developed plates was measured at 540 nm. Survival rates of the cells were showed by % concentration compared with the control group.

Results were displayed in table 14.

TABLE 14

| sample | Survival rates of the cells ($10^{-6}$M) | |
|---|---|---|
| | MC3T3-E1 | ST2 |
| Example 47 | 54.2 | 24.0 |
| Example 8 | 76.9 | 46.2 |
| Example 11 | 87.2 | 33.1 |
| Example 15 | 81.8 | 42.3 |
| Example 16 | 39.6 | 30.1 |
| Example 32 | 100.0 | 55.1 |
| Example 35 | 73.6 | 56.3 |
| Example 37 | 74.4 | 40.5 |
| Example 40 | 100.0 | 53.3 |
| Example 41 | 84.6 | 48.7 |
| Example 45 | 75.9 | 37.0 |
| Example 46 | 100.0 | 48.3 |
| Example 48 | 100.0 | 51.2 |
| Example 49 | 83.5 | 39.0 |
| Example 50 | 81.0 | 61.0 |
| Example 51 | 95.5 | 66.5 |
| Example 57 | 52.1 | 19.9 |
| Example 63 | 52.5 | 29.3 |
| Example 67 | 68.9 | 40.0 |
| Example 86 | 100.0 | 48.6 |

TABLE 14-continued

| sample | Survival rates of the cells ($10^{-6}$M) | |
|---|---|---|
| | MC3T3-E1 | ST2 |
| Example 87 | 97.3 | 49.8 |
| Example 88 | 94.3 | 48.7 |
| Example 91 | 41.3 | 20.8 |
| Example 93 | 66.8 | 55.0 |
| Example 96 | 65.1 | 27.8 |
| Example 98 | 77.1 | 26.9 |
| Example 100 | 62.8 | 39.1 |
| Example 107 | 65.2 | 43.9 |
| Example 109 | 65.7 | 39.0 |
| Example 112 | 86.7 | 63.6 |
| Example 118 | 75.3 | 53.2 |
| Example 121 | 100.0 | 41.4 |
| Example 125 | 57.6 | 47.9 |
| Example 126 | 42.7 | 31.8 |
| Example 130 | 100.0 | 37.2 |
| Example 133 | 62.6 | 46.4 |
| Example 134 | 43.9 | 37.4 |
| Example 136 | 48.5 | 29.9 |
| Example 139 | 77.4 | 48.1 |
| Example 141 | 52.8 | 27.9 |
| Example 146 | 88.4 | 38.2 |
| Example 147 | 100.0 | 42.4 |
| Example 166 | 71.2 | 52.4 |
| Example 181 | 99.5 | 36.7 |

As shown in table 14, benzamidine derivative shows little cytotoxicity.

Examples of preparation of this invention are following.

Formulation Example

1. Preparation of Powders

| Benzamidine derivatives | 2 g |
|---|---|
| lactose | 1 g |

2 g of benzamidine derivatives of the formula (1) was mixed with 1 g of lactose, thus preparing powder from the mixture with filling to a air tight bag.

2. Preparation of Tablets

| Benzamidine derivatives | 100 mg |
|---|---|
| corn starch | 100 mg |
| lactose | 100 mg |
| magnesium stearate | 2 mg |

After mixing all components, tablets are prepared by being tableted with generally used methods.

3. Preparation of Capsules

| Benzamidine derivatives | 100 mg |
|---|---|
| corn starch | 100 mg |
| lactose | 100 mg |
| magnesium stearate | 2 mg |

After mixing all components, capsules are prepared by being filled up to gelatin capsules with generally used methods.

4. Preparation of Injections

| Benzamidine derivatives | 10 µg/ml |
|---|---|
| dilute hydrochloric acid BP | to pH 3.5 |
| NaCl for injections BP | Max. 1 ml |

Benzamidine derivatives of the formula 1 was dissolved in adequate volume of NaCl for injections BP, then pH of the solution was controlled to pH 3.5 with dilute hydrochloric acid BP. The volume of the whole solution was fixed with NaCl for injections BP, and the solution was mixed fully. The solution was filled up to type I ampoule made with glass, then the ampoule was sealed under the upper air lattice by melting glass. The sealed ampoule was autoclaved under the condition of 120° C. for 15 mins or more to prepare the sterilized injection.

INDUSTRIAL APPLICABILITY

The novel benzamidine derivatives of the present invention remarkably suppress osteoclastic bone resorption, stimulate osteoblastic bone formation in very low concentrations and inhibit decreases of bone mass in osteoporosis animal models and thus are useful for the prevention and treatment of osteoporosis. Further, the compounds of the present invention activate the loss of bony callus and its ossification and thus are useful for the prevention and treatment of bone fractures. The compounds of the present invention are also useful for the prevention and treatment of allergic inflammatory diseases.

The invention claimed is:

1. Benzamidine derivative of the formula 1 or pharmaceutically acceptable salts thereof:

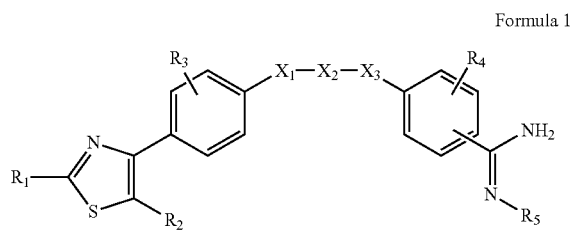

Formula 1 wherein $R_1$ is $C_3$-$C_6$ cycloalkyl; phenyl; benzyl; pyridinyl; guanidino; $NR_6R_7$; $CH_2NR_6R_7$;

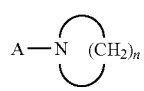

wherein A is $C_1$-$C_6$ alkyl and n is an integer of 2 to 6; $C_1$-$C_6$ alkyl which is substituted by pyridine; or pyridinyl which is substituted by $C_1$-$C_6$ alkyl;

$R_2$ is hydrogen; $C_1$-$C_6$ alkyl; $C_3$-$C_6$ cycloalkyl; phenyl; benzyl; $C_1$-$C_6$ alkyl which is substituted by hydroxy, $C_1$-$C_6$ alkoxy, halogen or $C_3$-$C_6$ cycloalkyl; or $C_2$-$C_6$ alkenyl;

R$_3$ and R$_4$, each independently, are hydrogen; halogen; hydroxy; C$_1$-C$_6$ alkyl which is unsubstituted or substituted halogen; C$_3$-C$_6$ cycloalkylamino; C$_1$-C$_6$ alkoxy; C$_1$-C$_6$ alkanoyloxy; C$_2$-C$_6$ alkenyloxy; phenyl-C$_1$-C$_6$ alkoxy; phenoxy; C$_2$-C$_6$ alkenoyloxy; phenyl-C$_1$-C$_6$ alkanoyloxy; C$_3$-C$_6$ cycloalkyloxy which is substituted by carboxy, esterified carboxy or amidated carboxy; or aminooxy;

R$_5$ is hydrogen or hydroxy;

R$_6$ and R$_7$, each independently, are hydrogen; C$_1$-C$_6$ alkyl; phenyl; benzyl; pyridinyl; C$_1$-C$_6$ alkyl which is substituted by pyridine or

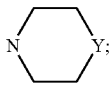

carbonyl which is substituted by C$_1$-C$_6$ alkyl, phenyl, benzyl, pyridine or

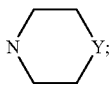

C$_1$-C$_6$ alkanesulfonyl; C$_1$-C$_6$ alkyl which is substituted by hydroxy or C$_1$-C$_6$ alkoxy; or acetyl which is substituted by hydroxy or C$_1$-C$_6$ alkoxy;

Y is oxygen; sulfur; NR$_6$; or CH$_2$;

X$_1$ and X$_3$, each independently, are oxygen; sulfur; NH; N—C$_1$-C$_6$ alkyl; N—C$_3$-C$_6$ cycloalkyl; N-benzyl; or N-phenyl;

X$_2$ is C$_3$-C$_7$ alkylene.

2. The compound according to claim 1, wherein

R$_1$ is C$_3$-C$_6$ cycloalkyl; phenyl; pyridinyl; guanidino; NR$_6$R$_7$; CH$_2$NR$_6$R$_7$; or

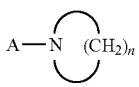

wherein A is C$_1$-C$_6$ alkyl and n is an integer of 2 to 6;

R$_2$ is hydrogen; C$_1$-C$_6$ alkyl; C$_3$-C$_6$ cycloalkyl; benzyl; C$_1$-C$_6$ alkyl which is substituted by hydroxyl, methoxy, halogen or C$_3$-C$_6$ cycloalkyl; or C$_2$-C$_6$ alkenyl;

R$_3$ and R$_4$, each independently, are hydrogen; halogen; hydroxy; C$_3$-C$_6$ cycloalkylamino; C$_1$-C$_6$ alkoxy; C$_1$-C$_6$ alkanoyloxy; C$_3$-C$_6$ cycloalkyloxy which is substituted by carboxy, esterified carboxy or amidated carboxy; or aminooxy;

R$_5$ is hydrogen or hydroxy;

R$_6$ and R$_7$, each independently, are hydrogen; C$_1$-C$_6$ alkyl; benzyl; pyridinyl; C$_1$-C$_6$ alkyl which is substituted by pyridine or

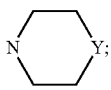

carbonyl which is substituted by pyridine or C$_1$-C$_6$ alkyl; C$_1$-C$_6$ alkanesulfonyl; C$_1$-C$_6$ alkyl which is substituted by hydroxy or C$_1$-C$_6$ alkoxy; or acetyl which is substituted by hydroxy or C$_1$-C$_6$ alkoxy;

Y is oxygen; sulfur; NR$_6$; or CH$_2$;

X$_1$ and X$_3$, each independently, are oxygen; sulfur; NH; or N—C$_1$-C$_6$ alkyl;

X$_2$ is C$_3$-C$_7$ alkylene; or pharmaceutically acceptable salts thereof.

3. The compound according to claim 2, wherein

R$_1$ is cyclopentyl; cyclohexyl; phenyl; isobutylamide; guanidine; 1-propyl-piperidino; NR$_6$R$_7$; CH$_2$NR$_6$R$_7$;

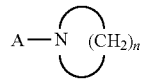

wherein A is C$_1$-C$_6$ alkyl and n is an integer of 2 to 6; or pyridinyl;

R$_2$ is hydrogen; methyl; ethyl; isopropyl; propyl; butyl; isobutyl; methoxymethyl; hydroxymethyl; 2-methylpropyl; pentyl; chloromethyl; chloroethyl; cyclopentyl; cyclopentylmethyl; cyclohexyl; benzyl; or vinyl;

R$_3$ and R$_4$, each independently, are hydrogen; halogen; hydroxy; cyclohexylamino; methoxy; or C$_1$-C$_4$ alkanoyloxy;

R$_5$ is hydrogen or hydroxy;

R$_6$ and R$_7$, each independently, are hydrogen; methyl; ethyl; propyl; benzyl; pyridin-3-yl; pyridin-4-yl; 2-morpholinoethyl; 4-pyridinylcarbonyl; 3-pyridinylcarbonyl; isobutylcarbonyl; ethanesulfonyl; methoxyethyl; hydroxyethyl; hydroxyacetyl; or methoxyacetyl;

Y is oxygen; sulfur; NR$_6$; or CH$_2$;

X$_1$ and X$_3$, each independently, are oxygen; sulfur; amine; or methylamine;

X$_2$ is propylene; butylene; pentylene; hexylene; or heptylene; or pharmaceutically acceptable salts thereof.

4. The compound according to claim 3, wherein

R$_1$ is cyclohexyl; phenyl; pyridinyl; NR$_6$R$_7$; CH$_2$NR$_6$R$_7$; or

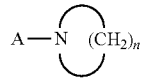

wherein A is C$_1$-C$_2$ alkyl and n is an integer of 4 to 5;

R$_2$ is hydrogen; methyl; ethyl; isopropyl; isobutyl; methoxymethyl; hydroxymethyl; chloromethyl; chloroethyl; cyclopentyl; cyclopentylmethyl; or vinyl;

R$_3$ and R$_4$, each independently, are hydrogen; halogen; hydroxy; or methoxy;

R$_5$ is hydrogen or hydroxy;

R$_6$ and R$_7$, each independently, are hydrogen; methyl; ethyl; benzyl; pyridin-3-yl; pyridin-4-yl; 2-morpholinoethyl; 4-pyridinylcarbonyl; -pyridinylcarbonyl; isobutylcarbonyl; ethanesulfonyl; hydroxyethyl; or methoxyethyl;

Y is oxygen; sulfur; or methylamine;

X$_1$ and X$_3$, each independently, are oxygen; sulfur; amino; or methylamine;

X$_2$ is propylene; butylene; pentylene; or hexylene; or pharmaceutically acceptable salts thereof.

5. The compound according to claim 1, wherein pharmaceutically acceptable salt is hydrogen chloride salt or methanesulfonic acid salt.

6. Benzamidine derivative selected from the group consisting of

1) N-hydroxy-4-(5-[4-(2-isopropyl-5-methyl-1,3-thiazol-4-yl)phenoxy]pentoxy)-benzamidine,
2) 4-(5-[4-(2-isopropyl-5-methyl-1,3-thiazol-4-yl)phenoxy]pentoxy)-benzamidine,
3) N-hydroxy-4-(5-[4-(2-methyl-1,3-thiazol-4-yl)phenoxy]pentoxy)-benzamidine,
4) N-hydroxy-4-(5-[4-(2-ethyl-1,3-thiazol-4-yl)phenoxy]pentoxy)-benzamidine,
5) N-hydroxy-4-(5-[4-(2-isopropyl-1,3-thiazol-4-yl)phenoxy]pentoxy)-benzamidine,
6) N-hydroxy-4-(5-[4-(2-phenyl-1,3-thiazol-4-yl)phenoxy]pentoxy)-benzamidine,
7) N-hydroxy-4-(5-[4-(2-pyridin-3-yl-1,3-thiazol-4-yl)phenoxy]pentoxy)-benzamidine,
8) N-hydroxy-4-(5-[4-(2-cyclohexyl-1,3-thiazol-4-yl)phenoxy]pentoxy)-benzamidine,
9) N-hydroxy-4-(5-[4-(2-pentyl-1,3-thiazol-4-yl)phenoxy]pentoxy)-benzamidine,
10) N-hydroxy-4-(5-[4-(2-ethyl-5-methyl-1,3-thiazol-4-yl)phenoxy]pentoxy)-benzamidine,
11) N-hydroxy-4-(5-[4-(5-methyl-2-phenyl-1,3-thiazol-4-yl)phenoxy]pentoxy)-benzamidine,
12) N-hydroxy-4-(5-[4-(5-methyl-2-pyridin-3-yl-1,3-thiazol-4-yl)phenoxy]pentoxy)-benzamidine,
13) N-hydroxy-4-(5-[4-(2-cyclohexyl-5-methyl-1,3-thiazol-4-yl)phenoxy]pentoxy)-benzamidine,
14) N-hydroxy-4-(5-[4-(5-methyl-2-pentyl-1,3-thiazol-4-yl)phenoxy]pentoxy)-benzamidine,
15) N-hydroxy-4-(5-[4-(2-t-butyl-5-methyl-1,3-thiazol-4-yl)phenoxy]pentoxy)-benzamidine,
16) N-hydroxy-4-(5-[4-(5-ethyl-2-methyl-1,3-thiazol-4-yl)phenoxy]pentoxy)-benzamidine,
17) N-hydroxy-4-(5-[4-(2,5-diethyl-1,3-thiazol-4-yl)phenoxy]pentoxy)-benzamidine,
18) N-hydroxy-4-(5-[4-(5-ethyl-2-isopropyl-1,3-thiazol-4-yl)phenoxy]pentoxy)-benzamidine,
19) N-hydroxy-4-(5-[4-(5-ethyl-2-phenyl-1,3-thiazol-4-yl)phenoxy]pentoxy)-benzamidine,
20) N-hydroxy-4-(5-[4-(5-ethyl-2-pyridin-3-yl-1,3-thiazol-4-yl)phenoxy]pentoxy)-benzamidine,
21) N-hydroxy-4-(5-[4-(2-cyclohexyl-5-ethyl-1,3-thiazol-4-yl)phenoxy]pentoxy)-benzamidine,
22) N-hydroxy-4-(5-[4-(5-ethyl-2-pentyl-1,3-thiazol-4-yl)phenoxy]pentoxy)-benzamidine,
23) N-hydroxy-4-(5-[4-(2-ethyl-5-isopropyl-1,3-thiazol-4-yl)phenoxy]pentoxy)-benzamidine,
24) N-hydroxy-4-(5-[4-(2,5-diisopropyl-1,3-thiazol-4-yl)phenoxy]pentoxy)-benzamidine,
25) N-hydroxy-4-(5-[4-(5-isopropyl-2-phenyl-1,3-thiazol-4-yl)phenoxy]pentoxy)-benzamidine,
26) N-hydroxy-4-(5-[4-(5-isopropyl-2-pyridin-3-yl-1,3-thiazol-4-yl) phenoxy]pentoxy)-benzamidine,
27) N-hydroxy-4-(5-[4-(5-isopropyl-2-pentyl-1,3-thiazol-4-yl)phenoxy]pentoxy)-benzamidine,
28) N-hydroxy-4-(5-[4-(2-methyl-5-propyl-1,3-thiazol-4-yl)phenoxy]pentoxy)-benzamidine,
29) N-hydroxy-4-(5-[4-(5-butyl-2-methyl-1,3-thiazol-4-yl)phenoxy]pentoxy)-benzamidine,
30) N-hydroxy-4-(5-[4-(5-butyl-2-ethyl-1,3-thiazol-4-yl)phenoxy]pentoxy)-benzamidine,
31) N-hydroxy-4-(5-[4-(5-butyl-2-isopropyl-1,3-thiazol-4-yl)phenoxy]pentoxy)-benzamidine,
32) N-hydroxy-4-(5-[4-(5-butyl-2-phenyl-1,3-thiazol-4-yl)phenoxy]pentoxy)-benzamidine,
33) N-hydroxy-4-(5-[4-(5-butyl-2-pyridin-3-yl-1,3-thiazol-4-yl)phenoxy]pentoxy)-benzamidine,
34) N-hydroxy-4-(5-[4-(5-butyl-2-cyclohexyl-1,3-thiazol-4-yl)phenoxy]pentoxy)-benzamidine,
35) N-hydroxy-4-(5-[4-(5-butyl-2-pentyl-1,3-thiazol-4-yl)phenoxy]pentoxy)-benzamidine,
36) N-hydroxy-4-(5-[4-(5-butyl-2-t-butyl-1,3-thiazol-4-yl)phenoxy]pentoxy)-benzamidine,
37) N-hydroxy-4-(5-[4-(5-benzyl-2-methyl-1,3-thiazol-4-yl)phenoxy]pentoxy)-benzamidine,
38) N-hydroxy-4-(5-[4-(5-benzyl-2-isopropyl-1,3-thiazol-4-yl)phenoxy]pentoxy)-benzamidine,
39) N-hydroxy-4-(5-[4-(5-benzyl-2-phenyl-1,3-thiazol-4-yl)phenoxy]pentoxy)-benzamidine,
40) N-hydroxy-4-(5-[4-(5-benzyl-2-pyridin-3-yl-1,3-thiazol-4-yl)phenoxy]pentoxy)-benzamidine,
41) N-hydroxy-4-(5-[4-(5-(2-chloro-ethyl)-2-methyl-1,3-thiazol-4-yl)phenoxy]pentoxy)-benzamidine,
42) N-hydroxy-4-(5-[4-(5-cyclopentyl-2-methyl-1,3-thiazol-4-yl)phenoxy]pentoxy)-benzamidine,
43) N-hydroxy-4-(5-[4-(5-isobutyl-2-methyl-1,3-thiazol-4-yl)phenoxy]pentoxy)-benzamidine,
44) N-hydroxy-4-(5-[4-(5-cyclopentylmethyl-2-methyl-1,3-thiazol-4-yl)phenoxy]pentoxy)-benzamidine,
45) N-hydroxy-4-(5-[4-(5-cyclopentylmethyl-2-ethyl-1,3-thiazol-4-yl)phenoxy]pentoxy)-benzamidine,
46) N-hydroxy-4-(5-[4-(5-cyclopentylmethyl-2-isopropyl-1,3-thiazol-4-yl)phenoxy]pentoxy)-benzamidine,
47) N-hydroxy-4-(5-[4-(5-cyclopentylmethyl-2-phenyl-1,3-thiazol-4-yl)phenoxy]pentoxy)-benzamidine,
48) N-hydroxy-4-(5-[4-(5-cyclopentylmethyl-2-pyridin-3-yl-1,3-thiazol-4-yl)phenoxy]pentoxy)-benzamidine,
49) N-hydroxy-4-(5-[4-(5-cyclopentylmethyl-2-cyclohexyl-1,3-thiazol-4-yl)phenoxy]pentoxy)-benzamidine,
50) N-hydroxy-4-(5-[4-(5-cyclopentylmethyl-2-pentyl-1,3-thiazol-4-yl)phenoxy]pentoxy)-benzamidine,
51) 4-(5-[4-(2-methyl-1,3-thiazol-4-yl)phenoxy]pentoxy)-benzamidine,
52) 4-(5-[4-(2-isopropyl-1,3-thiazol-4-yl)phenoxy]pentoxy)-benzamidine,
53) 4-(5-[4-(2,5-dimethyl-1,3-thiazol-4-yl)phenoxy]pentoxy)-benzamidine,
54) 4-(5-[4-(5-ethyl-2-isopropyl-1,3-thiazol-4-yl)phenoxy]pentoxy)-benzamidine,
55) 4-(5-[4-(5-ethyl-2-phenyl-1,3-thiazol-4-yl)phenoxy]pentoxy)-benzamidine,
56) N-hydroxy-4-(5-[4-(2-amino-1,3-thiazol-4-yl)phenoxy]pentoxy)-benzamidine,
57) N-hydroxy-4-(5-[4-(2-amino-5-methyl-1,3-thiazol-4-yl)phenoxy]pentoxy)-benzamidine,
58) N-hydroxy-4-(5-[4-(2-guanidino-5-methyl-1,3-thiazol-4-yl)phenoxy]pentoxy)-benzamidine,
59) N-hydroxy-4-(5-[4-(2-amino-5-ethyl-1,3-thiazol-4-yl)phenoxy]pentoxy)-benzamidine,
60) N-hydroxy-4-(5-[4-(2-amino-5-isopropyl-1,3-thiazol-4-yl)phenoxy]pentoxy)-benzamidine,
61) N-hydroxy-4-(5-[4-(2-guanidino-5-isopropyl-1,3-thiazol-4-yl)phenoxy]pentoxy)-benzamidine,
62) N-hydroxy-4-(5-[4-(2-amino-5-butyl-1,3-thiazol-4-yl)phenoxy]pentoxy)-benzamidine,
63) N-hydroxy-4-(5-[4-(5-butyl-2-guanidino-1,3-thiazol-4-yl)phenoxy]pentoxy)-benzamidine,
64) N-hydroxy-4-(5-[4-(2-amino-5-benzyl-1,3-thiazol-4-yl)phenoxy]pentoxy)-benzamidine,
65) N-hydroxy-4-(5-[4-(5-benzyl-2-guanidino-1,3-thiazol-4-yl)phenoxy]pentoxy)-benzamidine,
66) N-hydroxy-4-(5-[4-(2-amino-5-cyclopentylmethyl-1,3-thiazol-4-yl)phenoxy]pentoxy)-benzamidine, 67) N-hydroxy-4-(5-[4-(5-cyclopentylmethyl-2-(1-propyl-piperidin-4-yl)-1,3-thiazol-4-yl)phenoxy]pentoxy)-benzamidine,
68) N-hydroxy-4-(5-[4-(2-(isobutyryl)amino-5-methyl-1,3-thiazol-4-yl)phenoxy]pentoxy)-benzamidine,
69) N-hydroxy-4-(5-[4-(5-isopropyl-2-morpholinomethyl-1,3-thiazol-4-yl)phenoxy]pentoxy)-benzamidine,
70) N-hydroxy-4-(5-[4-(2-aminomethyl-5-benzyl-1,3-thiazol-4-yl)phenoxy]pentoxy)-benzamidine,
71) N-hydroxy-4-(5-[4-(5-methyl-2-(1-propyl-piperidin-4-yl)-1,3-thiazol-4-yl)phenoxy]pentoxy)-benzamidine,
72) N-hydroxy-4-(5-[4-(5-isopropyl-2-aminomethyl-1,3-thiazol-4-yl)phenoxy]pentoxy)-benzamidine,
73) N-hydroxy-4-(5-[4-(5-vinyl-2-methyl-1,3-thiazol-4-yl)phenoxy]pentoxy)-benzamidine,
74) N-hydroxy-4-(5-[4-(5-hydroxymethyl-2-methyl-1,3-thiazol-4-yl)phenoxy]pentoxy)-benzamidine,
75) N-hydroxy-4-(5-[4-(5-methoxymethyl-2-methyl-1,3-thiazol-4-yl)phenoxy]pentoxy)-benzamidine,
76) N-hydroxy-4-(5-[4-(5-(2-chloroethyl)-2-amino-1,3-thiazol-4-yl)phenoxy]pentoxy)-benzamidine,
77) N-hydroxy-4-(5-[4-(5-vinyl-2-amino-1,3-thiazol-4-yl)phenoxy]pentoxy)-benzamidine,
78) N-hydroxy-4-(5-[4-(5-vinyl-2-(pyridin-3-yl)-1,3-thiazol-4-yl)phenoxy]pentoxy)-benzamidine,
79) N-hydroxy-4-(5-[4-(5-(2-chloroethyl)-2-(pyridin-3-yl)-1,3-thiazol-4-yl)phenoxy]pentoxy)-benzamidine,
80) N-hydroxy-4-(5-[4-(2-amino-5-cyclopentyl-1,3-thiazol-4-yl)phenoxy]pentoxy)-benzamidine,
81) N-hydroxy-4-(5-[4-(5-ethyl-2-aminomethyl-1,3-thiazol-4-yl)phenoxy]pentoxy)-benzamidine,
82) N-hydroxy-4-(5-[4-(5-isopropyl-2-(piperidin-3-O-1,3-thiazol-4-yl)phenoxy]pentoxy)-benzamidine,
83) N-hydroxy-4-(5-[4-(2-ethylamino-1,3-thiazol-4-yl)phenoxy]pentoxy)-benzamidine,
84) N-hydroxy-4-(5-[4-(2-ethanesulfonylamino-1,3-thiazol-4-yl)phenoxy]pentoxy)-benzamidine,
85) N-hydroxy-4-(5-[4-(5-methyl-2-methylamino-1,3-thiazol-4-yl)phenoxy]pentoxy)-benzamidine,
86) N-hydroxy-4-(5-[4-(2-ethylamino-5-methyl-1,3-thiazol-4-yl)phenoxy]pentoxy)-benzamidine,
87) N-hydroxy-4-(5-[4-(5-methyl-2-propylamino-1,3-thiazol-4-yl)phenoxy]pentoxy)-benzamidine,
88) N-hydroxy-4-(5-[4-(5-cyclopentylmethyl-2-(3-pyridylcarbonyl)amino-1,3-thiazol-4-yl)phenoxy]pentoxy)-benzamidine,
89) N-hydroxy-4-(5-[4-(2-hydroxyacetylamino-5-methyl-1,3-thiazol-4-yl)phenoxy]pentoxy)-benzamidine,
90) N-hydroxy-4-(5-[4-(5-methyl-2-(4-pyridylcarbonyl)amino-1,3-thiazol-4-yl)phenoxy]pentoxy)-benzamidine,
91) N-hydroxy-4-(5-[4-(5-methyl-2-(3-pyridylcarbonyl)amino-1,3-thiazol-4-yl)phenoxy]pentoxy)-benzamidine,
92) N-hydroxy-4-(5-[4-(2-ethanesulfonylamino-5-methyl-1,3-thiazol-4-yl)phenoxy]pentoxy)-benzamidine,
93) N-hydroxy-4-(5-[4-(2-(2-methoxyethyl)amino-5-methyl-1,3-thiazol-4-yl)phenoxy]pentoxy)-benzamidine,
94) N-hydroxy-4-(5-[4-(2-ethanesulfonylamino-5-ethyl-1,3-thiazol-4-yl)phenoxy]pentoxy)-benzamidine,
95) N-hydroxy-4-(5-[4-(5-ethyl-2-methylamino-1,3-thiazol-4-yl)phenoxy]pentoxy)-benzamidine,
96) N-hydroxy-4-(5-[4-(5-ethyl-2-ethylamino-1,3-thiazol-4-yl)phenoxy]pentoxy)-benzamidine,
97) N-hydroxy-4-(5-[4-(5-ethyl-2-propylamino-1,3-thiazol-4-yl)phenoxy]pentoxy)-benzamidine,
98) N-hydroxy-4-(5-[4-(5-ethyl-2-methoxyacetylamino-1,3-thiazol-4-yl)phenoxy]pentoxy)-benzamidine,
99) N-hydroxy-4-(5-[4-(5-ethyl-2-(4-pyridylcarbonyl)amino-1,3-thiazol-4-yl)phenoxy]pentoxy)-benzamidine,
100) N-hydroxy-4-(5-[4-(5-ethyl-2-(3-pyridylcarbonyl)amino-1,3-thiazol-4-yl)phenoxy]pentoxy)-benzamidine,
101) N-hydroxy-4-(5-[4-(5-ethyl-2-(2-methoxyethyl)amino-1,3-thiazol-4-yl)phenoxy]pentoxy)-benzamidine,
102) N-hydroxy-4-(5-[4-(5-isopropyl-2-methylamino-1,3-thiazol-4-yl)phenoxy]pentoxy)-benzamidine,
103) N-hydroxy-4-(5-[4-(2-ethylamino-5-isopropyl-1,3-thiazol-4-yl) phenoxy]pentoxy)-benzamidine,
104) N-hydroxy-4-(5-[4-(5-butyl-2-methylamino-1,3-thiazol-4-yl)phenoxy]pentoxy)-benzamidine,
105) N-hydroxy-4-(5-[4-(5-butyl-2-ethylamino-1,3-thiazol-4-yl)phenoxy]pentoxy)-benzamidine,
106) N-hydroxy-4-(5-[4-(5-benzyl-2-methylamino-1,3-thiazol-4-yl)phenoxy]pentoxy)-benzamidine,
107) N-hydroxy-4-(5-[4-(5-benzyl-2-ethylamino-1,3-thiazol-4-yl)phenoxy]pentoxy)-benzamidine,
108) N-hydroxy-4-(5-[4-(5-cyclopentylmethyl-2-methylamino-1,3-thiazol-4-yl)phenoxy]pentoxy)-benzamidine,
109) N-hydroxy-4-(5-[4-(5-cyclopentylmethyl-2-ethylamino-1,3-thiazol-4-yl)phenoxy]pentoxy)-benzamidine,
110) N-hydroxy-4-(5-[4-(5-cyclopentylmethyl-2-propylamino-1,3-thiazol-4-yl)phenoxy]pentoxy)-benzamidine,
111) N-hydroxy-4-(5-[4-(5-cyclopentylmethyl-2-(4-pyridylcarbonyl)amino-1,3-thiazol-4-yl)phenoxy]pentoxy)-benzamidine,
112) N-hydroxy-4-(5-[4-(5-cyclopentyl-2-propylamino-1,3-thiazol-4-yl)phenoxy]pentoxy)-benzamidine,
113) N-hydroxy-4-(5-[4-(5-isopropyl-2-[(pyridin-3-ylmethyl)amino]-1,3-thiazol-4-yl)phenoxy]pentoxy)-benzamidine,
114) N-hydroxy-4-(5-[4-(5-(2-chloroethyl)-2-methylamino-1,3-thiazol-4-yl)phenoxy]pentoxy)-benzamidine,
115) N-hydroxy-4-(5-[4-(2-methylamino-1,3-thiazol-4-yl)phenoxy]pentoxy)-benzamidine,
116) N-hydroxy-4-(5-[4-(5-ethyl-2-[(pyridin-3-yl-methyl)amino-1,3-thiazol-4-yl)phenoxy]pentoxy)-benzamidine,
117) N-hydroxy-4-(5-[4-(2-(ethanesulfonyl-methyl-amino)-1,3-thiazol-4-yl)phenoxy]pentoxy)-benzamidine,
118) N-hydroxy-4-(5-[4-(2-methyl-(2-morpholinoethyl)amino-1,3-thiazol-4-yl) phenoxy]pentoxy)-benzamidine,
119) N-hydroxy-4-(5-[4-(2-(2-hydroxyethyl)-methyl-amino-5-methyl-1,3-thiazol-4-yl)phenoxy]pentoxy)-benzamidine,
120) N-hydroxy-4-(5-[4-(2-(ethyl-(2-hydroxyethyl)-amino)-5-methyl-1,3-thiazol-4-yl)phenoxy]pentoxy)-benzamidine,
121) N-hydroxy-4-(5-[4-(2-(bis-(2-methoxyethyl)-amino)-5-methyl-1,3-thiazol-4-yl)phenoxy]pentoxy)-benzamidine,
122) N-hydroxy-4-(5-[4-(5-methyl-2-(methyl-(2-morpholinoethyl)-amino)-1,3-thiazol-4-yl)phenoxy]pentoxy)-benzamidine, 123) N-hydroxy-4-(5-[4-(2-(ethyl-1-(2-morpholinoethyl)-amino)-5-methyl-1,3-thiazol-4-yl)phenoxy]pentoxy)-benzamidine,
124) N-hydroxy-4-(5-[4-(2-(benzyl-methyl-amino)-5-methyl-1,3-thiazol-4-yl)phenoxy]pentoxy)-benzamidine,
125) N-hydroxy-4-(5-[4-(5-methyl-2-(methyl-pyridin-3-yl-methyl-amino)-1,3-thiazol-4-yl)phenoxy]pentoxy)-benzamidine,
126) N-hydroxy-4-(5-[4-(2-(benzyl-ethyl-amino)-5-methyl-1,3-thiazol-4-yl)phenoxy]pentoxy)-benzamidine,
127) N-hydroxy-4-(5-[4-(2-(bis-(2-hydroxyethyl)-amino)-5-methyl-1,3-thiazol-4-yl)phenoxy]pentoxy)-benzamidine,
128) N-hydroxy-4-(5-[4-(5-ethyl-2-((2-hydroxyethyl)-methyl-amino)-1,3-thiazol-4-yl)phenoxy]pentoxy)-benzamidine,
129) N-hydroxy-4-(5-[4-(5-ethyl-2-(ethyl-(2-hydroxyethyl)-amino)-1,3-thiazol-4-yl)phenoxy]pentoxy)-benzamidine,
130) N-hydroxy-4-(5-[4-(5-ethyl-2-(methyl-(2-morpholinoethyl)-amino)-1,3-thiazol-4-yl)phenoxy]pentoxy)-benzamidine,
131) N-hydroxy-4-(5-[4-(5-ethyl-2-(ethyl-(2-morpholinoethyl)-am no)-1,3-thiazol-4-yl)phenoxy]pentoxy)-benzamidine,
132) N-hydroxy-4-(5-[4-(2-(benzyl-methyl-amino)-5-ethyl-1,3-thiazol-4-yl)phenoxy]pentoxy)-benzamidine,
133) N-hydroxy-4-(5-[4-(5-ethyl-2-(methyl-(pyridin-3-yl-methyl)amino)-1,3-thiazol-4-yl)phenoxy]pentoxy)-benzamidine,
134) N-hydroxy-4-(5-[4-(2-(benzyl-ethyl-amino)-5-ethyl-1,3-thiazol-4-yl)phenoxy]pentoxy)-benzamidine,
135) N-hydroxy-4-(5-[4-(5-ethyl-2-(ethyl-(pyridin-3-yl-methyl)amino)-1,3-thiazol-4-yl)phenoxy]pentoxy)-benzamidine,
136) N-hydroxy-4-(5-[4-(2-(bis-(pyridin-3-yl-methyl)amino)-5-ethyl-1,3-thiazol-4-yl)phenoxy]pentoxy)-benzamidine,
137) N-hydroxy-4-(5-[4-(2-dipropylamino-5-ethyl-1,3-thiazol-4-yl)phenoxy]pentoxy)-benzamidine,
138) N-hydroxy-4-(5-[4-(2-(bis-(2-hydroxyethyl)amino)-5-ethyl-1,3-thiazol-4-yl)phenoxy]pentoxy)-benzamidine,
139) N-hydroxy-4-(5-[4-(2-((2-hydroxyethyl)-methyl-amino)-5-isopropyl-1,3-thiazol-4-yl)phenoxy]pentoxy)-benzamidine,
140) N-hydroxy-4-(5-[4-(5-isopropyl-2-(methyl-(pyridin-3-yl-methyl)amino)-1,3-thiazol-4-yl)phenoxy]pentoxy)-benzamidine,
141) N-hydroxy-4-(5-[4-(2-(ethanesulfonyl-methyl-amino)-5-isopropyl-1,3-thiazol-4-yl)phenoxy]pentoxy)-benzamidine,
142) N-hydroxy-4-(5-[4-(5-butyl-2-((2-hydroxyethyl)-methyl-amino)-1,3-thiazol-4-yl)phenoxy]pentoxy)-benzamidine,
143) N-hydroxy-4-(5-[4-(5-butyl-2-(methyl-(2-morpholinoethyl)amino)-1,3-thiazol-4-yl)phenoxy]pentoxy)-benzamidine,
144) N-hydroxy-4-(5-[4-(5-butyl-2-(methyl-(pyridin-3-yl-methyl)amino)-1,3-thiazol-4-yl)phenoxy]pentoxy)-benzamidine,
145) N-hydroxy-4-(5-[4-(5-butyl-2-dipropylamino-1,3-thiazol-4-yl)phenoxy]pentoxy)-benzamidine,
146) N-hydroxy-4-(5-[4-(5-cyclopentylmethyl-2-(methyl-(pyridin-3-yl-methyl)amino)-1,3-thiazol-4-yl)phenoxy]pentoxy)-benzamidine,
147) N-hydroxy-4-(5-[4-(5-cyclopentylmethyl-2-(methyl-(2-morpholinoethyl)amino)-1,3-thiazol-4-yl)phenoxy]pentoxy)-benzamidine,
148) N-hydroxy-4-(5-[4-(5-cyclopentylmethyl-2-dipropylamino-1,3-thiazol-4-yl)phenoxy]pentoxy)-benzamidine,
149) N-hydroxy-4-(5-[4-(5-butyl-2-diethylamino-1,3-thiazol-4-yl)phenoxy]pentoxy)-benzamidine,
150) N-hydroxy-4-(5-[4-(5-butyl-2-ethylmethylamino-1,3-thiazol-4-yl)phenoxy]pentoxy)-benzamidine,
151) N-hydroxy-4-(5-[4-(5-butyl-2-dimethylamino-1,3-thiazol-4-yl)phenoxy]pentoxy)-benzamidine,
152) N-hydroxy-4-(5-[4-(5-cyclopentyl-2-[methyl-(2-morpholinoethyl)amino]-1,3-thiazol-4-yl)phenoxy]pentoxy)-benzamidine,
153) N-hydroxy-4-(5-[4-(5-isobutyl-2-[methyl-(2-morpholinoethyl)amino]-1,3-thiazol-4-yl)phenoxy]pentoxy)-benzamidine,
154) N-hydroxy-4-(5-[4-(5-(2-chloroethyl)-2-dimethylamino-1,3-thiazol-4-yl)phenoxy]pentoxy)-benzamidine,
155) N-hydroxy-4-(5-[4-(5-cyclopentyl-2-diethylamino-1,3-thiazol-4-yl)phenoxy]pentoxy)-benzamidine,
156) N-hydroxy-4-(5-[4-(5-isopropyl-2-dipropylamino-1,3-thiazol-4-yl)phenoxy]pentoxy)-benzamidine,
157) N-hydroxy-4-(5-[4-(5-ethyl-diethylamino-1,3-thiazol-4-yl)phenoxy]pentoxy)-benzamidine,
158) N-hydroxy-4-(5-[4-(5-isopropyl-2-dimethyl-(2-morpholinoethyl)amino]-1,3-thiazol-4-yl)phenoxy]pentoxy)-benzamidine,
159) N-hydroxy-4-(5-[4-(5-cyclopentylmethyl-2-diethylamino-1,3-thiazol-4-yl)phenoxy]pentoxy)-benzamidine,
160) N-hydroxy-4-(5-[4-(5-isopropyl-2-dimethylamino-1,3-thiazol-4-yl)phenoxy]pentoxy)-benzamidine,
161) N-hydroxy-4-(5-[4-(5-isopropyl-2-diethylamino-1,3-thiazol-4-yl)phenoxy]pentoxy)-benzamidine,
162) N-hydroxy-4-(5-[4-(5-cyclopentylmethyl-2-dimethylamino-1,3-thiazol-4-yl)phenoxy]pentoxy)-benzamidine,
163) N-hydroxy-4-(5-[4-(5-methyl-2-piperidino-1,3-thiazol-4-yl) phenoxy]pentoxy)-benzamidine,
164) N-hydroxy-4-(5-[4-(5-methyl-2-morpholino-1,3-thiazol-4-yl)phenoxy]pentoxy)-benzamidine,
165) N-hydroxy-4-(5-[4-(5-ethyl-2-piperdino-1,3-thiazol-4-yl)phenoxy]pentoxy)-benzamidine,
166) N-hydroxy-4-(5-[4-(5-cyclopentylmethyl-2-piperdino-1,3-thiazol-4-yl)phenoxy]pentoxy)-benzamidine,
167) N-hydroxy-4-(5-[4-(5-cyclopentylnnethyl-2-morpholino-1,3-thiazol-4-yl)phenoxy]pentoxy)-benzamidine,
168) N-hydroxy-4-(5-[4-(5-isopropyl-2-morpholino-1,3-thiazol-4-yl)phenoxy]pentoxy)-benzamidine,
169) N-hydroxy-4-(5-(4-[5-cyclopentylmethyl-2-(4-methylpiperazino)-1,3-thiazol-4-yl]phenoxy)-pentoxy)-benzamidine,
170) N-hydroxy-4-(5-[4-(5-vinyl-2-morpholin-4-yl-1,3-thiazol-4-yl)phenoxy]pentoxy)-benzamidine,
171) N-hydroxy-4-(5-[4-(5-cyclopentyl-2-morpholin-4-yl-1,3-thiazol-4-yl)phenoxy]pentoxy)-benzamidine,
172) N-hydroxy-4-(5-[4-(5-isobutyl-2-morpholin-4-yl-1,3-thiazol-4-yl)phenoxy]pentoxy)-benzamidine,
173) N-hydroxy-4-(5-(4-[5-ethyl-2-(4-methylpiperazino)-1,3-thiazol-4-yl]phenoxy)-pentoxy)-benzamidine,
174) N-hydroxy-4-(5-[4-(2-morpholin-4-yl-1,3-thiazol-4-yl)phenoxy]pentoxy)-benzamidine, 175) N-hydroxy-4-(5-(4-[5-isopropyl-2-(4-methylpiperazino)-1,3-thiazol-4-yl]phenoxy)-pentoxy)-benzamidine,
176) N-hydroxy-4-(5-[4-(5-isopropyl-2-methyl-1,3-thiazol-4-yl)phenoxy]-pentylamino)-benzamidine,
177) N-hydroxy-4-(2-[2-(4-(5-isopropyl-2-methyl-1,3-thiazol-4-yl)phenoxy)-ethoxy]-ethoxy)-benzamidine,
178) N-hydroxy-4-(3-hydroxy-5-[4-(5-isopropyl-2-methyl-1,3-thiazol-4-yl)-phenoxy]-3-methyl-pentoxy)-benzamidine,
179) N-hydroxy-4-(2-[2-(4-(5-isopropyl-2-methyl-1,3-thiazol-4-yl)-phenoxy)-1-methyl-ethylamino]-ethoxy)-benzamidine,
180) N-hydroxy-4-(3-[4-(3-(4-(5-isopropyl-2-methyl-1,3-thiazol-4-yl)-phenoxy)-propyl)-piperazin-1-yl]-propoxy)-benzamidine,
181) N-hydroxy-4-(5-[4-(5-isopropyl-2-methyl-1,3-thiazol-4-yl)-phenoxy]-pentanoyl-amino)-benzamidine,
182) N-hydroxy-4-(5-[4-(5-isopropyl-2-methyl-1,3-thiazol-4-yl)-phenoxy]-pentyl-methyl-amino)-benzamidine,
183) N-hydroxy-4-(4-[4-(5-isopropyl-2-methyl-1,3-thiazol-4-yl)-phenoxy]-2-butenyloxy)-benzamidine,
184) N-hydroxy-4-(4-[4-(5-isopropyl-2-methyl-1,3-thiazol-4-yl)-phenoxymethyl]-benzyloxy)-benzamidine,
185) N-hydroxy-4-(2-[2-(4-(5-isopropyl-2-methyl-1,3-thiazol-4-yl)phenoxy)-ethylamino]-ethoxy)-benzamidine,
186) N-hydroxy-2-fluoro-4-(5-[4-(5-isopropyl-2-methyl-1,3-thiazol-4-yl)-phenoxy]-pentoxy)-benzamidine,
187) 2,N-dihydroxy-4-(5-[4-(5-isopropyl-2-methyl-1,3-thiazol-4-yl)-phenoxy]-pentoxy)-benzamidine,
188) N-hydroxy-4-(5-[4-(5-isopropyl-2-methyl-1,3-thiazol-4-yl)-phenoxy]-pentoxy-3-methoxy)-benzamidine,
189) N-hydroxy-2-cyclohexylamino-4-(5-[4-(5-isopropyl-2-methyl-1,3-thiazol-4-yl)-phenoxy]-pentoxy)-benzamidine,
190) N-hydroxy-2-fluoro-4-(5-[3-fluoro-4-(5-isopropyl-2-methyl-1,3-thiazol-4-yl)-phenoxy]-pentoxy)-benzamidine,
191) N-hydroxy-4-(3-[4-(5-isopropyl-2-methyl-1,3-thiazol-4-yl)phenoxy]propoxy)-benzamidine,
192) N-hydroxy-3-(5-[4-(5-isopropyl-2-methyl-thiazol-4-yl)-phenoxy]-pentylamino)-benzamidine,
193) N-hydroxy-4-(4-[4-(2-cyclohexyl-5-ethyl-thiazol-4-yl)-phenoxy]-butoxy)-benzamidine,
194) N-hydroxy-4-(3-[4-(5-ethyl-2-[(2-hydroxyethyl)-methyl-amino]-thiazol-4-yl)phenoxy]propoxy)-benzamidine,
195) N-hydroxy-4-(4-[4-(5-ethyl-2-[(2-hydroxyethyl)-methylamino]-thiazol-4-yl)phenoxy]butoxy)-benzamidine,
196) N-hydroxy-4-(3-[4-(5-ethyl-2-[methyl-(pyridin-3-yl-methyl)amino]-thiazol-4-yl)phenoxy]propoxy)-benzamidine,
197) N-hydroxy-4-(4-[4-(5-ethyl-2-[methyl-(pyridin-3-yl-methyl)amino]-thiazol-4-yl)phenoxy]butoxy)-benzamidine,
198) N-hydroxy-4-(4-[4-(5-cyclopentylmethyl-2-isopropyl-thiazol-4-yl)-phenoxymethyl]-benzyloxy)-benzamidine,
199) N-hydroxy-4-(4-[4-(5-butyl-2-isopropyl-thiazol-4-yl)-phenoxymethyl]-benzyloxy)-benzamidine,
200) N-hydroxy-4-(4-[4-(5-cyclopentylmethyl-2-aminothiazol-4-yl)-phenoxymethyl]-benzyloxy)-benzamidine,
201) N-hydroxy-4-(4-[4-(5-cyclopentylmethyl-2-aminothiazol-4-yl)-phenoxymethyl]-benzyloxy-2-fluoro)-benzamidine,
202) N-hydroxy-4-(4-[4-(2-methylamino-thiazol-4-yl)-phenoxymethyl]-benzyloxy)-benzamidine,
203) N-hydroxy-4-(6-[4-(5-isopropyl-2-methyl-thiazol-4-yl)-phenoxymethyl]-pyridin-2-yl-methoxy)-benzamidine,
204) N-hydroxy-4-(2-[4-(5-isopropyl-2-methyl-thiazol-4-yl)-phenoxymethyl]-benzyloxy)-benzamidine,
205) N-hydroxy-4-(4-[4-(5-cyclopentylmethyl-2-cyclohexyl-thiazol-4-yl)-phenoxymethyl]-benzyloxy)-benzamidine,
206) N-hydroxy-4-(6-[4-(5-isopropyl-2-methyl-thiazol-4-yl)phenoxy]-hexyloxy)-benzamidine,
207) N-hydroxy-4-(5-[2-ethyl-5-hydroxy-4-(2-methyl-thiazol-4-yl)phenoxy]-pentyloxy)-benzamidine, and
208) N-hydroxy-4-(5-[2-ethyl-4-(2-methyl-thiazol-4-yl)-5-propoxy-phenoxy]-pentyloxy)-benzamidine; or pharmaceutically acceptable salts thereof.

7. A process for producing a compound of the formula 1a or pharmaceutically acceptable salts thereof which comprises the steps of 1) reacting a compound of the formula 2 with a compound of the formula 3 in the presence of inorganic base to prepare a compound of the formula 4,
2) reacting a compound of the formula 5 with acid chloride of the formula 6 in the presence of inorganic acid to prepare phenone of the formula 7, and reacting the phenone of the formula 7 with acid to prepare a compound of the formula 8,
3) reacting the compound of the formula 4 prepared in step 1) with the compound of the formula 8 prepared in step 2) in the presence of inorganic base to prepare benzonitrile derivatives of the formula 9,
4) reacting the compound of the formula 9 prepared in step 3) with brominating agent to prepare α-brominated compound of the formula 10,
5) reacting α-brominated compound of the formula 10 prepared in step 4) with thioamide compound of the formula 11 to prepare benzonitrile derivatives with thiazole ring of the formula 12, and
6) reacting the compound of the formula 12 prepared in step 5) with amine compound to prepare benzamidine derivatives of the formula 1a,

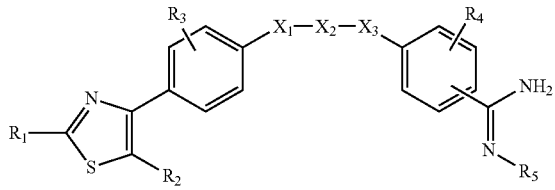

Formula 1a

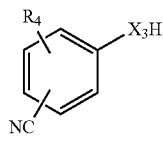

Formula 2

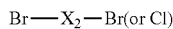

Formula 3

-continued

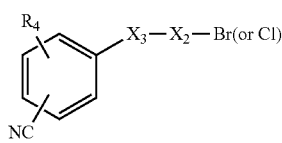
Formula 4

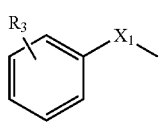
Formula 5

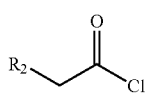
Formula 6

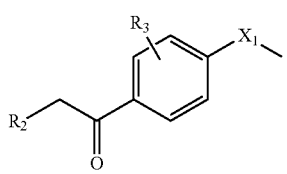
Formula 7

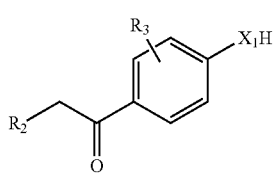
Formula 8

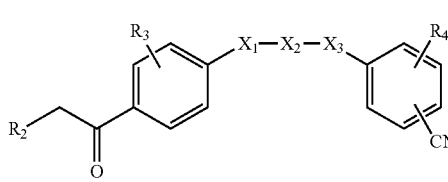
Formula 9

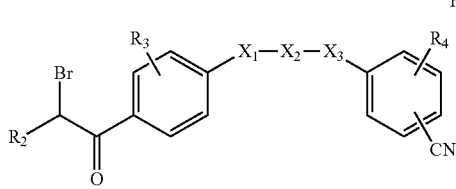
Formula 10

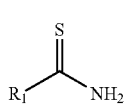
Formula 11

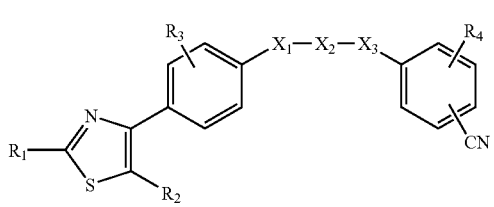
Formula 12 wherein $R_1$ is pyridine-substituted $C_1$-$C_6$ alkyl; $C_3$-$C_6$ cycloalkyl; benzyl; phenyl; amino; guanidino; pyridinyl; $C_1$-$C_6$ alkyl-substituted pyridinyl; or

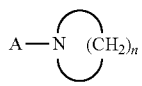

wherein A is $C_1$-$C_6$ alkyl and n is integer of 2 to 6;

$R_2$ is hydrogen; $C_1$-$C_6$ alkyl; $C_3$-$C_6$ cycloalkyl; phenyl; benzyl; $C_1$-$C_6$ alkyl which is substituted by hydroxy, $C_1$-$C_6$ alkoxy, halogen or $C_3$-$C_6$ cycloalkyl; or $C_2$-$C_6$ alkenyl;

$R_3$ and $R_4$, each independently, are hydrogen; halogen; hydroxy; $C_1$-$C_6$ alkyl which is unsubstituted or substituted halogen; $C_3$-$C_6$ cycloalkylamino; $C_1$-$C_6$ alkoxy; $C_1$-$C_6$ alkanoyloxy; $C_2$-$C_6$ alkenyloxy; phenyl-$C_1$-$C_6$ alkoxy; phenoxy; $C_2$-$C_6$ alkenoyloxy; phenyl-$C_1$-$C_6$ alkanoyloxy; $C_3$-$C_6$ cycloalkyloxy which is substituted by carboxy, esterified carboxy or amidated carboxy; or aminooxy;

$R_5$ is hydrogen or hydroxy;

$X_1$ and $X_3$, each independently, are oxygen; sulfur; NH; N—$C_1$-$C_6$ alkyl; N—$C_3$-$C_6$-cycloalkyl; N-benzyl; or N-phenyl;

$X_2$ is $C_3$-$C_7$ alkylene.

8. A process for producing a compound of the formula 1b or pharmaceutically acceptable salts thereof which comprises the steps of 1) reacting a compound of the formula 2 with a compound of the formula 3 in the presence of inorganic base to prepare a compound of the formula 4,
2) reacting a compound of the formula 5 with acid chloride of the formula 6 in the presence of inorganic acid to prepare phenone of the formula 7, and reacting the phenone of the formula 7 with acid to prepare a compound of the formula 8,
3) reacting the compound of the formula 4 prepared in step 1) with the compound of the formula 8 prepared in step 2) in the presence of inorganic base to prepare benzonitrile derivatives of the formula 9,
4) reacting the compound of the formula 9 prepared in step 3) with brominating agent to prepare α-brominated compound of the formula 10,
5) reacting α-brominated compound of the formula 10 prepared in step 4) with thiourea of the formula 13 to prepare benzonitrile derivatives with aminothiazole ring of the formula 14,
6) reacting the compound of the formula 14 prepared in step 5) with halide compound of the formula 15 to prepare benzonitrile derivatives with thiazole ring substituted with primary amine of the formula 16, and
7) reacting the compound of the formula 16 prepared in step 6) with amine compound to prepared benzamidine derivatives of the formula 1b, Formula 1b 1b -continued Formula 2
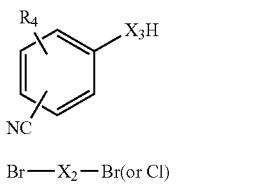

Formula 3
Br—X₂—Br(or Cl)

Formula 4
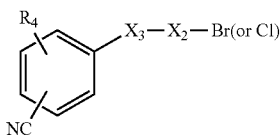

Formula 5
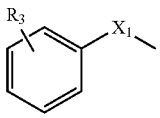

Formula 6
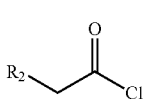

Formula 7
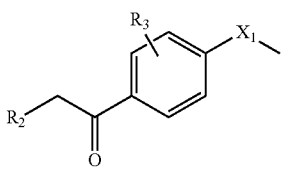

Formula 8
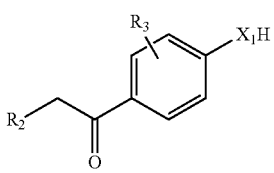

Formula 9
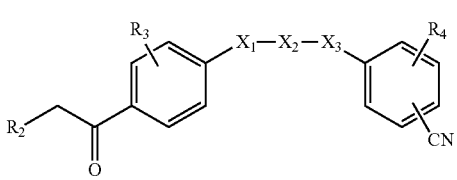

Formula 10
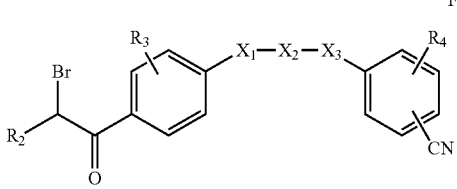

Formula 13
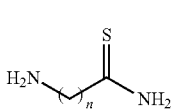

Formula 14
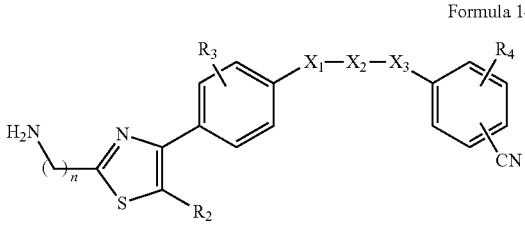

Formula 15
R₆Cl(or Br)

Formula 16
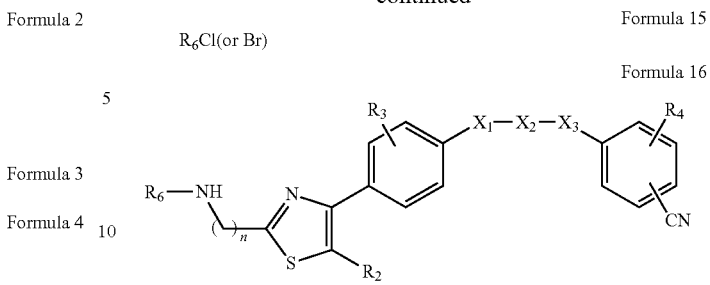

wherein $R_2$ is hydrogen; $C_1$-$C_6$ alkyl; $C_3$-$C_6$ cycloalkyl; phenyl; benzyl; $C_1$-$C_6$ alkyl which is substituted by hydroxy, $C_1$-$C_6$ alkoxy, halogen or $C_3$-$C_6$ cycloalkyl; or $C_2$-$C_6$ alkenyl;

$R_3$ and $R_4$, each independently, are hydrogen; halogen; hydroxy; $C_1$-$C_6$ alkyl which is unsubstituted or substituted halogen; $C_3$-$C_6$ cycloalkylamino; $C_1$-$C_6$ alkoxy; $C_1$-$C_6$ alkanoyloxy; $C_2$-$C_6$ alkenyloxy; phenyl-$C_1$-$C_6$ alkoxy; phenoxy; $C_2$-$C_6$ alkenoyloxy; phenyl-$C_1$-$C_6$ alkanoyloxy; $C_3$-$C_6$ cycloalkyloxy which is substituted by carboxy, esterified carboxy or amidated carboxy; or aminooxy;

$R_5$ is hydrogen or hydroxy;

$R_6$ is hydrogen; $C_1$-$C_6$ alkyl; phenyl; benzyl; pyridinyl; $C_1$-$C_6$ alkyl which is substituted by pyridine or

carbonyl which is substituted by $C_1$-$C_6$ alkyl, phenyl, benzyl, pyridine or

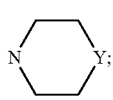

$C_1$-$C_6$ alkanesulfonyl; $C_1$-$C_6$ alkyl which is substituted by hydroxy or $C_1$-$C_6$ alkoxy; or acetyl which is substituted by hydroxy or $C_1$-$C_6$ alkoxy;

$X_1$ and $X_3$, each independently, are oxygen; sulfur; NH; N—$C_1$-$C_6$ alkyl; N—$C_3$-$C_6$ cycloalkyl; N-benzyl; or N-phenyl;

$X_2$ is $C_3$-$C_7$ alkylene;

and n is an integer of 0 to 6, with the proviso that $R_6$ is not hydrogen.

9. A process for producing a compound of the formula 1c or pharmaceutically acceptable salts thereof which comprises the steps of 1) reacting a compound of the formula 2 with a compound of the formula 3 in the presence of inorganic base to prepare a compound of the formula 4, 2) reacting a compound of the formula 5 with acid chloride of the formula 6 in the presence of inorganic acid to prepare phenone of the formula 7, and reacting the phenone of the formula 7 with acid to prepare a compound of the formula 8, 3) reacting the compound of the formula 4 prepared in step 1) with the compound of the formula 8 prepared in step 2) in the presence of inorganic base to prepare benzonitrile derivatives of the formula 9,
4) reacting the compound of the formula 9 prepared in step 3) with brominating agent to prepare α-brominated compound of the formula 10,
5) reacting α-brominated compound of the formula 10 prepared in step 4) with thiourea of the formula 13 to prepare benzonitrile derivatives with aminothiazole ring of the formula 14,
6) reacting the compound of the formula 14 prepared in step 5) with halide compound of the formula 15 to prepare benzonitrile derivatives with thiazole ring substituted with primary amine of the formula 16,
7) reacting the compound of the formula 16 prepared in step 6) above with a compound of the formula 17 to prepare benzonitrile derivatives with thiazole ring substituted with secondary amine of the formula 18, and
8) reacting the compound of the formula 18 prepared in step 7) with amine compound to prepare benzamidine derivatives of the formula 1c,

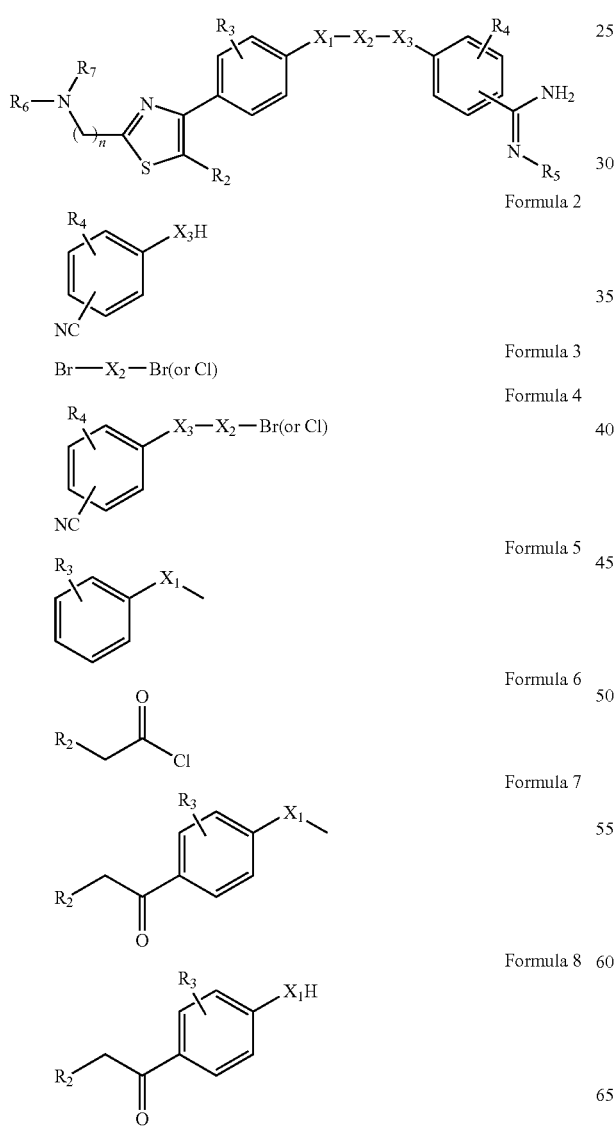

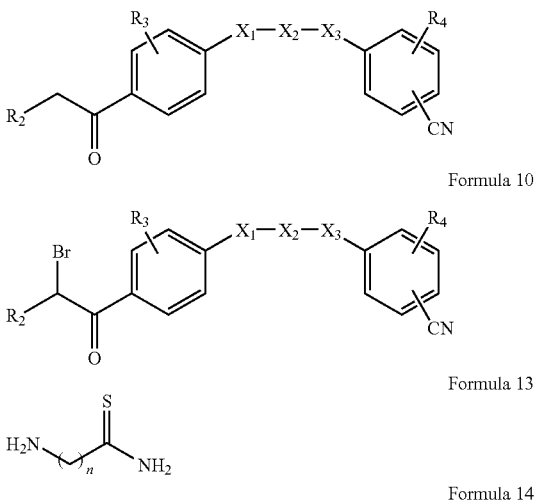

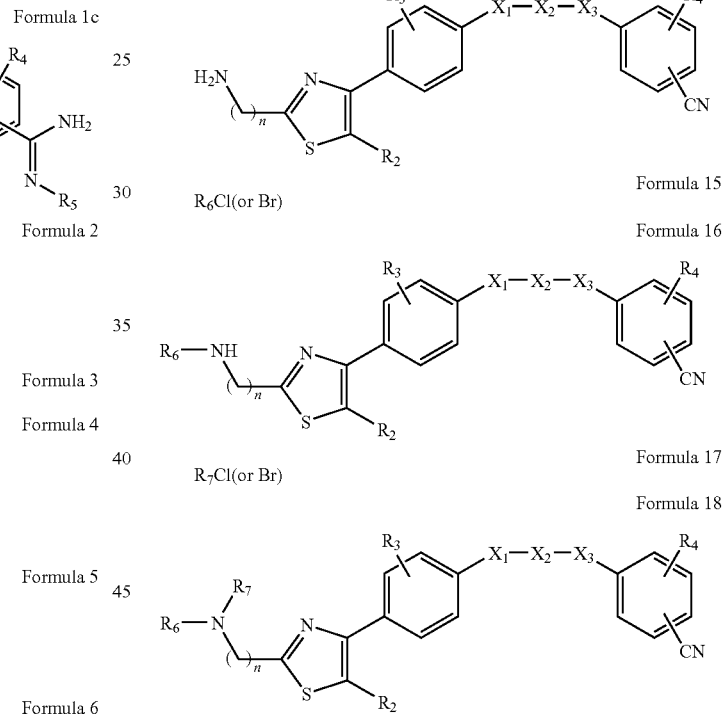

wherein
$R_2$ is hydrogen; $C_1$-$C_6$ alkyl; $C_3$-$C_6$ cycloalkyl; phenyl; benzyl; $C_1$-$C_6$ alkyl which is substituted by hydroxy, $C_1$-$C_6$ alkoxy, halogen or $C_3$-$C_6$ cycloalkyl; or $C_2$-$C_6$ alkenyl;
$R_3$ and $R_4$, each independently, are hydrogen; halogen; hydroxy; $C_1$-$C_6$ alkyl which is unsubstituted or substituted halogen; $C_3$-$C_6$ cycloalkylamino; $C_1$-$C_6$ alkoxy; $C_1$-$C_6$ alkanoyloxy; $C_2$-$C_6$ alkenyloxy; phenyl-$C_1$-$C_6$ alkoxy; phenoxy; $C_2$-$C_6$ alkenoyloxy; phenyl-$C_1$-$C_6$ alkanoyloxy; $C_3$-$C_6$ cycloalkyloxy which is substituted by carboxy, esterified carboxy or amidated carboxy; or aminooxy;
$R_5$ is hydrogen or hydroxy;
$R_6$ and $R_7$ each independently, are hydrogen; $C_1$-$C_6$ alkyl; phenyl; benzyl; pyridinyl; $C_1$-$C_6$ alkyl which is substituted by pyridine or

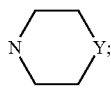

carbonyl which is substituted by $C_1$-$C_6$ alkyl, phenyl, benzyl, pyridine or

$C_1$-$C_6$ alkanesulfonyl; $C_1$-$C_6$ alkyl which is substituted by hydroxy or $C_1$-$C_6$ alkoxy; or acetyl which is substituted by hydroxy or $C_1$-$C_6$ alkoxy;

$X_1$ and $X_3$, each independently, are oxygen; sulfur; NH; N—$C_1$-$C_6$ alkyl; N—$C_3$-$C_6$ cycloalkyl; N-benzyl; or N-phenyl;

$X_2$ is $C_3$-$C_7$ alkylene;

and n is integer of 0 to 6, with the proviso that $R_6$ and $R_7$ both are not hydrogen.

10. The process according to claim 7 wherein the compound of the formula 11 is selected from the group consisting of thioacetamide, thiopropionamide, thioisobutramide, trimethylthioacetamide, thiohexanoylamide, cyclohexanecarbothioic acid amide, and piperidin-4-carbothioic acid amide.

11. The process according to claim 8 or 9 wherein the halide compound of the formulae 15 and 17 is selected from the group consisting of iodomethane, iodoethane, propyl bromide, 2-chloroethyl methyl ether, 2-chloroethylmorpholine, 3-bromomethylpyridine, 2-bromoethanol, niconoyl chloride, benzyl bromide, nicotinoyl chloride, ethanesulfonyl chloride and isoniconoyl chloride.

12. The process according to any one of claims 7-9, wherein, in the conversion of benzonitrile into benzamidine, where $R_5$ is OH, hydroxylamine hydrochloride is used as amine; and the amine is reacted in the presence of a base, wherein the base is organic bases selected from triethylamine, 1,8-diazabicyclo[5.4.0]undec-7-ene, diethylmethylamine ($Et_2NMe$), N-methylmorpholine, N-methylpiperidine, pyridine and 2,6-dimethylpyridine, or inorganic bases selected from potassium carbonate, potassium bicarbonate, sodium hydroxide, potassium hydroxide, sodium amide, sodium hydride, sodium methoxide and sodium ethoxide, at a temperature of 60 to 80° C. for 1 to 9 hours in methanol, ethanol, acetonitrile or its mixture with water.

13. The process according to any one of claims 7-9, wherein, in the conversion of benzonitrile into benzamidine, where $R_5$ is H, methoxy imine prepared from hydrochloride methanol solution at a temperature of 10 to 30° C. for 24 to 48 hours, is reacted with ammonia ethanol solution at a temperature of 45 to 60° C. for 24 to 50 hours.

14. A pharmaceutical composition comprising a therapeutically effective amount of the compound of the formula 1 according to claim 1, the compound of claim 6, or pharmaceutically acceptable salts thereof and a pharmaceutical carrier.

15. Benzamidine derivative of the formula 1 or pharmaceutically acceptable salts thereof:

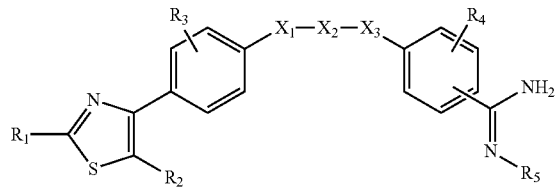

Formula 1 wherein
$R_1$ is $C_1$-$C_6$ alkyl; $C_3$-$C_6$ cycloalkyl; phenyl; benzyl; pyridinyl; guanidino; $NR_6R_7$; $CH_2NR_6R_7$;

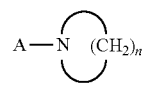

wherein A is $C_1$-$C_6$ alkyl and n is an integer of 2 to 6; $C_1$-$C_6$ alkyl which is substituted by pyridine; or pyridinyl which is substituted by $C_1$-$C_6$ alkyl;

$R_2$ is hydrogen; $C_3$-$C_6$ cycloalkyl; phenyl; benzyl; $C_1$-$C_6$ alkyl which is substituted by hydroxy, $C_1$-$C_6$ alkoxy, halogen or $C_3$-$C_6$ cycloalkyl; or $C_2$-$C_6$ alkenyl;

$R_3$ and $R_4$, each independently, are hydrogen; halogen; hydroxy; $C_1$-$C_6$ alkyl which is unsubstituted or substituted halogen; $C_3$-$C_6$ cycloalkylamino; $C_1$-$C_6$ alkoxy; $C_1$-$C_6$ alkanoyloxy; $C_2$-$C_6$ alkenyloxy; phenyl-$C_1$-$C_6$ alkoxy; phenoxy; $C_2$-$C_6$ alkenoyloxy; phenyl-$C_1$-$C_6$ alkanoyloxy; $C_3$-$C_6$ cycloalkyloxy which is substituted by carboxy, esterified carboxy or amidated carboxy; or aminooxy;

$R_5$ is hydrogen or hydroxy;

$R_6$ and $R_7$, each independently, are hydrogen; $C_1$-$C_6$ alkyl; phenyl; benzyl; pyridinyl; $C_1$-$C_6$ alkyl which is substituted by pyridine or

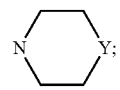

carbonyl which is substituted by $C_1$-$C_6$ alkyl, phenyl, benzyl, pyridine or

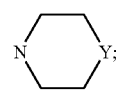

$C_1$-$C_6$ alkanesulfonyl; $C_1$-$C_6$ alkyl which is substituted by hydroxy or $C_1$-$C_6$ alkoxy; or acetyl which is substituted by hydroxy or $C_1$-$C_6$alkoxy;

Y is oxygen; sulfur; $NR_6$; or $CH_2$;

$X_1$ and $X_3$, each independently, are oxygen; sulfur; NH; N—$C_1$-$C_6$ alkyl; N—$C_3$-$C_6$ cycloalkyl; N-benzyl; or N-phenyl;

$X_2$ is $C_3$-$C_7$ alkylene.

16. The compound according to claim 15, wherein
$R_1$ is $C_1$-$C_6$ alkyl; $C_3$-$C_6$ cycloalkyl; phenyl; pyridinyl; guanidino; $NR_6R_7$; $CH_2NR_6R_7$; or

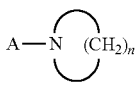

wherein A is $C_1$-$C_6$ alkyl and n is an integer of 2 to 6;
$R_2$ is hydrogen; $C_3$-$C_6$ cycloalkyl; benzyl; $C_1$-$C_6$ alkyl which is substituted by hydroxyl, methoxy, halogen or $C_3$-$C_6$ cycloalkyl; or $C_2$-$C_6$ alkenyl;
$R_3$ and $R_4$, each independently, are hydrogen; halogen; hydroxy; $C_3$-$C_6$ cycloalkylamino; $C_1$-$C_6$ alkoxy; $C_1$-$C_6$ alkanoyloxy; $C_3$-$C_6$ cycloalkyloxy which is substituted by carboxy, esterified carboxy or amidated carboxy; or aminooxy;
$R_5$ is hydrogen or hydroxy;
$R_6$ and $R_7$, each independently, are hydrogen; $C_1$-$C_6$ alkyl; benzyl; pyridinyl; $C_1$-$C_6$ alkyl which is substituted by pyridine or

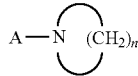

carbonyl which is substituted by pyridine or $C_1$-$C_6$ alkyl; $C_1$-$C_6$ alkanesulfonyl; $C_1$-$C_6$ alkyl which is substituted by hydroxy or $C_1$-$C_6$ alkoxy; or acetyl which is substituted by hydroxy or $C_1$-$C_6$ alkoxy;
Y is oxygen; sulfur; $NR_6$; or $CH_2$;
$X_1$ and $X_3$, each independently, are oxygen; sulfur; NH; or N—$C_1$-$C_6$ alkyl;
$X_2$ is $C_3$-$C_7$ alkylene; or pharmaceutically acceptable salts thereof.

17. The compound according to claim 16, wherein
$R_1$ is methyl; ethyl; propyl; isopropyl; butyl; t-butyl; pentyl; cyclopentyl; hexyl; cyclohexyl; phenyl; isobutylamide; guanidine; 1-propyl-piperidino; $NR_6R_7$; $CH_2NR_6R_7$;

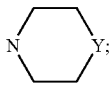

wherein A is $C_1$-$C_6$ alkyl and n is an integer of 2 to 6; or pyridinyl;
$R_2$ is hydrogen; methoxymethyl; hydroxymethyl; 2-methylpropyl; chloromethyl; chloroethyl; cyclopentyl; cyclopentylmethyl; cyclohexyl; benzyl; or vinyl;
$R_3$ and $R_4$, each independently, are hydrogen; halogen; hydroxy; cyclohexylamino; methoxy; or $C_1$-$C_4$ alkanoyloxy;
$R_5$ is hydrogen or hydroxy;
$R_6$ and $R_7$, each independently, are hydrogen; methyl; ethyl; propyl; benzyl; pyridin-3-yl; pyridin-4-yl; 2-morpholinoethyl; 4-pyridinylcarbonyl; 3-pyridinylcarbonyl; isobutylcarbonyl; ethanesulfonyl; methoxyethyl; hydroxyethyl; hydroxyacetyl; or methoxyacetyl;
Y is oxygen; sulfur; $NR_6$; or $CH_2$;
$X_1$ and $X_3$, each independently, are oxygen; sulfur; amine; or methylamine;
$X_2$ is propylene; butylene; pentylene; hexylene; or heptylene; or pharmaceutically acceptable salts thereof.

18. The compound according to claim 17, wherein
$R_1$ is methyl; ethyl; isopropyl; cyclohexyl; phenyl; pyridinyl; $NR_6R_7$; $CH_2NR_6R_7$; or

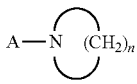

wherein A is $C_1$-$C_2$ alkyl and n is an integer of 4 to 5;
$R_2$ is hydrogen; methoxymethyl; hydroxymethyl; chloromethyl; chloroethyl; cyclopentyl; cyclopentylmethyl; or vinyl;
$R_3$ and $R_4$, each independently, are hydrogen; halogen; hydroxy; or methoxy;
$R_5$ is hydrogen or hydroxy;
$R_6$ and $R_7$, each independently, are hydrogen; methyl; ethyl; benzyl; pyridin-3-yl; pyridin-4-yl; 2-morpholinoethyl; 4-pyridinylcarbonyl; 3-pyridinylcarbonyl; isobutylcarbonyl; ethanesulfonyl; hydroxyethyl; or methoxyethyl;
Y is oxygen; sulfur; or methylamine;
$X_1$ and $X_3$, each independently, are oxygen; sulfur; amino; or methylamine;
$X_2$ is propylene; butylene; pentylene; hexylene; or pharmaceutically acceptable salts thereof.

19. A process for producing a compound of the formula 1a or pharmaceutically acceptable salts thereof which comprises the steps of
1) reacting a compound of the formula 2 with a compound of the formula 3 in the presence of inorganic base to prepare a compound of the formula 4,
2) reacting a compound of the formula 5 with acid chloride of the formula 6 in the presence of inorganic acid to prepare phenone of the formula 7, and reacting the phenone of the formula 7 with acid to prepare a compound of the formula 8,
3) reacting the compound of the formula 4 prepared in step 1) with the compound of the formula 8 prepared in step 2) in the presence of inorganic base to prepare benzonitrile derivatives of the formula 9,
4) reacting the compound of the formula 9 prepared in step 3) with brominating agent to prepare α-brominated compound of the formula 10,
5) reacting α-brominated compound of the formula 10 prepared in step 4) with thioamide compound of the formula 11 to prepare benzonitrile derivatives with thiazole ring of the formula 12, and
6) reacting the compound of the formula 12 prepared in step 5) with amine compound to prepare benzamidine derivatives of the formula 1a, Formula 1a

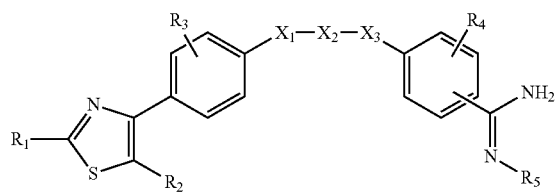

-continued

Formula 2

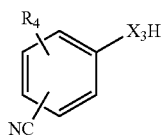

Formula 3

Br—X₂—Br(or Cl)

Formula 4

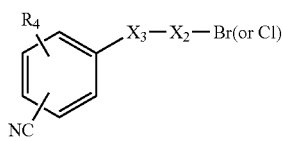

Formula 5

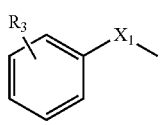

Formula 6

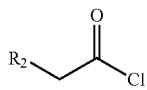

Formula 7

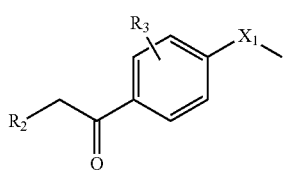

Formula 8

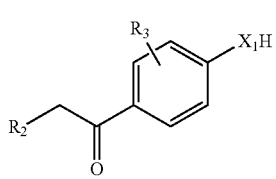

Formula 9

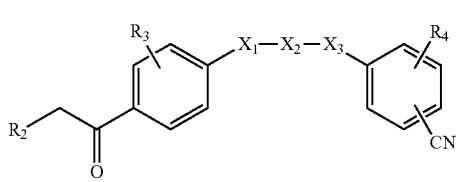

Formula 10

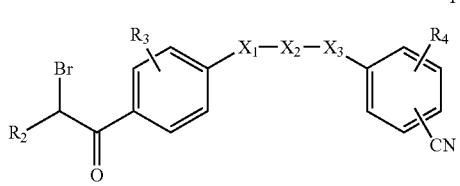

Formula 11

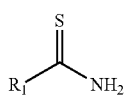

-continued

Formula 12

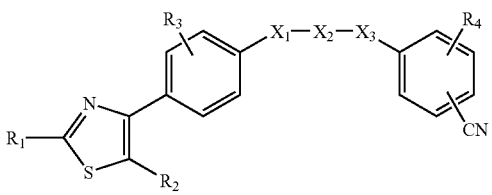

wherein $R_1$ is $C_1$-$C_6$ alkyl; pyridine-substituted $C_1$-$C_6$ alkyl; $C_3$-$C_6$ cycloalkyl; benzyl; phenyl; amino; guanidino; pyridinyl; $C_1$-$C_6$ alkyl-substituted pyridinyl; or

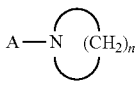

wherein A is $C_1$-$C_6$ alkyl and n is integer of 2 to 6;

$R_2$ is hydrogen; $C_3$-$C_6$ cycloalkyl; phenyl; benzyl; $C_1$-$C_6$ alkyl which is substituted by hydroxy, $C_1$-$C_6$alkoxy, halogen or $C_3$-$C_6$ cycloalkyl; or $C_2$-$C_6$ alkenyl;

$R_3$ and $R_4$, each independently, are hydrogen; halogen; hydroxy; $C_1$-$C_6$ alkyl which is unsubstituted or substituted halogen; $C_3$-$C_6$ cycloalkylamino; $C_1$-$C_6$ alkoxy; $C_1$-$C_6$ alkanoyloxy; $C_2$-$C_6$ alkenyloxy; phenyl-$C_1$-$C_6$ alkoxy; phenoxy; $C_2$-$C_6$ alkenoyloxy; phenyl-$C_1$-$C_6$ alkanoyloxy; $C_3$-$C_6$ cycloalkyloxy which is substituted by carboxy, esterified carboxy or amidated carboxy; or aminooxy;

$R_5$ is hydrogen or hydroxy;

$X_1$ and $X_3$, each independently, are oxygen; sulfur; NH; N—$C_1$-$C_6$ alkyl; N—$C_3$-$C_6$ cycloalkyl; N-benzyl; or N-phenyl;

$X_2$ is $C_3$-$C_7$ alkylene.

20. The compound according to claim 15, wherein pharmaceutically acceptable salt is hydrogen chloride salt or methanesulfonic acid salt.

21. The process according to claim 19, wherein the compound of the formula 11 is selected from the group consisting of thioacetamide, thiopropionamide, thioisobutramide, trimethylthioacetamide, thiohexanoylamide, cyclohexanecarbothioic acid amide, and piperidin-4-carbothioic acid amide.

22. The process according to claim 19, wherein, in the conversion of benzonitrile into benzamidine, where $R_5$ is OH, hydroxylamine hydrochloride is used as amine; and the amine is reacted in the presence of a base, wherein the base is organic bases selected from triethylamine, 1,8-diazabicyclo[5.4.0]undec-7-ene, diethylmethylamine (Et₂NMe), N-methylmorpholine, N-methylpiperidine, pyridine and 2,6-dimethylpyridine, or inorganic bases selected from potassium carbonate, potassium bicarbonate, sodium hydroxide, potassium hydroxide, sodium amide, sodium hydride, sodium methoxide and sodium ethoxide, at a temperature of 60 to 80° C. for 1 to 9 hours in methanol, ethanol, acetonitrile or its mixture with water.

23. The process according to claim 19, wherein, in the conversion of benzonitrile into benzamidine, where $R_5$ is H, methoxy imine prepared from hydrochloride methanol solution at a temperature of 10 to 30° C. for 24 to 48 hours, is reacted with ammonia ethanol solution at a temperature of 45 to 60° C. for 24 to 50 hours.

24. A pharmaceutical composition comprising a therapeutically effective amount of the compound of the formula 1 according to claim 15 or pharmaceutically acceptable salts thereof and a pharmaceutical carrier.

* * * * *